(12) United States Patent
Eberle et al.

(10) Patent No.: US 10,506,934 B2
(45) Date of Patent: Dec. 17, 2019

(54) OPTICAL FIBER PRESSURE SENSOR

(71) Applicant: Phyzhon Health Inc., Rancho Cordova, CA (US)

(72) Inventors: Michael J. Eberle, Fair Oaks, CA (US); Diana Margaret Tasker, Fair Oaks, CA (US); Howard Neil Rourke, Sacramento, CA (US); David J. Spamer, Granite Bay, CA (US)

(73) Assignee: Phyzhon Health Inc., Rancho Cordova, CA (US)

( * ) Notice: Subject to any disclaimer, the term of this patent is extended or adjusted under 35 U.S.C. 154(b) by 653 days.

(21) Appl. No.: 14/403,935

(22) PCT Filed: May 24, 2013

(86) PCT No.: PCT/US2013/042769
§ 371 (c)(1),
(2) Date: Nov. 25, 2014

(87) PCT Pub. No.: WO2013/177577
PCT Pub. Date: Nov. 28, 2013

(65) Prior Publication Data
US 2015/0141843 A1   May 21, 2015

Related U.S. Application Data

(60) Provisional application No. 61/791,486, filed on Mar. 15, 2013, provisional application No. 61/753,221, (Continued)

(51) Int. Cl.
*A61B 5/00* (2006.01)
*A61B 5/0215* (2006.01)
(Continued)

(52) U.S. Cl.
CPC ........ *A61B 5/02154* (2013.01); *A61B 5/0084* (2013.01); *A61B 5/6851* (2013.01);
(Continued)

(58) Field of Classification Search
CPC ................... A61B 5/6851; A61M 2025/09175
(Continued)

(56) References Cited

U.S. PATENT DOCUMENTS

| 3,789,841 A | 2/1974 | Antoshkiw |
| 3,906,938 A | 9/1975 | Fleischhacker |

(Continued)

FOREIGN PATENT DOCUMENTS

| JP | 2003065731 A | 3/2003 |
| JP | 2005291945 A | 10/2005 |

(Continued)

OTHER PUBLICATIONS

"European Application Serial No. 13727763.8, Office Action dated Jul. 12, 2016", 8 pgs.

(Continued)

*Primary Examiner* — Patricia J Park
(74) *Attorney, Agent, or Firm* — Schwegman Lundberg & Woessner, P.A.

(57) ABSTRACT

The disclosure includes an apparatus for insertion into a body lumen. The apparatus can comprise an optical fiber pressure sensor. The optical fiber pressure sensor can comprise an optical fiber configured to transmit an optical sensing signal. A temperature compensated Fiber Bragg Grating (FBG) interferometer can be in optical communication with the optical fiber. The FBG interferometer can be configured to receive a pressure and modulate, in response to the received pressure, the optical sensing signal. A compliant member such as a sensor membrane can be in physical communication with the FBG interferometer. The (Continued)

membrane configured to transmit the received pressure to the FBG interferometer.

22 Claims, 40 Drawing Sheets

Related U.S. Application Data filed on Jan. 16, 2013, provisional application No. 61/709,781, filed on Oct. 4, 2012, provisional application No. 61/659,596, filed on Jun. 14, 2012, provisional application No. 61/651,832, filed on May 25, 2012.

(51) Int. Cl.
  *A61B 8/12* (2006.01)
  *G01L 11/02* (2006.01)
  *G01L 19/14* (2006.01)

(52) U.S. Cl.
  CPC .......... *G01L 11/025* (2013.01); *G01L 19/149* (2013.01); *A61B 2562/0266* (2013.01)

(58) Field of Classification Search
  USPC ............................................ 600/478; 385/13
  See application file for complete search history.

(56) References Cited

U.S. PATENT DOCUMENTS

| | | |
|---|---|---|
| 3,995,623 A | 12/1976 | Blake et al. |
| 4,554,929 A | 11/1985 | Samson et al. |
| 4,712,566 A | 12/1987 | Hok |
| 4,741,590 A | 5/1988 | Caron |
| 4,907,332 A | 3/1990 | Christian et al. |
| 4,917,097 A | 4/1990 | Proudian et al. |
| 4,917,102 A | 4/1990 | Miller et al. |
| 4,932,959 A | 6/1990 | Horzewski et al. |
| 4,936,310 A | 6/1990 | Engstrom et al. |
| 4,941,473 A | 7/1990 | Tenerz et al. |
| 4,955,384 A | 9/1990 | Taylor et al. |
| 4,958,642 A | 9/1990 | Christian et al. |
| 4,961,433 A | 10/1990 | Christian |
| 4,966,163 A | 10/1990 | Kraus et al. |
| 4,967,753 A | 11/1990 | Haase et al. |
| 5,007,434 A | 4/1991 | Doyle et al. |
| 5,018,529 A | 5/1991 | Tenerz |
| 5,050,606 A | 9/1991 | Tremulis |
| 5,059,851 A | 10/1991 | Corl et al. |
| 5,085,223 A | 2/1992 | Lars et al. |
| 5,125,058 A | 6/1992 | Tenerz et al. |
| 5,125,137 A | 6/1992 | Corl et al. |
| 5,135,503 A | 8/1992 | Abrams |
| 5,163,445 A | 11/1992 | Christian et al. |
| 5,167,233 A | 12/1992 | Eberle et al. |
| 5,195,375 A | 3/1993 | Tenerz |
| 5,226,421 A | 7/1993 | Frisbie et al. |
| 5,226,423 A | 7/1993 | Tenerz et al. |
| 5,240,437 A | 8/1993 | Christian |
| 5,246,007 A | 9/1993 | Frisbie et al. |
| 5,271,404 A | 12/1993 | Corl et al. |
| 5,325,860 A | 7/1994 | Seward et al. |
| 5,341,818 A | 8/1994 | Abrams et al. |
| 5,348,481 A | 9/1994 | Ortiz |
| 5,358,409 A | 10/1994 | Obara |
| 5,411,476 A | 5/1995 | Abrams et al. |
| 5,413,508 A | 5/1995 | Obara |
| 5,423,331 A | 6/1995 | Wysham |
| 5,427,118 A | 6/1995 | Nita et al. |
| 5,514,128 A | 5/1996 | Hillsman et al. |
| 5,517,989 A | 5/1996 | Frisbie et al. |
| 5,520,194 A | 5/1996 | Miyata et al. |
| 5,551,301 A | 9/1996 | Cowan |
| 5,558,101 A | 9/1996 | Brooks et al. |
| 5,571,094 A | 11/1996 | Sirhan |
| 5,581,144 A | 12/1996 | Corl et al. |
| 5,668,320 A | 1/1997 | Cowan |
| 5,603,327 A | 2/1997 | Eberle et al. |
| 5,607,419 A | 3/1997 | Amplatz et al. |
| 5,637,089 A | 6/1997 | Abrams et al. |
| RE35,648 E | 11/1997 | Tenerz et al. |
| 5,688,234 A | 11/1997 | Frisbie |
| 5,694,946 A | 12/1997 | Tenerz et al. |
| 5,695,111 A | 12/1997 | Nanis et al. |
| 5,715,827 A | 2/1998 | Corl et al. |
| 5,740,596 A | 4/1998 | Corl et al. |
| 5,797,856 A | 8/1998 | Frisbie et al. |
| 5,873,835 A | 2/1999 | Hastings et al. |
| 5,897,819 A | 4/1999 | Miyata et al. |
| 5,908,385 A | 6/1999 | Chechelski et al. |
| 5,910,364 A | 6/1999 | Miyata et al. |
| 5,938,624 A | 8/1999 | Akerfeldt et al. |
| 5,984,853 A | 11/1999 | Smith |
| 6,025,670 A | 2/2000 | Corl et al. |
| 6,049,958 A | 4/2000 | Eberle et al. |
| 6,089,103 A | 7/2000 | Smith |
| 6,090,052 A | 7/2000 | Akerfeldt et al. |
| 6,106,476 A | 8/2000 | Corl et al. |
| 6,106,486 A | 8/2000 | Tenerz et al. |
| 6,112,598 A | 9/2000 | Tenerz et al. |
| 6,142,958 A | 11/2000 | Hammarstrom et al. |
| 6,165,292 A | 12/2000 | Abrams et al. |
| 6,167,763 B1 * | 1/2001 | Tenerz ................ A61B 5/0215 73/756 |
| 6,175,669 B1 | 1/2001 | Colston et al. |
| 6,182,513 B1 | 2/2001 | Stemme et al. |
| 6,191,862 B1 | 2/2001 | Swanson et al. |
| 6,196,980 B1 | 3/2001 | Akerfeldt et al. |
| 6,210,339 B1 | 4/2001 | Kiepen et al. |
| 6,241,651 B1 | 6/2001 | Smith et al. |
| 6,248,083 B1 | 6/2001 | Smith et al. |
| 6,265,792 B1 | 7/2001 | Granchukoff |
| 6,280,539 B1 | 8/2001 | Abrams et al. |
| 6,312,380 B1 | 11/2001 | Hoek et al. |
| 6,336,906 B1 | 1/2002 | Hammarstrom et al. |
| 6,343,514 B1 | 2/2002 | Smith |
| 6,379,369 B1 | 4/2002 | Abrams et al. |
| 6,390,993 B1 | 5/2002 | Cornish et al. |
| 6,409,677 B1 | 6/2002 | Tulkki |
| 6,419,745 B1 | 7/2002 | Burkett et al. |
| 6,423,012 B1 | 7/2002 | Kato et al. |
| 6,428,336 B1 | 8/2002 | Akerfeldt |
| 6,445,939 B1 | 9/2002 | Swanson et al. |
| 6,461,301 B2 | 10/2002 | Smith |
| 6,461,453 B1 | 10/2002 | Abrams et al. |
| 6,491,648 B1 | 12/2002 | Cornish et al. |
| 6,517,481 B2 | 2/2003 | Hoek et al. |
| 6,546,804 B2 | 4/2003 | Stemme et al. |
| 6,552,796 B2 | 4/2003 | Magnin et al. |
| 6,565,514 B2 | 5/2003 | Svanerudh et al. |
| 6,570,659 B2 | 5/2003 | Schmitt |
| 6,585,660 B2 | 7/2003 | Dorando et al. |
| 6,592,570 B2 | 7/2003 | Abrams et al. |
| 6,602,228 B2 | 8/2003 | Nanis et al. |
| 6,615,067 B2 | 9/2003 | Hoek et al. |
| 6,615,667 B2 | 9/2003 | Smith |
| 6,659,957 B1 | 12/2003 | Vardi et al. |
| 6,666,829 B2 | 12/2003 | Cornish et al. |
| 6,672,172 B2 | 1/2004 | Tulkki et al. |
| 6,673,025 B1 | 1/2004 | Richardson et al. |
| 6,682,608 B2 | 1/2004 | Abrams et al. |
| 6,692,446 B2 | 2/2004 | Hoek |
| 6,695,915 B2 | 2/2004 | Burkett et al. |
| 6,733,819 B2 | 5/2004 | Burkett et al. |
| 6,754,608 B2 | 6/2004 | Svanerudh et al. |
| 6,767,327 B1 | 7/2004 | Corl et al. |
| 6,779,257 B2 | 8/2004 | Kiepen et al. |
| 6,813,421 B2 * | 11/2004 | Lail ...................... G02B 6/4411 385/101 |
| 6,852,109 B2 | 2/2005 | Winston |
| 6,884,225 B2 | 4/2005 | Kato et al. |
| 6,891,984 B2 | 5/2005 | Petersen et al. |
| 6,908,442 B2 | 6/2005 | von Malmborg et al. |

(56) References Cited

U.S. PATENT DOCUMENTS

| | | |
|---|---|---|
| 6,926,674 B2 | 8/2005 | Tenerz et al. |
| 6,938,474 B2 | 9/2005 | Melvås |
| 6,976,965 B2 | 12/2005 | Corl et al. |
| 6,993,974 B2 | 2/2006 | Tenerz et al. |
| 7,003,184 B2 | 2/2006 | Ronnekleiv et al. |
| 7,011,636 B2 | 3/2006 | Tenerz |
| 7,021,152 B2 | 4/2006 | Tenerz |
| 7,097,620 B2 | 8/2006 | Corl et al. |
| 7,117,703 B2 | 10/2006 | Kato et al. |
| 7,150,723 B2 | 12/2006 | Meguro et al. |
| 7,182,757 B2 | 2/2007 | Miyata et al. |
| 7,187,453 B2 | 3/2007 | Belleville |
| 7,222,539 B2 | 5/2007 | Tulkki |
| 7,241,286 B2 | 7/2007 | Atlas |
| 7,244,319 B2 | 7/2007 | Abrams et al. |
| 7,245,789 B2 | 7/2007 | Bates et al. |
| 7,254,946 B1 | 8/2007 | Quinn |
| 7,259,862 B2 | 8/2007 | Duplain |
| 7,263,894 B2 | 9/2007 | Tenerz |
| 7,274,956 B2 | 9/2007 | Mott et al. |
| RE39,863 E | 10/2007 | Smith |
| 7,326,088 B2 | 2/2008 | Tulkki |
| 7,331,236 B2 | 2/2008 | Smith et al. |
| 7,343,811 B2 | 3/2008 | Tenerz et al. |
| 7,399,283 B2 | 7/2008 | Kato |
| 7,447,388 B2 | 11/2008 | Bates et al. |
| 7,450,989 B2 | 11/2008 | Svanerudh |
| 7,472,601 B1 | 1/2009 | Tenerz et al. |
| 7,532,920 B1 | 5/2009 | Ainsworth et al. |
| 7,553,444 B2 | 6/2009 | Kato |
| 7,645,233 B2 | 1/2010 | Tulkki et al. |
| 7,660,492 B2 | 2/2010 | Bates et al. |
| 7,676,910 B2 | 3/2010 | Kiepen et al. |
| 7,680,363 B2 | 3/2010 | Wakahara et al. |
| 7,689,071 B2 | 3/2010 | Belleville et al. |
| 7,724,148 B2 | 5/2010 | Samuelsson et al. |
| 7,753,852 B2 | 7/2010 | Maschke |
| 7,762,954 B2 | 7/2010 | Nix et al. |
| 7,775,988 B2 | 8/2010 | Pijls |
| 7,775,992 B2 | 8/2010 | von Malmborg et al. |
| 7,914,458 B2 | 3/2011 | Hossack et al. |
| 7,918,947 B2 | 4/2011 | Kato |
| 7,931,603 B2 | 4/2011 | Von Malmborg et al. |
| 7,946,997 B2 | 5/2011 | Hubinette |
| 7,967,761 B2 | 6/2011 | Smith |
| 7,967,762 B2 | 6/2011 | Corl et al. |
| 7,998,089 B2 | 8/2011 | Smith |
| 8,038,628 B2 | 10/2011 | von Malmborg et al. |
| 8,059,923 B2 | 11/2011 | Bates et al. |
| 8,298,156 B2 | 10/2012 | Manstrom et al. |
| 8,317,715 B2 | 11/2012 | Belleville et al. |
| 8,412,312 B2 | 4/2013 | Judell et al. |
| 8,478,384 B2 | 7/2013 | Schmitt et al. |
| 8,485,985 B2 | 7/2013 | Manstrom |
| 8,583,218 B2 | 11/2013 | Eberle |
| 8,641,639 B2 | 2/2014 | Manstrom et al. |
| 8,676,299 B2 | 3/2014 | Schmitt et al. |
| 8,677,299 B1 | 3/2014 | Alpert et al. |
| 2002/0059827 A1 | 5/2002 | Smith |
| 2003/0125719 A1 | 7/2003 | Furnish |
| 2003/0220588 A1 | 11/2003 | Tenerz et al. |
| 2004/0082879 A1* | 4/2004 | Klint ............... A61B 17/12022 600/585 |
| 2004/0180581 A1 | 9/2004 | von Malmborg et al. |
| 2004/0225232 A1 | 11/2004 | Malmborg et al. |
| 2005/0121734 A1 | 6/2005 | Degertekin et al. |
| 2006/0183992 A1 | 8/2006 | Kawashima |
| 2006/0241483 A1 | 10/2006 | Nix et al. |
| 2006/0241503 A1 | 10/2006 | Schmitt et al. |
| 2006/0241505 A1 | 10/2006 | Ahmed et al. |
| 2007/0078500 A1* | 4/2007 | Ryan ............... A61B 5/0066 607/88 |
| 2007/0116408 A1* | 5/2007 | Eberle ............... A61B 1/00165 385/31 |
| 2007/0156019 A1 | 7/2007 | Larkin et al. |
| 2007/0255144 A1 | 11/2007 | Tulkki et al. |
| 2008/0161696 A1 | 7/2008 | Schmitt et al. |
| 2008/0165366 A1 | 7/2008 | Schmitt |
| 2008/0285909 A1* | 11/2008 | Younge ............... A61B 5/1076 385/13 |
| 2009/0036754 A1 | 2/2009 | Pons et al. |
| 2009/0137952 A1* | 5/2009 | Ramamurthy ............ A61B 5/06 604/95.01 |
| 2009/0180730 A1 | 7/2009 | Foster et al. |
| 2010/0087732 A1 | 4/2010 | Eberle et al. |
| 2010/0199773 A1 | 8/2010 | Zhou |
| 2010/0228112 A1 | 9/2010 | Von Malmborg |
| 2010/0234698 A1 | 9/2010 | Manstrom et al. |
| 2010/0241008 A1 | 9/2010 | Belleville et al. |
| 2011/0071405 A1 | 3/2011 | Judell et al. |
| 2011/0144502 A1 | 6/2011 | Zhou et al. |
| 2011/0178413 A1* | 7/2011 | Schmitt ............... A61B 5/0066 600/478 |
| 2012/0108943 A1 | 5/2012 | Bates et al. |
| 2012/0136244 A1 | 5/2012 | Manstrom et al. |
| 2012/0197097 A1* | 8/2012 | Chan ............... A61B 1/00165 600/342 |
| 2012/0220883 A1 | 8/2012 | Manstrom et al. |
| 2012/0227505 A1 | 9/2012 | Belleville |
| 2012/0238869 A1 | 9/2012 | Schmitt et al. |
| 2012/0310081 A1 | 12/2012 | Adler et al. |
| 2013/0022308 A1* | 1/2013 | Wild ............... G01B 11/18 385/12 |
| 2013/0051731 A1 | 2/2013 | Belleville |
| 2013/0096409 A1 | 4/2013 | Hiltner |
| 2013/0131523 A1 | 5/2013 | Suchecki et al. |
| 2013/0218032 A1 | 8/2013 | Belleville |
| 2013/0303914 A1 | 11/2013 | Hiltner et al. |
| 2013/0310698 A1 | 11/2013 | Judell et al. |
| 2013/0317359 A1 | 11/2013 | Wilson et al. |
| 2013/0317372 A1 | 11/2013 | Eberle et al. |
| 2013/0324864 A1 | 12/2013 | Manstrom |
| 2013/0331714 A1 | 12/2013 | Manstrom et al. |
| 2014/0005558 A1 | 1/2014 | Gregorich |
| 2014/0024950 A1 | 1/2014 | Hiltner et al. |
| 2014/0039325 A1 | 2/2014 | Belleville |
| 2014/0058275 A1 | 2/2014 | Gregorich et al. |
| 2014/0081244 A1 | 3/2014 | Voeller et al. |
| 2014/0094697 A1 | 4/2014 | Petroff et al. |
| 2014/0100462 A1 | 4/2014 | Rourke et al. |
| 2014/0107624 A1 | 4/2014 | Belleville |
| 2014/0180031 A1 | 6/2014 | Anderson |
| 2014/0180034 A1 | 6/2014 | Hoseit et al. |
| 2014/0200438 A1 | 7/2014 | Millett et al. |
| 2015/0141854 A1 | 5/2015 | Eberle et al. |
| 2015/0196210 A1 | 7/2015 | Mccaffrey et al. |
| 2016/0018593 A1 | 1/2016 | Tasker et al. |
| 2016/0022159 A1 | 1/2016 | Caron et al. |
| 2016/0038030 A1 | 2/2016 | Smith et al. |

FOREIGN PATENT DOCUMENTS

| | | |
|---|---|---|
| JP | 2006501930 A | 1/2006 |
| JP | 2008107141 A | 5/2008 |
| JP | 2008175560 A | 7/2008 |
| JP | 2009516831 A | 4/2009 |
| JP | 2009264748 A | 11/2009 |
| JP | 2011000469 A | 1/2011 |
| JP | 6220868 B2 | 10/2017 |
| WO | WO-2002019903 A1 | 3/2002 |
| WO | WO-2007041542 A2 | 4/2007 |
| WO | WO-2007/120678 A2 | 10/2007 |
| WO | WO-2008/011663 A1 | 1/2008 |
| WO | WO-2012061935 A1 | 5/2012 |
| WO | WO-2013177577 A2 | 11/2013 |
| WO | WO-2013177577 A3 | 11/2013 |

OTHER PUBLICATIONS

"European Application Serial No. 13727763.8, Response filed Jul. 12, 2016 to Office Action dated Jan. 18, 2016", 18 pgs.

"Japanese Application Serial No. 2015-514239, Voluntary Amend-

(56) References Cited

OTHER PUBLICATIONS ment filed Feb. 24, 2015", (w/ English Translation of Claims), 6 pgs.
"European Applcation Serial No. 13727763.8, Office Action dated Jan. 14, 2015", 2 pgs.
"International Application Serial No. PCT/US2013/042769, International Preliminary Report on Patentability dated Dec. 4, 2014", 12 pgs.
Siebes, M., et al., "Single-Wire Pressure and Flow Velocity Measurement to Quantify Coronary Stenosis Hernodynamics and Effects of Percutaneous Interventions", *Circulation*, 109, (2004), 756-762.
"U.S. Appl. No. 13/902,334, Decision on Pre-Appeal Brief Request dated Jan. 25, 2019", 4 pgs.
"U.S. Appl. No. 13/902,334, Examiner Interview Summary dated Jan. 25, 2019", 2 pgs.
"U.S. Appl. No. 13/902,334, Final Office Action dated Jul. 19, 2018", 18 pgs.
"U.S. Appl. No. 13/902,334, Pre-Appeal Brief Request filed Nov. 5, 2018", 4 pgs.
"U.S. Appl. No. 13/902,334, Response filed Jan. 30, 2019 to Final Office Action dated Jul. 19, 2018", 13 pgs.
"U.S. Appl. No. 13/902,334, Response filed May 2, 2018 to Non Final Office Action dated Nov. 22, 2017", 13 pgs.
"U.S. Appl. No. 14/549,287, Decision on Pre-Appeal Brief dated Sep. 6, 2018", 2 pgs.
"U.S. Appl. No. 14/549,287, Pre-Appeal Brief Request filed Jun. 26, 2018", 5.
"U.S. Appl. No. 14/549,287, Response filed Nov. 26, 2018 to Final Office Action dated Dec. 29, 2017", 12 pgs.
"European Application Serial No. 13727763.8, Examiner Interview Summary", w/ English Claims, 177 pgs.
"European Application Serial No. 13727763.8, Response filed Jun. 15, 2018 to Communication Pursuant to Article 94(3) EPC dated Feb. 5, 2018", 117 pgs.
"U.S. Appl. No. 14/549,287, Non Final Office Action dated Mar. 14, 2019", 12 pgs.
"Canadian Application Serial No. 2,911,446, Office Action dated Mar. 25, 2019", 4 pgs.
"U.S. Appl. No. 14/549,287, Non Final Office Action dated Mar. 28, 2017", 12 pgs.
"U.S. Appl. No. 14/549,287, Response filed Sep. 22, 2017 to Non Final Office Action dated Mar. 28, 2017", 14 pgs.
"Japanese Application Serial No. 2015-514239, Response filed Aug. 14, 2017 to Office Action dated Mar. 21, 2017", w/ English Claims.
"European Application Serial No. 13727763.8, Communication Pursuant to Article 94(3) EPC dated Feb. 5, 2018", 3 pgs.
"U.S. Appl. No. 13/902,334, Response filed Jun. 12, 2017 to Restriction Requirement dated Jan. 19, 2017", 11 pgs.

"U.S. Appl. No. 13/902,334, Restriction Requirement dated Jan. 19, 2017", 7 pgs.
"Japanese Application Serial No. 2015-514239, Office Action dated Mar. 21, 2017", w/ English Translation, 7 pgs.
"U.S. Appl. No. 13/902,334, Non Final Office Action dated Nov. 22, 2017", 18 pgs.
"U.S. Appl. No. 14/549,287, Final Office Action dated Dec. 29, 2017", 12 pgs.
U.S. Appl. No. 13/902,334, Amendment filed Nov. 4, 2013, 9 pgs.
"Fiber optic miniature pressure sensor OPP-M: 0.25 & 0.40 mm OD MEMS-Based Fiber Optic Pressure Sensor for Life Science Applications", Product Brochure, Publication No. IMP0006 OPP-M Rev. 2.0, Opsens Inc., Quebec City, Canada (Feb. 27, 2012), 2 pgs.
"HI-TORQUE Guide Wires", Product Brochure, Publication No. PPL2073897, Abbott Vascular, Santa Clara, CA (Feb. 8, 2010), 6 p.
International Application Serial No. PCT/US2013/042769, International Search Report dated Mar. 10, 2014, 6 pgs.
International Application Serial No. PCT/US2013/042769, Invitation to Pay Additional Fees and Partial Search Report dated Dec. 5, 2013, 7 pgs.
International Application Serial No. PCT/US2013/042769, Written Opinion dated Mar. 10, 2014, 10 pgs.
"OPP-M Fiber optic miniature physiological pressure sensor", [Online]. Retrieved from the Internet: <http://opsens.com/en/industries/products/pressure/opp-m/>, (Accessed Feb. 27, 2012), 1 pg.
"Opsens Signs First Major Agreement in the Medical Field Granting Distribution Rights of Its Ffr Products for Japan, Korea and Taiwan in Us$5 Million Transaction", Press Release, Opsens Inc., Quebec City, Canada, (Nov. 19, 2012), 3 pgs.
"Optical Pressure & Temperature Sensing", Product Presentation, Opsens Inc., Quebec City, Canada (Feb. 27, 2012), 29 pgs.
"Route / PROWATERflex and Rinato / Prowater Guidewire Specifications", [Online] Retrieved from the Internet: <http://www.asahi-intecc.com/medical/international/product/ptca_gw.php>, (Accessed May 24, 2012), 1 pg.
Haga, Y., et al., "Multi-functional Active Catheter", Sensors update, vol. 8, Issue 1, (Nov. 2000), 147-186.
Mineta, T., et al., "Batch fabricated flat meandering shape memory alloy actuator for active catheter", Sensors and Actuators, A 88 (2001), 112-120.
Mineta, T., et al., "An active guide wire with shape memory alloy bending actuator fabricated by room temperature process", Sensors and Actuators, A 97-98, (2002), 632-637.
"U.S. Appl. No. 14/549,287, Response filed Jun. 10, 2019 to Non Final Office Action dated Mar. 14, 2019", 14 pgs.
"U.S. Appl. No. 13/902,334, Non Final Office Action dated Jul. 9, 2019", 18 pgs.

* cited by examiner

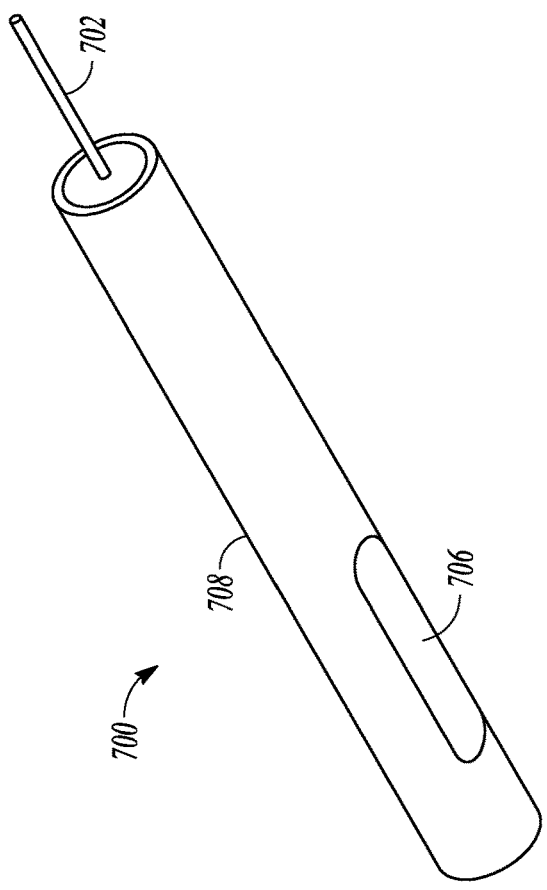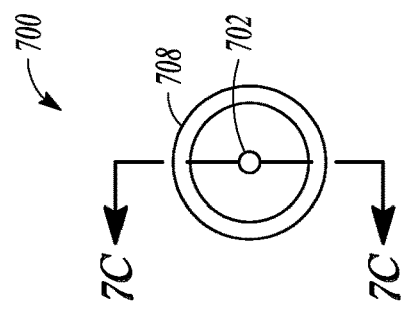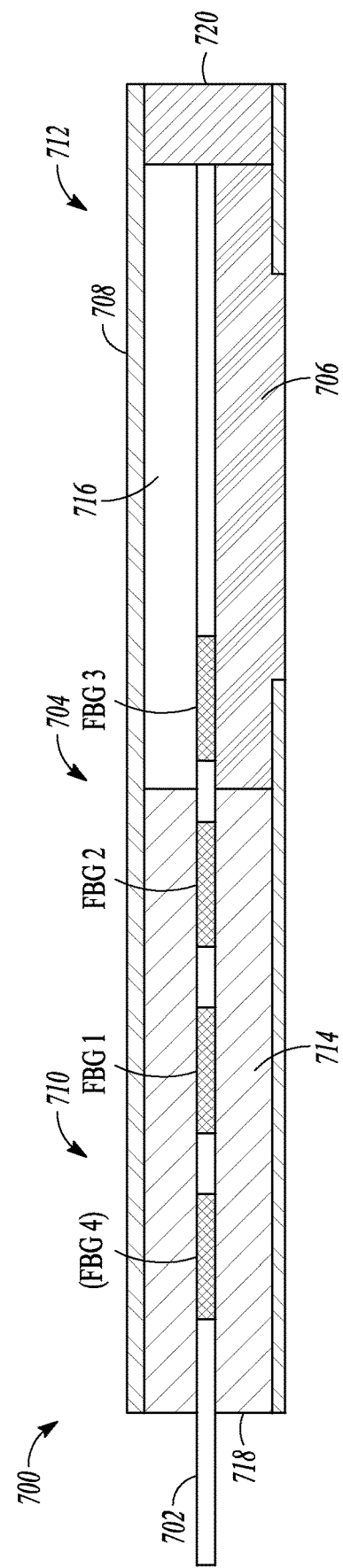
FIG. 7A
FIG. 7B
FIG. 7C

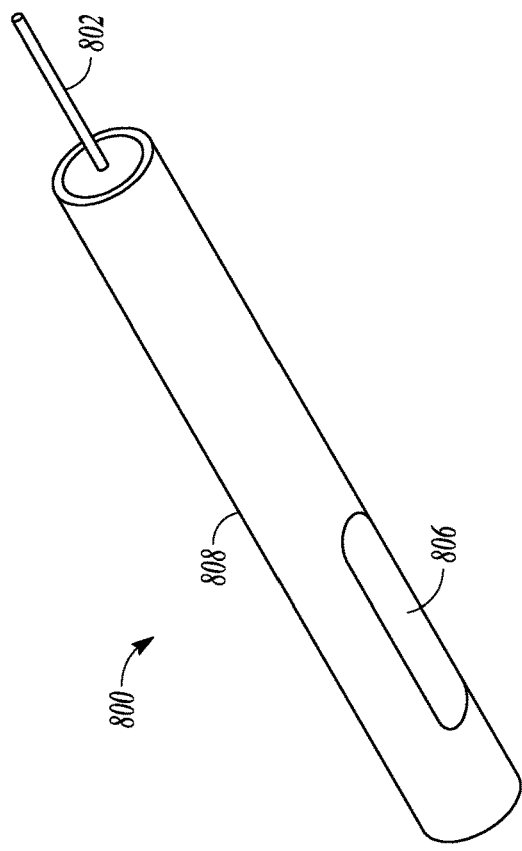
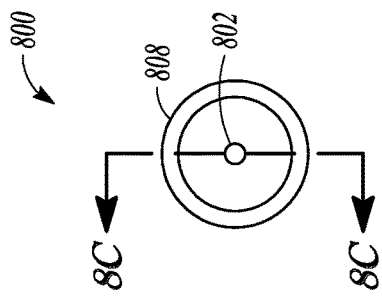
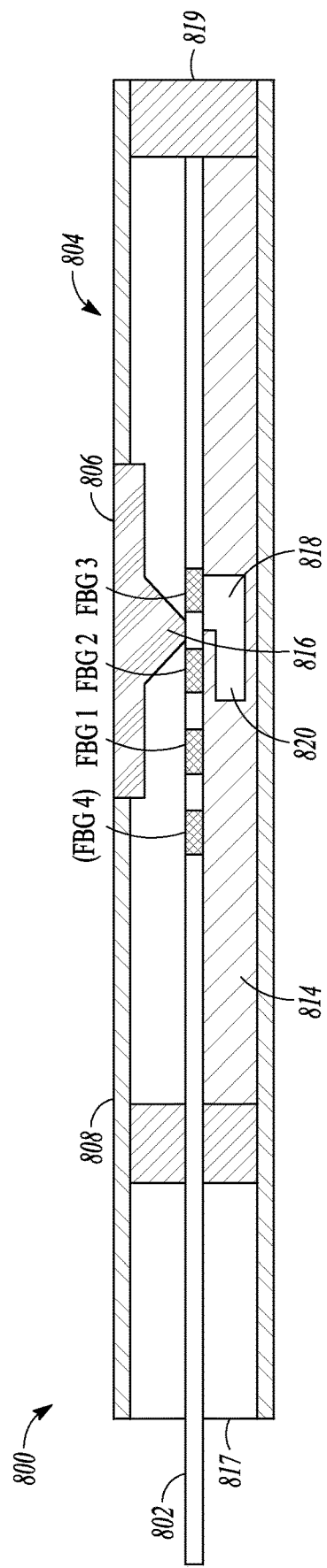
FIG. 8A
FIG. 8B
FIG. 8C

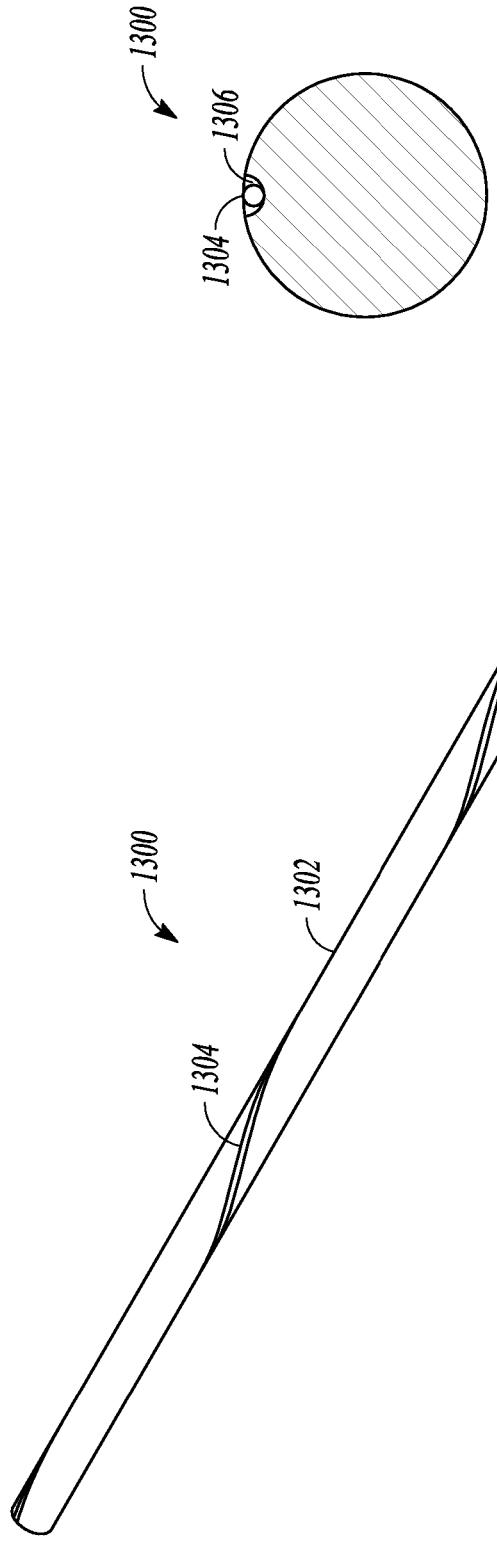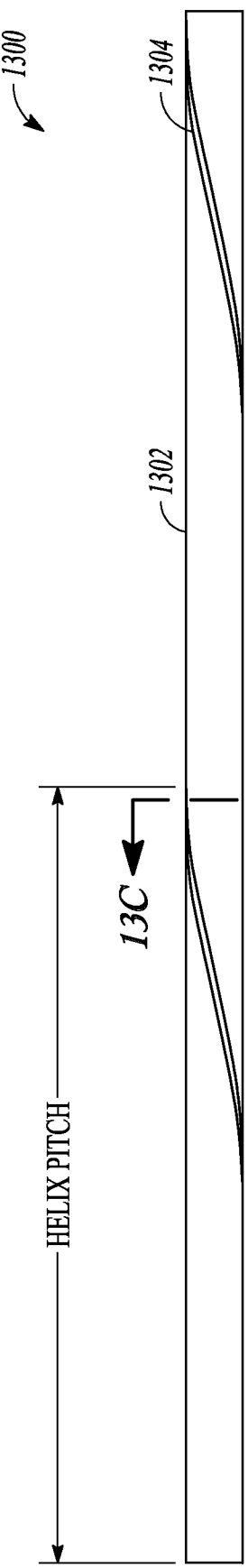
FIG. 13A
FIG. 13B
FIG. 13C

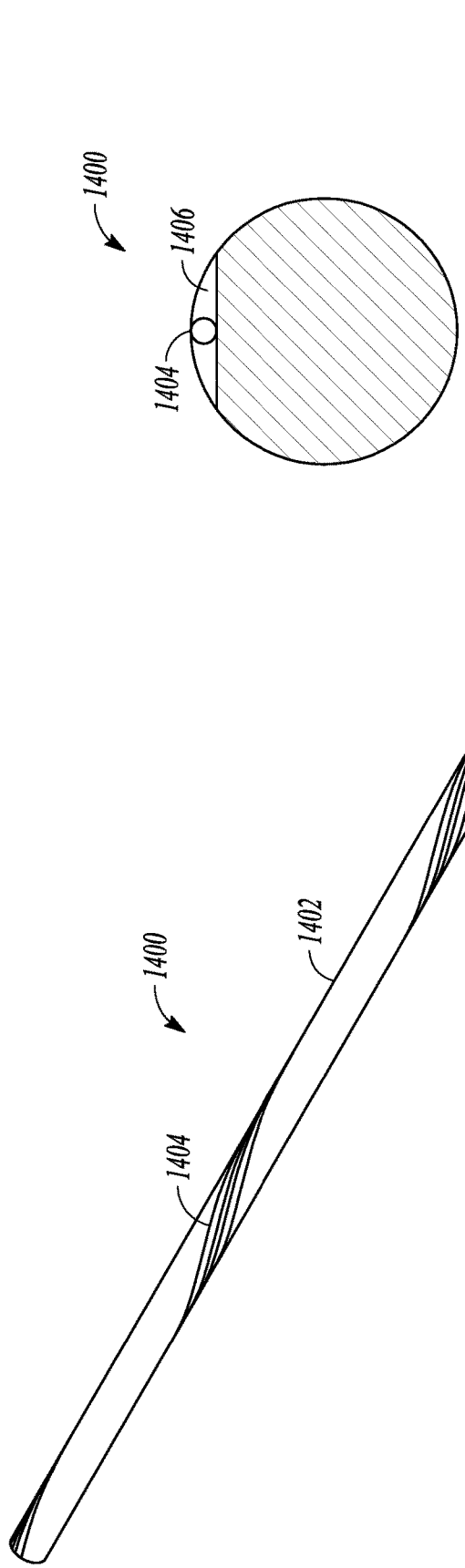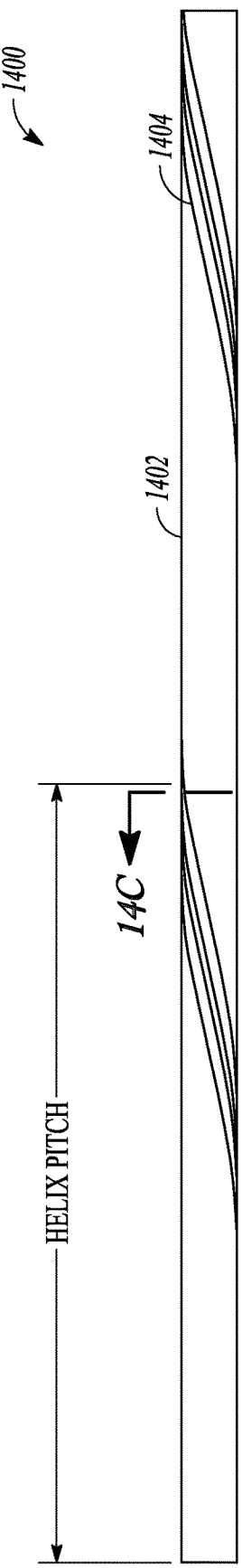

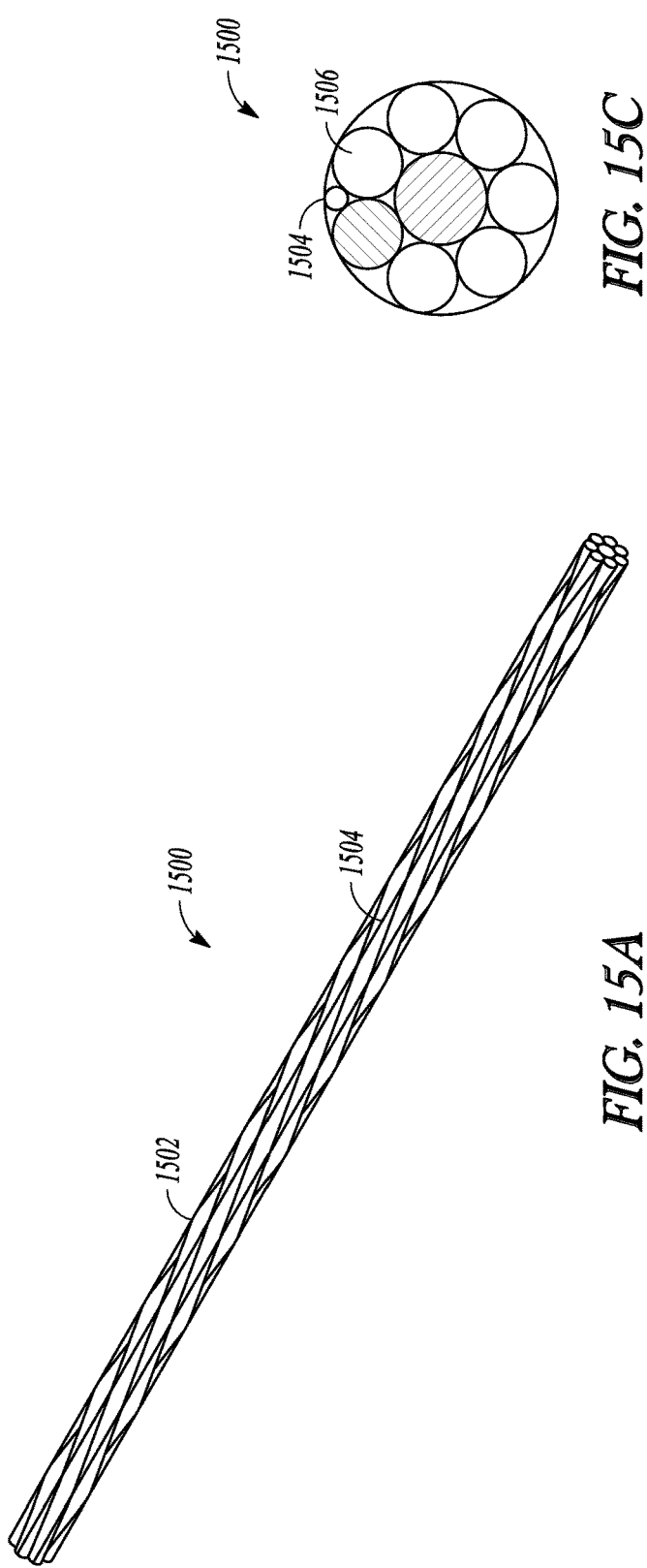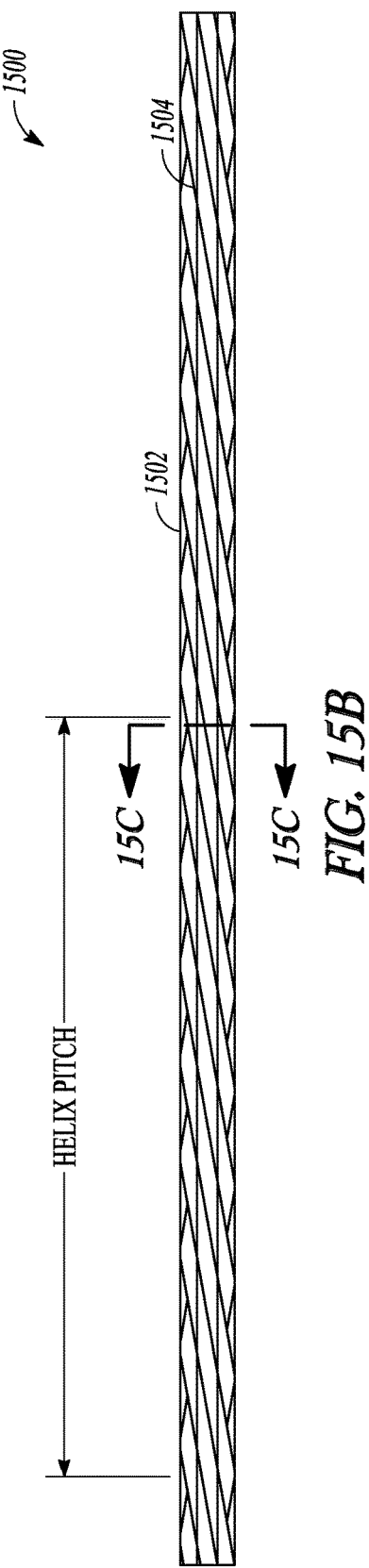

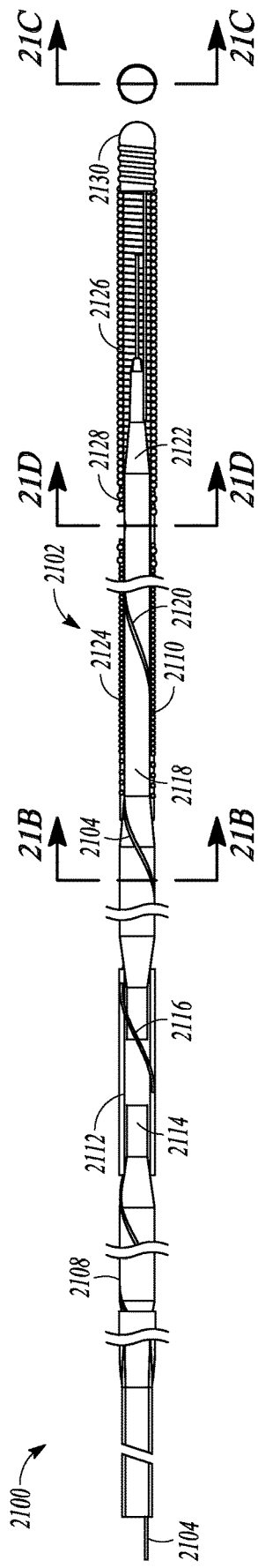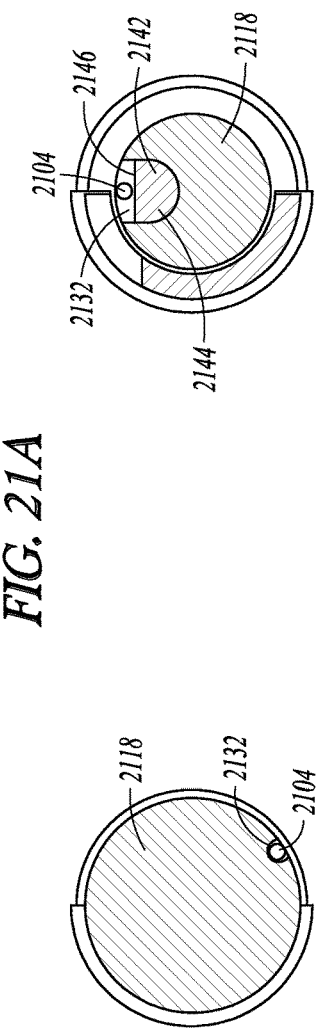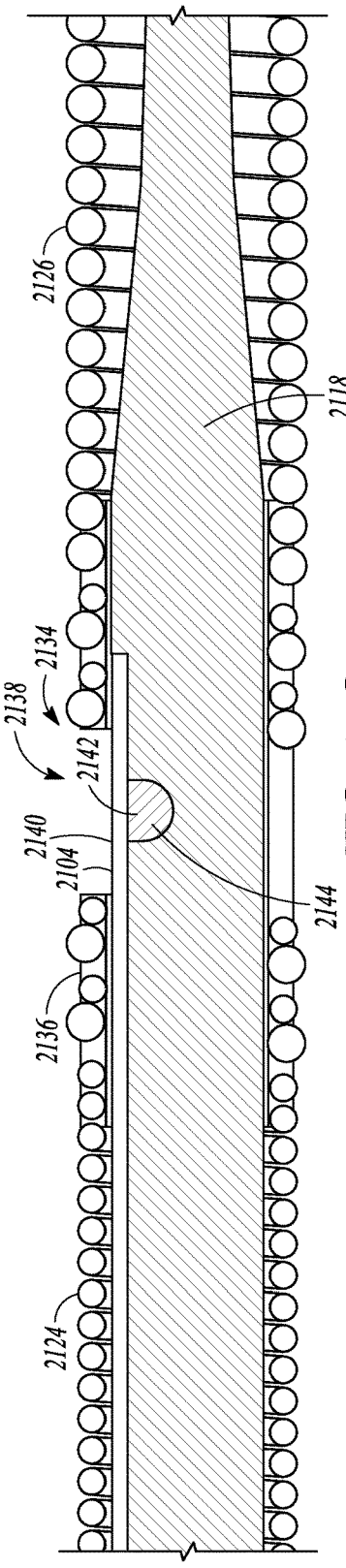
FIG. 21A
FIG. 21B
FIG. 21D
FIG. 21C

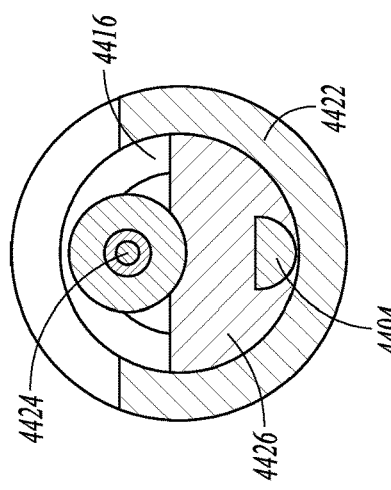
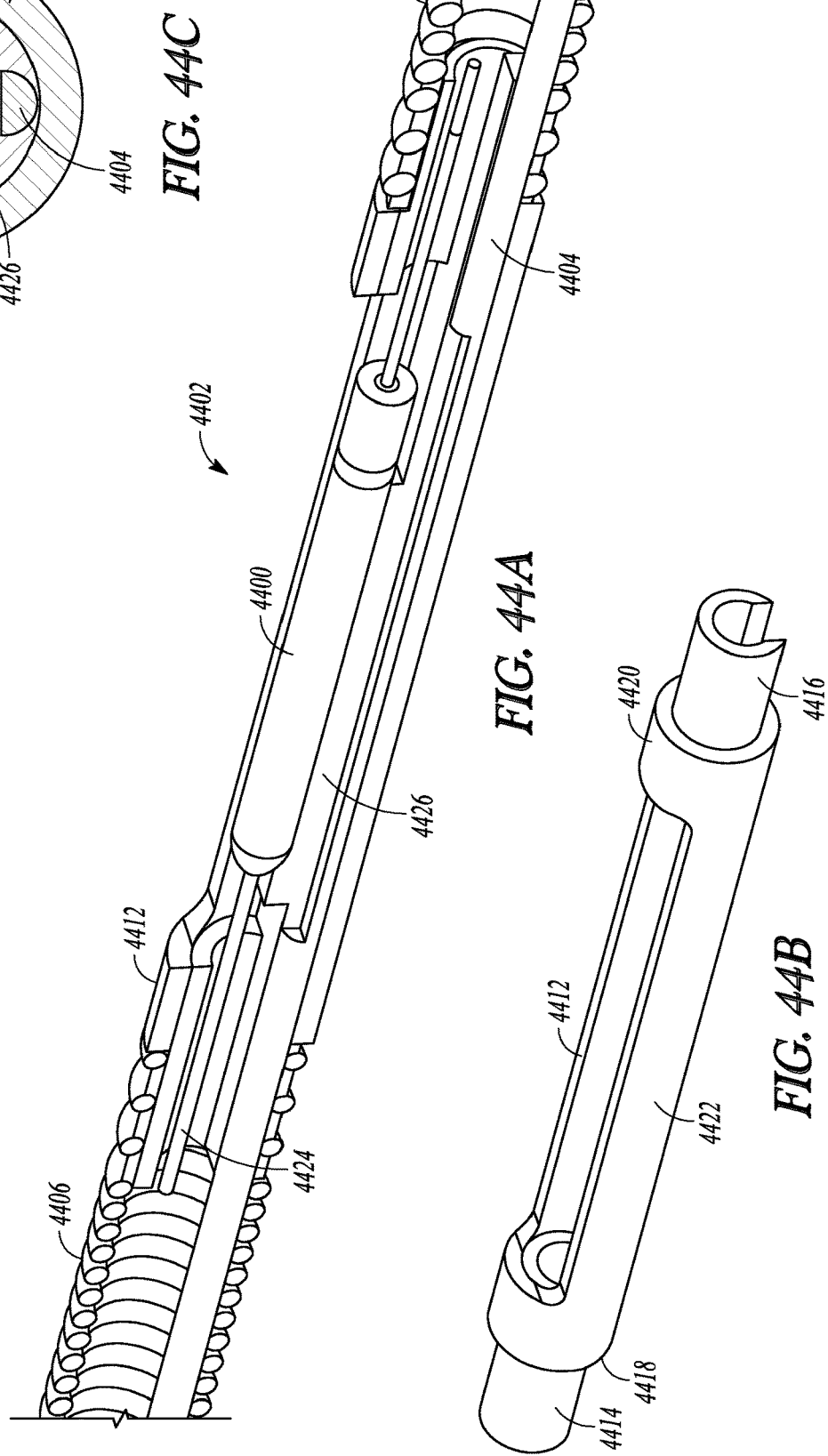
FIG. 44C
FIG. 44A
FIG. 44B

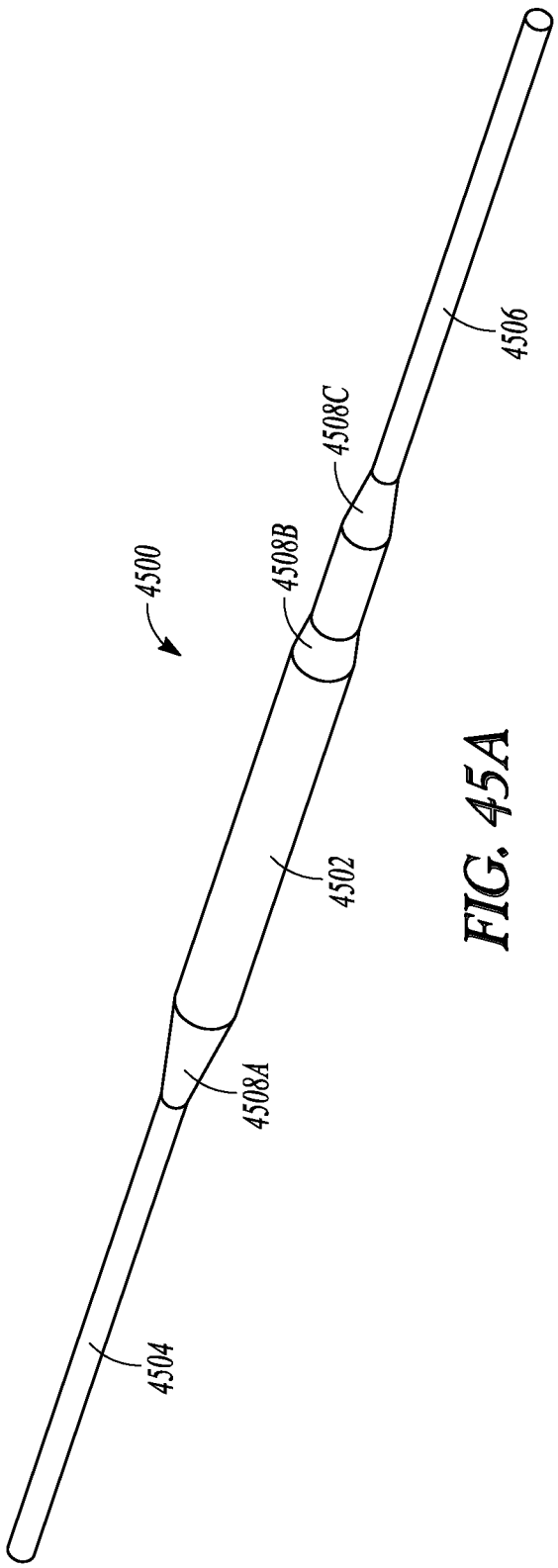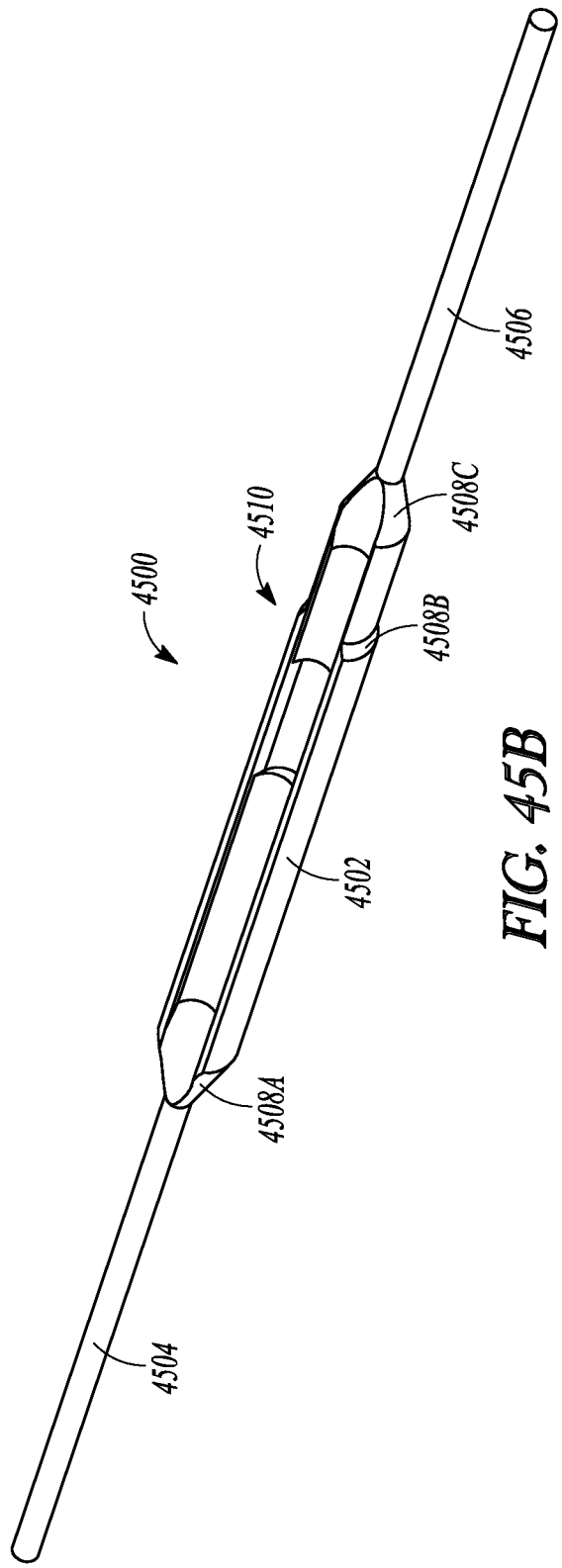

OPTICAL FIBER PRESSURE SENSOR

This application is a U.S. National Stage Filing under 35 U.S.C. § 371 from International Application No. PCT/US2013/042769, entitled "OPTICAL FIBER PRESSURE SENSOR," filed on May 24, 2013, and published as WO 2013/177577 A1 on Nov. 28, 2013, which claims the benefit of priority under 35 U.S.C. § 119(e) to (1) U.S. Provisional Application No. 61/791,486 entitled, "OPTICAL FIBER PRESSURE SENSOR GUIDEWIRE" to Eberle et al. and filed on Mar. 15, 2013, and to (2) U.S. Provisional Application No. 61/753,221, entitled, "OPTICAL FIBER PRESSURE SENSOR GUIDEWIRE" to Eberle et al. and filed on Jan. 16, 2013, and to (3) U.S. Provisional Application No. 61/709,781, entitled, "OPTICAL FIBER PRESSURE SENSOR GUIDEWIRE" to Eberle et al. and filed on Oct. 4, 2012, and to (4) U.S. Provisional Application No. 61/659,596, entitled, "OPTICAL FIBER PRESSURE SENSOR GUIDEWIRE" to Eberle et al. and filed on Jun. 14, 2012, and to (5) U.S. Provisional Application No. 61/651,832, entitled, "OPTICAL FIBER PRESSURE SENSOR GUIDEWIRE" to Eberle et al. and filed on May 25, 2012, the entire content of each being incorporated herein by reference in its entirety, and the benefit of priority of each is claimed herein.

TECHNICAL FIELD

This document pertains generally to pressure sensing devices and methods and, in particular, to pressure sensing devices and methods using optical elements and techniques.

BACKGROUND

U.S. Patent Application Publication No. 2009/0180730 to Foster et al. is directed toward a device for sensing an acoustic signal. The device includes a flexible portion including a laser active region having an emitted wavelength that varies according to a mechanical force acting on the flexible portion, and including a flexible support member operable to flex or bend according to the acoustic signal. The flexible portion is coupled with the support member so as to cause the flexible portion to flex or bend in accordance with the support member, thereby changing the emitted wavelength of the laser active region of the flexible portion.

U.S. Pat. No. 7,680,363 to Wakahara et al. ("Wakahara") is directed toward an optical fiber pressure sensor capable of detecting a more minute pressure change. A base film is formed with a through hole passing through first and second surfaces. An optical fiber is fixed to the base film at a region other than the Fiber Bragg Grating (FBG) portion, such that the FBG portion is positioned on the through hole in plan view. The optical fiber pressure sensor is attached to an object body such that the second surface of the base film is closely attached to a surface of the object body directly or indirectly.

OVERVIEW

The present applicant has recognized, among other things, that other approaches to pressure sensing guidewires exhibit mechanical performance suitable for diagnostic assessment of coronary obstructions, but typically are not suitable for delivery of therapeutic devices. The present applicant has recognized that the other pressure sensing technology, namely piezoresistive or piezocapacitive silicon pressure sensors, and associated electrical cables, are relatively large compared to the size of the components of a typical therapy delivering guidewire. The present applicant has recognized that the incorporation of such other pressure sensing technology into a coronary guidewire substantially restricts the design of the mechanical components of the guidewire and results in significant compromises to the mechanical performance. The present applicant has recognized that a smaller pressure sensing technology, when incorporated into a contemporary coronary guidewire, would be advantageous in restoring the required mechanical performance requirements.

Optical fiber technology can be used in pressure sensors for oil discovery and production, as well as in larger diagnostic catheters for patients. The present applicant has recognized that telecommunication industry standard optical fiber would be too large to incorporate into high performance coronary guidewires. Accordingly, the present applicant has recognized, among other things, that miniaturization of the optical fiber and optical fiber based pressure sensor presents both a major challenge and a major advantage for incorporation into a coronary guidewire while minimizing the impact on the mechanical performance of the guidewire.

The present applicant has recognized, among other things, that the intrinsic sensitivity of an optical fiber sized for insertion into a body lumen may not be sufficient to generate an easily detectable signal within the range of pressures associated with a patient. The present applicant has recognized that miniaturization of the optical fiber can impart more flexibility into the fiber. This can be used to mechanically enhance the sensitivity of the fiber to pressure, such as with an extrinsic arrangement. The present applicant has recognized that using Fiber Bragg Gratings in the miniaturized optical fiber can provide a highly cost effective and readily manufacturable design. In addition, the present applicant has recognized that one or more other factors—such as the temperature coefficient of one or more Fiber Bragg Gratings (FBGs)—can be significantly higher than the intrinsic pressure sensitivity of the optical fiber. As such, a small drift in temperature within a patient can appear as a large pressure change artifact, which, in the context of pressure sensing, is unwanted and likely not acceptable due to the need for accurate pressure measurements. Accordingly, the present applicant has recognized, among other things, that it can be advantageous to provide an optical fiber pressure sensor guidewire that can include temperature calibration, compensation, or correction for an optical fiber pressure sensor, such as a Fiber Bragg Grating (FBG) arrangement for sensing pressure within a body lumen.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 7A-7C depict an example of a pressure sensor that can be used to implement various techniques of this disclosure.

FIGS. 8A-8C depict another example of a pressure sensor that can be used to implement various techniques of this disclosure.

FIGS. 13A-13C depict an example of a guidewire in combination with an optical fiber pressure sensor, in accordance with this disclosure.

FIGS. 14A-14C depict another example of a guidewire in combination with an optical fiber pressure sensor, in accordance with this disclosure.

FIGS. 15A-15C depict another example of a guidewire in combination with an optical fiber pressure sensor, in accordance with this disclosure.

FIGS. 21A-21D depict another example of a guidewire in combination with an optical fiber pressure sensor, in accordance with this disclosure.

FIG. 44A-44C depict another example of a guidewire in combination with an optical fiber pressure sensor.

FIGS. 45A-45B depict an example of a core wire that can be used in combination with an optical fiber pressure sensor.

DETAILED DESCRIPTION

Figure 1:
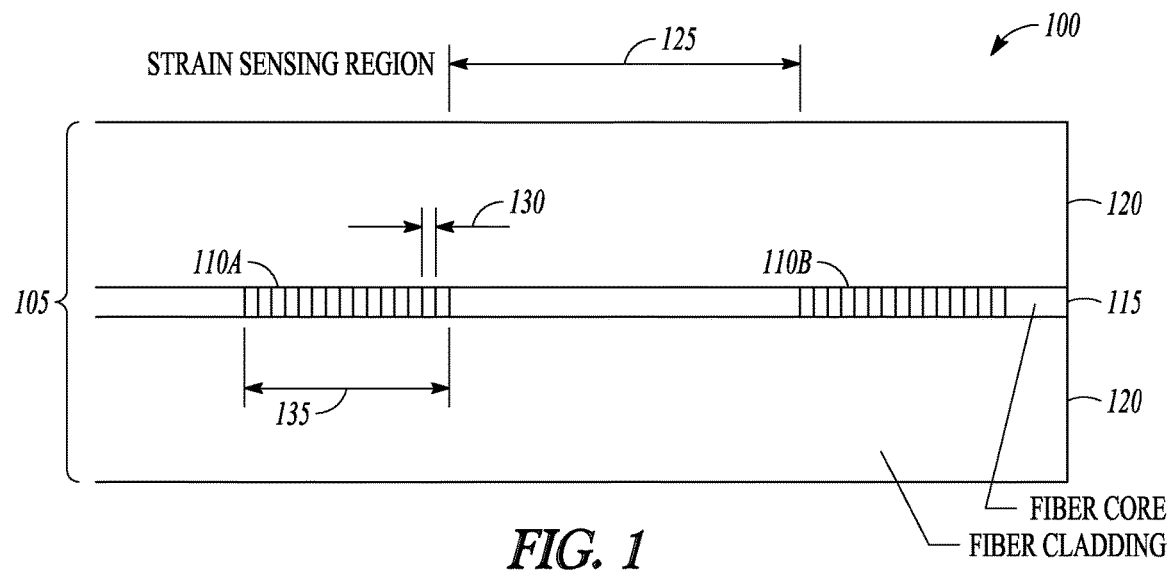
FIG. 1 is a cross-sectional side view illustrating generally, by way of example, but not by way of limitation, an example of an FBG pressure sensor in an optical fiber.

Before or during an invasive medical procedure, it can be desirable for a clinician, e.g., a physician, to take one or more pressure measurements from within a body lumen of a patient, e.g., a blood vessel, such as an artery or vein. For example, before implanting a stent at the site of an occlusion in a blood vessel, it can be desirable to determine the physiologic effect of the occlusion on the patient before making a decision whether to implant the stent. One way to determine the effect of the occlusion on the patient is to measure the drop in blood pressure across the occlusion, such as using a Fractional Flow Reserve (FFR) technique. Generally speaking, if there is more than a 20% drop in pressure across the occlusion during maximum blood flow, the patient can be considered a candidate for stent implantation. Otherwise, it can be preferable to treat the patient with a pharmaceutical regimen rather than implant a stent. Occlusions that look visibly similar, using an intravascular or other imaging modality, can be vastly different in terms of pressure drop across the occlusion. Therefore, an accurate measurement of pressure drop across an occlusion may help to tease out those occlusions that should be treated using a stent from those occlusions that are adequately treated by a pharmaceutical regimen.

As mentioned above, the present applicant has recognized, among other things, the advantages and desirability of miniaturization of an optical fiber and optical fiber based pressure sensor for incorporation into a coronary guidewire, which, in turn, can optionally be used for guiding a balloon catheter or other device for positioning and securing the stent at the desired location. An optical fiber pressure sensor based on FBG technology can have an intrinsic pressure sensitivity of about 0.00038 picometers (pm)/mmHg (about 0.02 pm/psi). Such an optical fiber pressure sensor based on FBG technology can have an intrinsic temperature sensitivity of about 10 pm/degree Celsius (° C.). The temperature sensitivity can increase if the optical fiber pressure sensor includes or is integrated or packaged with one or more materials having a higher coefficient of thermal expansion. The range of blood pressures in a patient is relatively low, e.g., about 0 millimeters of mercury (mmHg) to about 300 mmHg, and there is a need for high resolution within that range, e.g., 1-2 mmHg, where 51.7 mmHg equals 1 pound per square inch (psi), such as to adequately characterize the blood pressure drop across a blood vessel occlusion.

Based on these numbers, an uncompensated or uncorrected change in temperature of 0.1° C. can result in an equivalent intrinsic pressure drift of about 2632 mmHg or more than 1000 times the desired blood pressure measurement resolution. As mentioned above, when using an optical fiber pressure sensor capable of insertion into a body lumen of a patient, e.g., an animal such as a human, a small, uncompensated or uncorrected drift in temperature within the patient, e.g., as a result of an injected imaging contrast medium, can appear as an artifact that incorrectly indicates a large change in pressure. This can be due in part to the relatively low intrinsic sensitivity of the optical fiber pressure sensor to pressure and the relatively high intrinsic sensitivity to temperature of the optical fiber associated with the optical fiber pressure sensor. As such, a small, uncompensated drift in temperature can be unacceptable due to the need for accurate pressure measurements.

Using one or more techniques of this disclosure, a Fiber Bragg Grating (FBG) interferometer or other optical fiber pressure sensor guidewire can be temperature compensated, such as for permitting accurate pressure sensing within a body lumen. In addition, this disclosure describes techniques for increasing the overall sensitivity of an optical fiber pressure sensor guidewire, such as to generate an easily detectable blood pressure indicating output signal providing the desired resolution and accommodating the range of pressures associated with the patient.

It should be noted that the optical fiber described in this disclosure can have a diameter of between about 25 microns and about 30 microns. By way of comparison, a standard telecommunication optical fiber has a diameter of about 125 microns. This marked reduction in size can cause numerous challenges arising from the differences in the optics properties of such a drastically reduced size optical fiber.

FIG. 1 is a cross-sectional side view illustrating generally, by way of example, but not by way of limitation, an example of a strain-detecting or pressure-detecting optical FBG sensor 100 in an optical fiber 105. The FBG sensor 100 can sense pressure received from a nearby area, and can transduce the received pressure into an optical signal within the optical fiber 105. The FBG sensor 100 can include Fiber Bragg gratings 110A-B in an optical fiber core 115, such as surrounded by an optical fiber cladding 120. The gratings 110A-B can be separated by a strain or pressure sensing region 125, which, in an example, can be about a millimeter in length. In an example, strain or pressure can be sensed, such as by detecting a variation in length of the optical path between these gratings 110A-B.

A Fiber Bragg Grating can be implemented as a periodic change in the optical refractive index of a selected axial portion of the optical fiber core 115. Light of specific wavelengths traveling down such a portion of the core 115 will be reflected. The period (distance or spacing) 130 of the periodic change in the optical index can determine the particular wavelengths of light that will be reflected. The degree of optical refractive index change and the axial length 135 of the grating 110A-B can determine the ratio of light reflected to that transmitted through the grating 110A-B.

Figure 2:
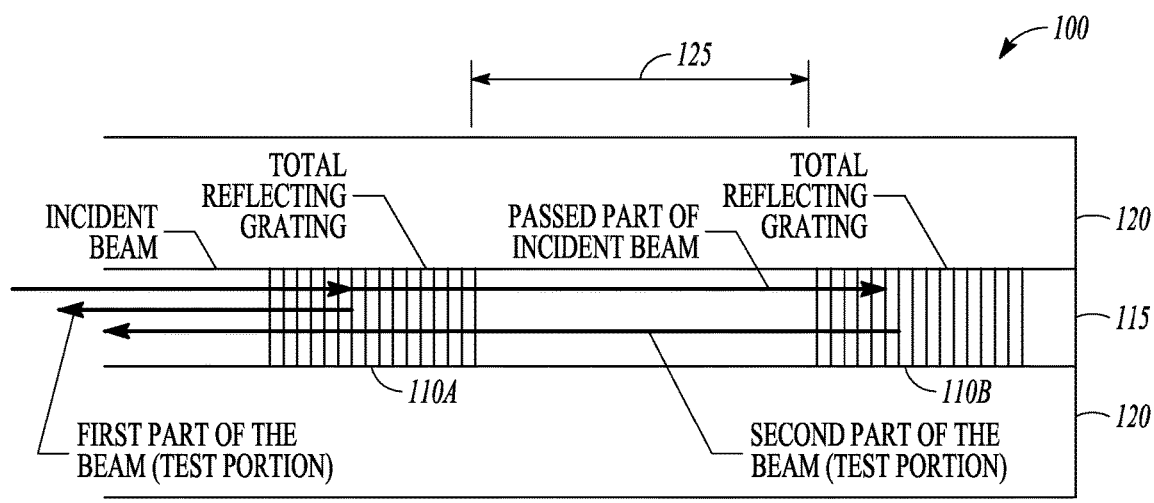
FIG. 2 is a cross-sectional side view illustrating generally, by way of example, but not by way of limitation, an example of an FBG grating interferometer sensor.

FIG. 2 is a cross-sectional side view illustrating generally, by way of example, but not by way of limitation, an operative example of an interferometric FBG sensor 100. The example of FIG. 2 can include two gratings 110A-B, which can act as mirrors that can both be partially reflective such as for a specific range of wavelengths of light passing through the fiber core 115. Generally, the reflectivity of each grating of a particular pair of gratings 110A-B will be substantially similar to the other grating in that particular pair of gratings 110A-B, but can differ between gratings of a particular pair of gratings 110A-B for particular implementations, or between different pairs of gratings 110A-B, or both. This interferometric arrangement of FBGs 110A-B can be capable of discerning the "optical distance or optical pathlength" between FBGs 110A-B with extreme sensitivity. The "optical distance or pathlength" can be a function of the effective refractive index of the material of fiber core 115 as well as the physical distance 125 between FBGs 110A-B. Thus, a change in the refractive index can induce a change in optical path length, even though the physical distance 125 between FBGs 110A-B has not substantially changed.

An interferometer, such as can be provided by the FBG sensor 100, can be understood as a device that can measure the interference between light reflected from each of the partially reflective FBGs 110A-B. When the optical path length between the FBG gratings 110A-B is an exact integer multiple of the wavelength of the optical signal in the optical fiber core 115, then the light that passes through the FBG sensor 100 will be a maximum and the light reflected will be a minimum, such that the optical signal can be substantially fully transmitted through the FBG sensor 100. This addition or subtraction of grating-reflected light, with light being transmitted through the optical fiber core 115, can be conceptualized as interference. The occurrence of full transmission or minimum reflection can be called a "null" and can occur at a precise wavelength of light for a given optical path length. Measuring the wavelength at which this null occurs can yield an indication of the length of the optical path between the two partially reflective FBGs 110A-B. In such a manner, an interferometer, such as can be provided by the FBG optical fiber pressure sensor 100, can sense a small change in distance, such as a change in the optical distance 125 between FBGs 110A-B resulting from a received change in pressure. In this manner, one or more FBG sensors can be used to sense one or more pressures within a body lumen of a patient. This arrangement is an example of an FBG Fabry-Perot interferometer, which can be more particularly described as an Etalon, because the physical distance 125 between the FBGs 110A-B is substantially fixed.

The sensitivity of an interferometer, such as can be included in the FBG sensor 100, can depend in part on the steepness of the "skirt" of the null in the frequency response. The steepness of the skirt can be increased by increasing the reflectivity of the FBGs 110A-B, which also increases the "finesse" of the interferometer. Finesse can refer to a ratio of the spacing of the features of an interferometer to the width of those features. To provide more sensitivity, the finesse can be increased. The higher the finesse, the more resonant the cavity, e.g., two FBGs and the spacing therebetween. The present applicant has recognized, among other things, that increasing the finesse or steepness of the skirt of FBG sensor 100 can increase the sensitivity of the FBG sensor 100 to pressure within a particular wavelength range but can decrease the dynamic range of the FBG sensor 100. As such, keeping the wavelength of the optical sensing signal within the wavelength dynamic range of the FBG sensor 100 can be advantageous, such as to provide increased sensitivity to pressure. In an example, a closed-loop system can monitor a representative wavelength (e.g., the center wavelength of the skirt of the filtering FBG sensor 100). In response to such information, the closed-loop system can adjust the wavelength of an optical output laser to remain substantially close to the center of the skirt of the filter characteristic of the FBG sensor 100, even as forces external to the optical fiber 105, such as bending and stress, can cause shifting of the center wavelength of the skirt of the filter characteristic of the FBG sensor 100.

In an example, such as illustrated in FIG. 2, the interferometric FBG sensor 100 can cause interference between that portion of the optical beam that is reflected off the first partially reflective FBG 110A with that reflected from the second partially reflective FBG 110B. The wavelength of light where an interferometric null will occur can be very sensitive to the "optical distance" between the two FBGs 110A-B. The interferometric FBG sensor 100 of FIG. 2 can provide another very practical advantage. In the example illustrated in FIG. 2, the two optical paths along the fiber core 115 are the same, except for the sensing region between FBGs 110A-B. This shared optical path can ensure that any optical changes in the shared portion of optical fiber 105 will have substantially no effect upon the interferometric signal; only the change in the sensing region 125 between FBGs 110A-110B is sensed. Additional information regarding FBG strain sensors can be found in U.S. Patent Application Publication No. 2010/0087732 to Eberle et al., which is incorporated herein by reference in its entirety, including its disclosure of FBGs and their applications.

Figure 3:
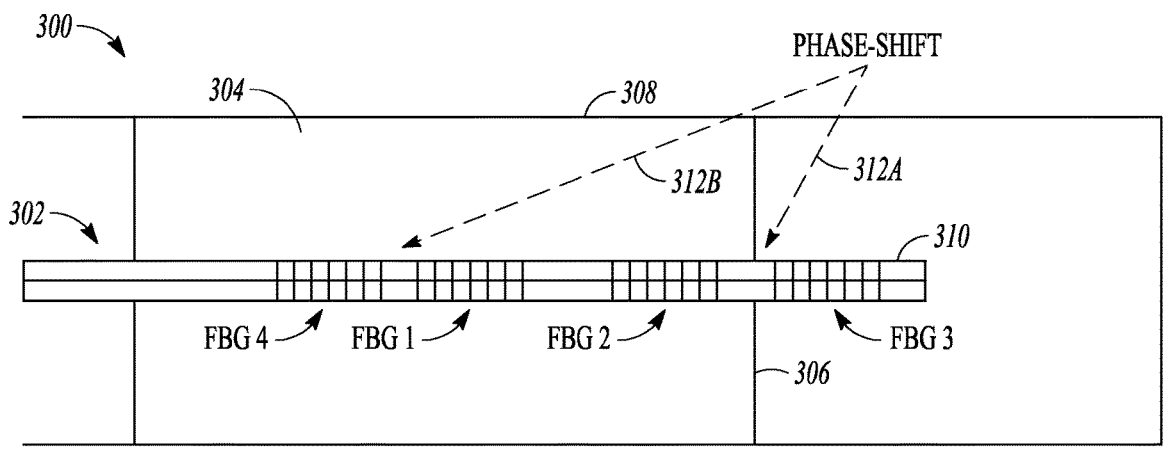
FIG. 3 is a conceptual diagram illustrating various example configurations FBG of an optical fiber pressure sensor, in accordance with this disclosure.

FIG. 3 is a conceptual diagram illustrating various examples of FBG configurations of an FBG optical fiber pressure sensor 300, in accordance with this disclosure. The FBG optical fiber pressure sensor 300 can include an optical fiber 302 that can extend longitudinally through a stiff, rigid, or solid mounting 304. As seen in FIG. 3, a portion of the optical fiber 302 extends beyond a distal end 306 of the mounting 304. The optical fiber 302 and the mounting 304 can be disposed within a housing 308. Using one or more techniques of this disclosure, such as shown and described in detail in this disclosure with respect to FIGS. 13-15, an optical fiber pressure sensor can include an optical fiber that can be combined with a guidewire, such as for diagnostic assessment of a coronary obstruction, for example.

As described in more detail below, two or more FBGs, e.g., FBGs 1-4, can be included in the FBG pressure sensor 300, such as for pressure sensing. One or more additional gratings can be included, and such additional one or more gratings can be insulated or isolated from influence caused by (1) bending (of the fiber) and/or (2) pressure. These insulated or isolated additional gratings can be arranged for providing one or more of temperature calibration, compensation, or correction. In an example, the additional grating(s) can provide an independent (of pressure and fiber bending) measure of temperature, such as for feedback to a temperature compensation scheme or method of an optical fiber pressure sensor 300. The optical fiber pressure sensor 300 can optionally include a sealed or other cavity (not depicted in FIG. 3), such as below a portion of the optical fiber 302, e.g., below FBG 3, which can amplify changes in pressure, or otherwise provide increased optical response to changes in pressure. Some example configurations that can include a sealed cavity are described in more detail below.

Figure 4A:
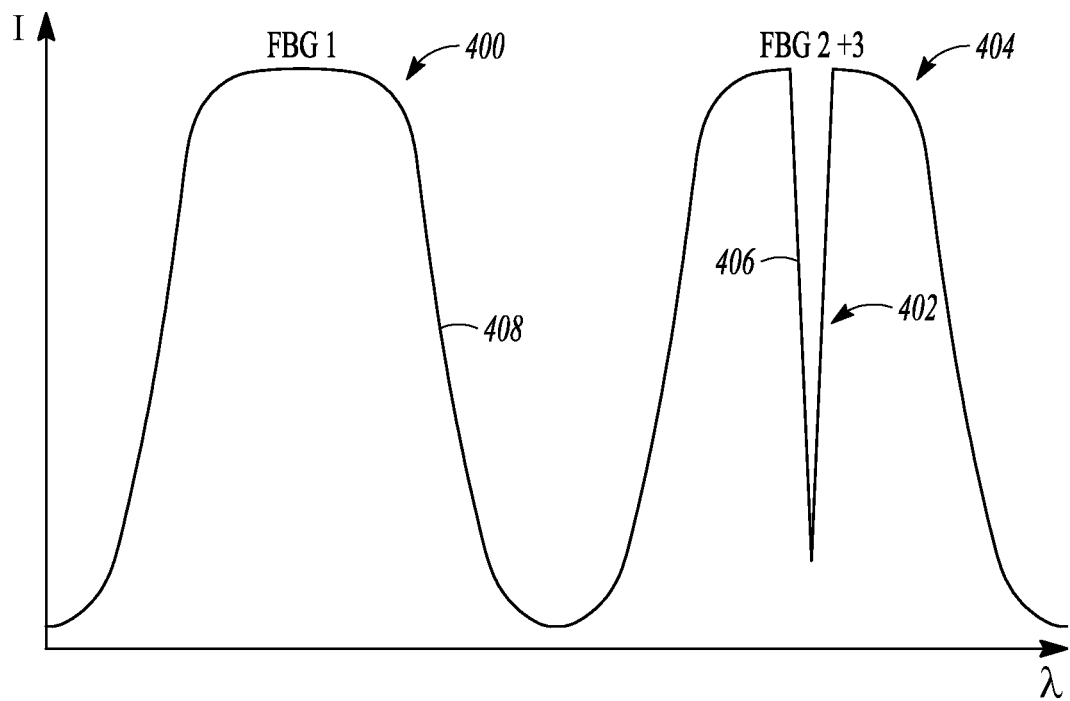
FIGS. 4A-4C depict various conceptual response diagrams related to the conceptual diagram of FIG. 3.

In FIG. 3, FBG 1 can be a FBG that produces a broad reflection band at the center of the spectrum of FBG 1, such as shown generally at 400 in the response diagram depicted in FIG. 4A, in which the x-axis represents wavelength and the y-axis represents the intensity of the reflected light. FBG 2 and FBG 3, although depicted and referred to as separate gratings, can represent a single FBG that can be split into two identical, smaller FBGs and separated by a small phase difference (or phase-shifted) of 180 degrees, for example.

For example, the phase shift could be built into a phase mask that is used to write the gratings onto the fiber, e.g., an electron beam generated phase mask. Illumination of the phase mask can result in a phase shift. In another example, a first grating can be written onto the fiber via a phase mask. Then, the phase mask can be moved by a distance equivalent to a 180 degree phase shift, for example, and a second grating can be written onto the fiber.

The reflections from FBG 2 interfere with the reflections from FBG 3 because of the phase shift between FBG 2 and FBG 3, shown as a phase shift region 312A in FIG. 3. As a result, a narrow transmission notch 402 is created within the reflection band shown generally at 404 in the wavelength response diagram depicted in FIG. 4A.

In an example, pressure changes can be detected by the optical fiber pressure sensor 300, e.g., within a patient's body, such as by detecting or amplifying the phase-shift between two FBGs, e.g., FBG 2 and FBG 3. This technique is in contrast to optical pressure sensing techniques that measure the shift in wavelength of the FBG itself. Using various techniques of this disclosure, the phase-shift between FBGs can be modified rather than a wavelength shift of the FBG itself.

As seen in FIG. 3, FBG 3 can extend distally outward beyond the distal end 306 of the mounting 304. A change in pressure can cause the distal portion 310 of the optical fiber 302 to bend slightly against the distal end 306 of the mounting 304, which, in turn, can cause the distal end 306 to mechanically act upon the phase-shift region 312A between FBG 2 and FBG 3. The mechanical forces acting upon the phase-shift region 312A between FBG 2 and FBG 3 can concentrate a stress in the phase-shift region 312A of the optical fiber 302. The concentrated stress in the phase-shift region 312A changes the refractive index of the optical fiber 302 in the stressed region, which, in turn, can alter, or amplify, the phase relationship between FBG 2 and FBG 3. The change in phase-shift between FBG 2 and FBG 3 can be quantified and the change in pressure can be determined from the quantified phase-shift.

For example, as described in more detail below, a wavelength of a narrow band laser (in relation to the wavelength response of FBGs 2 and 3) can be locked on a point on a slope 406 of the narrow transmission notch 402 in FIG. 4A, e.g., at about 50% of the depth of the notch 402. As the pressure changes, the notch 402 shifts and, consequently, the point on the slope 406 shifts. A tracking circuit can then track the point on the slope 406, and a phase-shift can be determined from its change in position. The intensity of reflected light will be modified when the notch 402 moves. In the example in the diagram, if the notch 402 moves downward in wavelength, then the intensity of the signal reflected will increase. If the notch 402 moves upward in wavelength, then the intensity of the signal reflected will decrease. If it is chosen that the laser wavelength would be on the opposite side of the notch 402, then the effect would be reversed.

As indicated above, one or more external factors such as the temperature coefficient of one or more Fiber Bragg Gratings (FBGs) can be significantly higher than the intrinsic pressure sensitivity of the optical fiber pressure sensor that can include such FBGs. As such, a small drift in temperature within a patient can spuriously appear as a large change in pressure. Such a temperature-induced artifact in the pressure response signal may be unacceptable due to the need for accurate pressure measurements. The present applicant has recognized, among other things, that it can be advantageous to provide the optical fiber pressure sensor guidewire of this disclosure with a temperature compensated Fiber Bragg Grating (FBG) arrangement, such as for accurately sensing pressure within a body lumen, for example.

The conceptual diagram of FIG. 3 can be used to describe several different configurations for a temperature compensated FBG optical fiber pressure sensor 300. Examples of more detailed configurations are shown and described below with respect to FIGS. 7-10 and FIG. 12.

In a first example of a configuration, a FBG optical fiber pressure sensor 300 can include FBGs 1-3 (FBG 4 need not be included). FBGs 2 and 3, which can be configured to operate at the same wavelength (e.g., a first wavelength between about 1000 nanometers (nm) and about 1700 nm), can form a phase-shift structure that can be used to sense pressure, such as described in detail above. To recap, a concentration in stress in the phase-shift region between the two gratings (e.g., FBG 2 and FBG 3), as a result of the bending of the optical fiber 302 changes the refractive index of the optical fiber 302 in the phase-shift region. The change in the refractive index of the optical fiber 302 in the phase-shift region can alter the phase relationship between FBG 2 and FBG 3, which can be quantified, and the change in pressure can be determined from the quantified phase-shift. The phase-shift, however, is not compensated for temperature, which may not be acceptable, as explained above.

FBG 1 can be configured to be substantially independent of pressure, such as by locating it within the stiff, rigid, or solid mounting 308. Therefore, FBG 1 can be used to measure ambient temperature, such as to provide a temperature compensated optical fiber pressure sensor. FBG 1 can be configured to operate at a substantially different wavelength than that of FBGs 2 and 3 (e.g., a second wavelength between 1000 nanometers (nm) and 1700 nm). In this manner, FBG 1 has no interaction with FBGs 2 and 3. As such, FBG 1 can provide a measure of ambient temperature that is independent of pressure variations. In a manner similar to that described above with respect to tracking the change in position of the notch 402 of FIG. 4A, a wavelength of a narrow band laser (in relation to the response of the FBG 1) can be locked on a point on a slope 408 of the response of FBG 1 in FIG. 4A, e.g., at about 50% of the depth of the response. The wavelength of the locked point on the slope 408 shifts as the temperature changes. A tracking circuit can then track the locked point on the slope 408 and a change in ambient temperature can be determined from its change in position.

In order to generate a pressure signal that is ambient temperature compensated, the signal generated by FBG 1 can be used as a reference to null a shift in temperature. A controller circuit can be configured to control subtraction of the temperature reference signal (from FBG 1) from the temperature and pressure signal (from FBGs 2 and 3), such as to generate a temperature compensated pressure signal. An example of a temperature compensation technique is described in more detail in this disclosure, such as with respect to FIG. 5.

In a second example of a configuration, the FBG sensor 300 can include an optical fiber, a stiff, rigid, or solid mounting, a housing, and FBGs 1-3 (FBG 4 need not be included). FBGs 1-3 can be positioned very close to each other and can thus form a very compact structure. FBGs 2 and 3, which can be configured to operate at the same wavelength (e.g., a first wavelength between 1000 nm and 1700 nm), can form a phase-shift structure that can be used to sense pressure. The phase shift between FBGs 2 and 3 can result in a signal that changes with pressure and temperature.

FBG 1 can be configured to operate at a similar, but slightly different, wavelength than that of FBGs 2 and 3 (e.g., a second wavelength near the first wavelength of FBGs 2 and 3 and between 1000 nm and 1700 nm). In this manner, FBG 1 can form a resonant feature with FBGs 2 and 3 at a slightly different wavelength. FBG 1 can result in a signal that changes with respect to temperature changes.

Figure 4B:
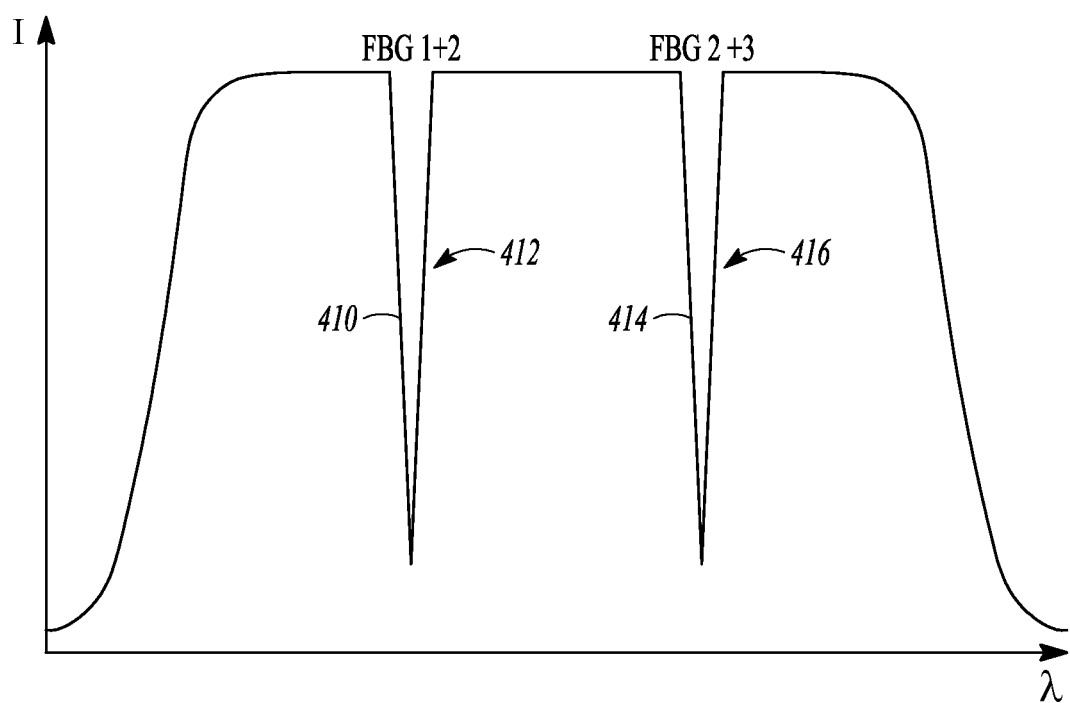

A conceptual illustration of the response of FBGs 1-3 is depicted in FIG. 4B, where the x-axis represents wavelength and the y-axis represents the intensity of the reflected light. Again, the techniques of this disclosure need not sense a shift in the wavelength of the gratings, but can instead sense a change in the phase between the gratings. The temperature compensating element, e.g., FBG 1, is in resonance with part of the pressure sensing structure, e.g., FBGs 2 and 3. As such, FBG 1 can be linked to the pressure sensing structure rather than being an independent element. Such a configuration can provide a compact structure.

Similar to the first example of a configuration, such as to generate a pressure signal that is temperature compensated, the signal generated by FBG 1 can be used as a reference, such as to null a shift in temperature. A slope 410 of the notch 412 and a slope 414 of the notch 416 can each be tracked and used to determine changes in temperature and pressure, such as based on their respective changes in position. A controller circuit can be configured to control the subtraction of the temperature reference signal (e.g., from FBG 1) from the temperature and pressure signal (e.g., from FBGs 2 and 3) such as to generate a temperature compensated pressure signal.

In a third example of a configuration, the FBG sensor 300 can include an optical fiber, a stiff, rigid, or solid mounting, a housing, and FBGs 1-4. FBGs 2 and 3, which can be configured to operate at the same wavelength, can form a first phase-shift structure that can be used to sense pressure. The phase shift between FBGs 2 and 3 can result in a signal that changes with pressure or temperature, or both.

FBGs 1 and 4, which can be configured to operate at the same wavelength, can form a second phase-shift structure that can be used to sense temperature. The reflections from FBG 4 interfere with the reflections from FBG 1 because of the phase shift between FBG 4 and FBG 1, shown as a phase shift region 312B in FIG. 3. The phase shift between FBGs 1 and 4 can result in a signal that changes with temperature and that is independent of pressure.

Figure 4C:
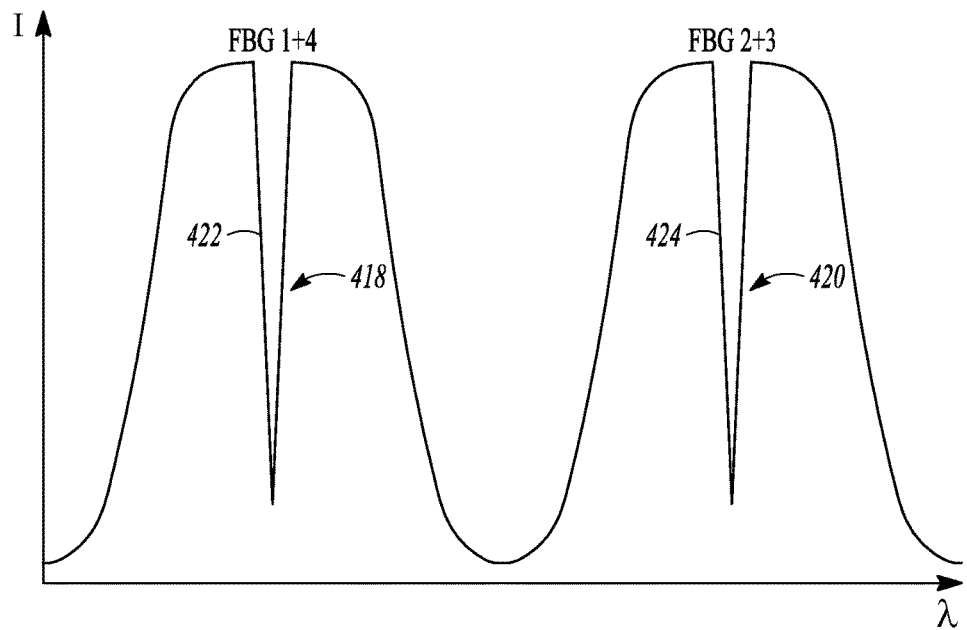

A conceptual illustration of the response of FBGs 1-4 of the third example of a configuration is depicted in FIG. 4C, where the x-axis represents wavelength and the y-axis represents the intensity of the reflected light. As seen in FIG. 4C, the response includes two notches 418, 420. The third example of a configuration can provide more accurate measurements than the first example of a configuration because the notches 418, 420 are generally more sensitive to any changes than responses without notches, e.g., the response 400 in FIG. 4A.

Similar to the first and second examples of configurations, in order to generate a pressure signal that is temperature compensated, the signal generated by FBGs 1 and 4 can be used as a reference, such as to null a shift in temperature. A slope 422 of the notch 418 and a slope 424 of the notch 420 can each be tracked and used to determine changes in temperature and pressure based on their respective changes in position. A controller circuit can be configured to control subtraction of the temperature reference signal (e.g., from FBG 1) from the temperature and pressure signal (e.g., from FBGs 2 and 3), such as to generate a temperature compensated pressure signal.

Using any one of the three examples of configurations described above, an optical fiber pressure sensor can be provided that can be suitable for delivery within a body lumen, e.g., for diagnostic assessment of coronary obstructions. In addition, any one of the three examples of configurations can compensate for temperature drift and can be fitted to a guidewire, such as for insertion into a body lumen of a patient. In any of the three examples the wavelength of the FBGs used for temperature calibration, compensation, or correction can be above or below the wavelength of the FBGs used for the pressure sensing.

Again, FIG. 3 is for conceptual purposes only and this disclosure is not limited to the three example configurations described above with respect to FIG. 3. Other FBG configurations to sense pressure and compensate for temperature drift are possible, examples of which are described in more detail below.

In addition, as described in more detail below, various techniques are disclosed for increasing the intrinsic sensitivity of an optical fiber pressure sensor, such as to generate an accurate output signal within the range of pressures associated with a patient. Generally speaking, these techniques can include focusing a response of a pressure sensor membrane into a smaller area, such as to increase the optical response to the received pressure, e.g., from pressure waves.

FIGS. 4A-4C depict various wavelength response diagrams related to the conceptual diagram and examples of configurations described above with respect to FIG. 3. In FIGS. 4A-4C, the x-axis represents wavelength and the y-axis represents the intensity of the reflected light. The response diagrams were described above in connection with the examples of configurations of FIG. 3.

Figure 5:
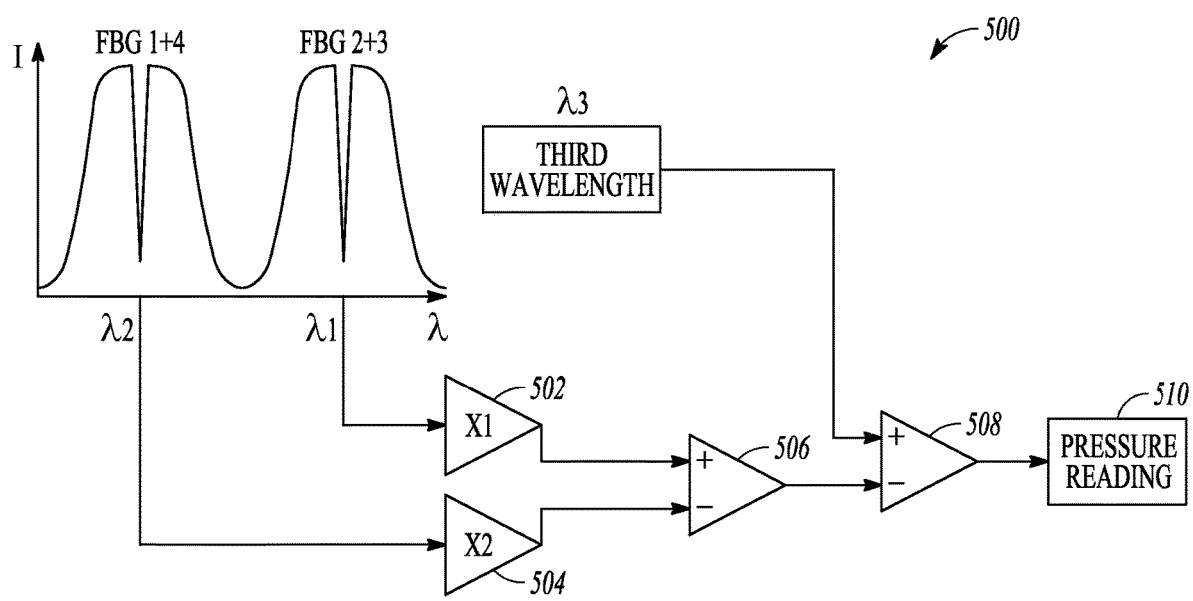
FIG. 5 is a block diagram of an example of an ambient temperature compensation technique in accordance with this disclosure.

FIG. 5 is a block diagram of an example of an ambient temperature compensation technique that can be used to implement one or more techniques of this disclosure. Although the example of a configuration of FIG. 5, shown generally at 500, will be particularly described with specific reference to the third example of a configuration described above, it is applicable to each of the example configurations described in this disclosure.

Initially, the optical fiber pressure sensor 300 of FIG. 3 can be calibrated, such as to ascertain the relative coefficients of temperature and pressure for the sensor. The magnitudes of these coefficients can be stored in a memory device. A controller circuit can be configured such that, during operation, it can read the coefficients from the memory device and apply the pressure coefficient as a first coefficient X1 and the temperature coefficient as a second coefficient X2.

As described above, a first wavelength of a narrow band laser (in relation to the response of FBGs 1 and 4) can be locked on a point on the slope 422 of the narrow transmission notch 418 in FIG. 4C, e.g., at about 50% of the length of the notch 418. A second wavelength of a narrow band laser (in relation to the response of FBGs 2 and 3) can be locked on a point on the slope 424 of the narrow transmission notch 420 in FIG. 4C, e.g., at about 50% of the depth of the notch 420.

As the pressure changes, the notch 420 shifts and, consequently, the point on the slope 424 shifts. The tracking circuit can be configured to then track the point on the slope 424. The magnitude of the change in wavelength, shown as $\lambda 1$ in FIG. 5, can be input into a first multiplier 502 and multiplied by the pressure coefficient X1. Similarly, as the ambient temperature of the pressure sensor changes, the notch 418 shifts and, consequently, the point on the slope 422 shifts. A tracking circuit can then track the point on the slope 422. The magnitude of the change in wavelength, shown as $\lambda 2$ in FIG. 5, can be input into a second multiplier 504 and multiplied by the ambient temperature coefficient X2. Similarly, The outputs of the multipliers 502, 504 can be input into a first comparator 506, which can subtract any ambient temperature drift from the pressure measurement. In this manner, ambient temperature nulling techniques can be used to provide accurate pressure measurements.

Also in accordance with this disclosure, a third wavelength that can be close in magnitude to $\lambda 1$ or $\lambda 2$ but not in resonance with the phase shift feature can be used to monitor a total insertion loss of the system, e.g., from any bending, insertion of the optical fiber into a connector, etc. The insertion loss is generally a static number. During operation, the controller circuit can transmit the third wavelength $\lambda 3$, which can be input into a second comparator 508 along with the pressure measurement output from a first comparator 506, and the second comparator 508 can compensate the pressure measurement for any changes in insertion loss to produce a final pressure reading 510 for the optical fiber pressure sensor.

Pressure sensors constructed using optical fibers can suffer from significant pressure drift, due at least in part to the low intrinsic sensitivity of optical fibers (e.g., optical refractive index, mechanical size, etc.) to pressure. This is especially true for optical fiber pressure sensors that are designed for low pressure applications, such as sensing the pressure within the human body.

As mentioned above, when using an optical fiber pressure sensor capable of insertion into a body lumen of a patient, e.g., an animal such as a human, a small, uncompensated or uncorrected drift in temperature within the patient, e.g., as a result of an injected imaging contrast medium, can appear as an artifact that incorrectly indicates a large change in pressure. This can be due in part to the relatively low intrinsic sensitivity of the optical fiber pressure sensor to pressure and the relatively high intrinsic sensitivity to temperature of the optical fiber associated with the optical fiber pressure sensor. As such, a small, uncompensated drift in temperature can be unacceptable due to the need for accurate pressure measurements.

As described in more detail below with respect to FIGS. 6A-6B, one or more techniques of this disclosure are described that can remove and/or compensate for the effects of temperature drifts and other deleterious effects that might compromise the accuracy of the pressure reading. For example, polarization scrambling techniques, ambient temperature nulling techniques, laser tracking techniques, and laser temperature monitoring techniques can be used in combination to correct for temperature drifts that can affect the accuracy of the pressure readings.

Figure 6A:
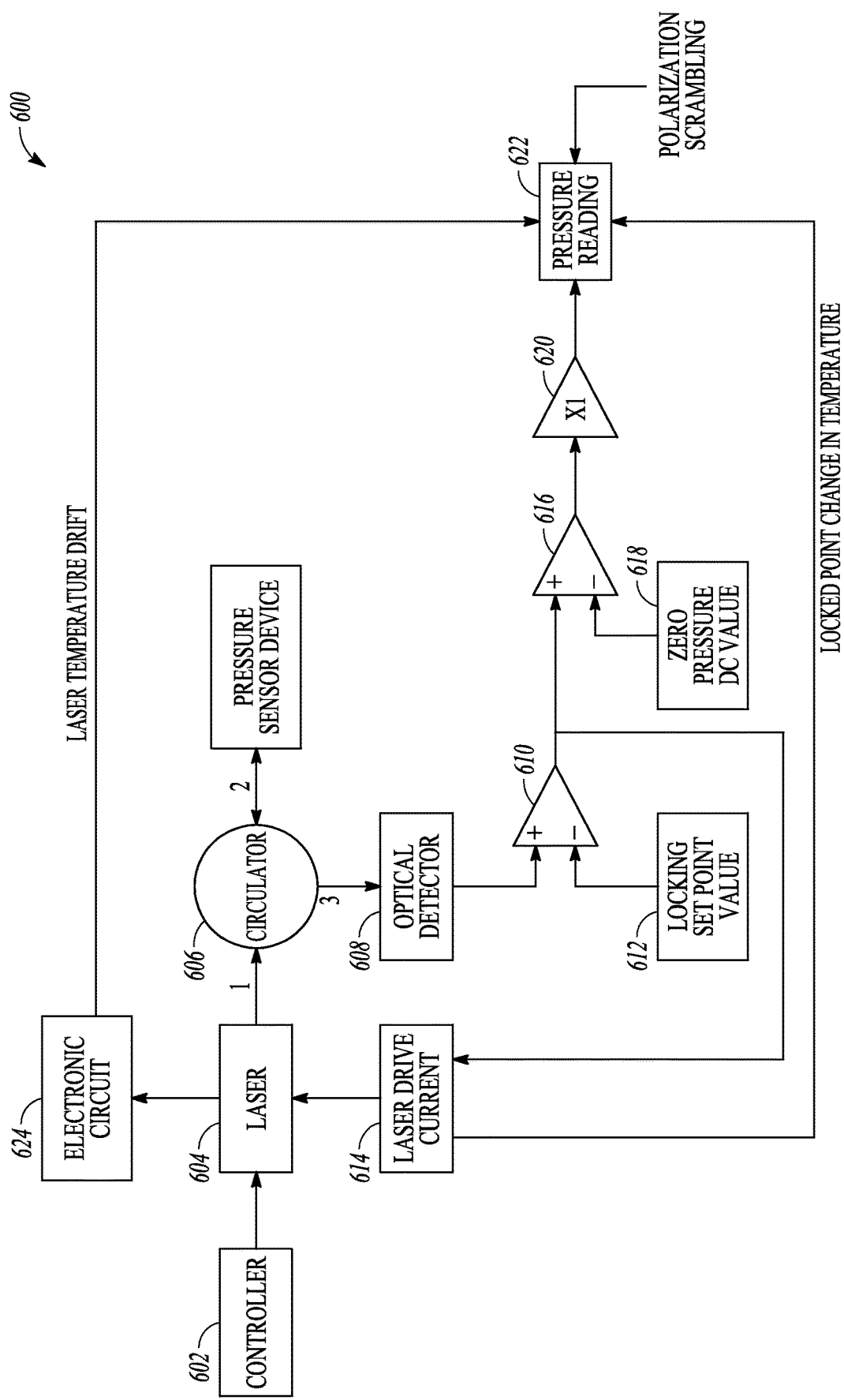
FIG. 6A is a block diagram of an example of a laser tracking system, in accordance with this disclosure.

FIG. 6A is a block diagram of an example of a laser tracking system, shown generally at 600, in accordance with this disclosure. A controller circuit 602 can be configured to control a laser 604 to generate and transmit the light from a narrow band laser into a first port (e.g., port 1) of a circulator 606. The circulator 606 can route the light out a second port (e.g., port 2) toward the optical fiber pressure sensor. The controller circuit 602 can be configured to set the wavelength of the laser on a point on a slope of a notch in the wavelength response of an FBG, such as described above. Any light reflected back from the optical fiber pressure sensor can enter the second port (e.g., port 2) of the circulator 606 and can be routed out a third port (e.g., port 3) and received by an optical detector 608.

As indicated above, laser tracking techniques can be used to correct for temperature drift. In accordance with this disclosure, the laser 604 can be actively locked at a position on a slope of a transmission notch, e.g., slope 406 of the notch 402 of FIG. 4A. Then, the system 600 can measure the change in wavelength and, in response, alter the laser's operating characteristics, e.g., drive current.

In the system 600 of FIG. 6A, a first comparator 610 can be used to provide laser tracking. The optical power of the reflected signal, which is output by the optical detector 608, can be a first input to a first comparator 610. A locking set point value 612 can be a second input to the first comparator 610. The first comparator 610 can compare the two inputs and then output a value that can be applied as an input to a laser drive current control 614 that can modulate the drive current of the laser 604. In this manner, the configuration of FIG. 6A can provide a locking loop to maintain a set point on the slope of a notch, for example.

In one example implementation, during initial setup a user can adjust the conditions of the laser 604 so that the wavelength of the laser 604 is slightly greater than the wavelength of the transmission notch. The user can adjust the wavelength of the laser 604 by adjusting the drive current of a thermoelectric cooler (TEC) of the laser 604 (large shifts in wavelength), which can alter the temperature of a submount of the laser 604, or adjust the drive current of the laser 604 itself (small shifts in wavelength).

Once the initial setup of the laser 604 is complete, the user can initiate the tracking techniques of this disclosure. The tracking techniques begin to reduce the drive current to the laser 604, which, in turn, decrease the wavelength of the laser. More particularly, as the wavelength of the laser 604 decreases toward the wavelength of the transmission notch, the comparator 610 compares the signal from the optical detector 608 and the locking set point value 612. If the signal from the optical detector 608 is higher than the locking set point value 612, the drive current of the laser 604 can be reduced via feedback from the comparator 610 to the laser drive current control 614. In some examples, reducing the laser drive current by 0.25 milliamps (mA) can shift the wavelength by 1 pm, where the coefficient of the laser 604 is about 4 pm per 1 mA of drive current.

During operation, the wavelength of the locked point on the slope can shift as the ambient temperature changes. If the wavelength of the transmission notch increases or decreases, the system 600 increases or decreases, respectively, the drive current of the laser 604 in order to track the transmission notch. As indicated above, the laser 604 can, for example, be locked on a point on a slope of the narrow transmission notch at about 50% of the depth of the notch 402. These tracking techniques can track the position of the locked point on the slope and a change in temperature can be determined from the change in position. The determined change in temperature can be an input into an algorithm executed by a pressure reading module 622, which can use the determined change in temperature to calculate an accurate pressure reading. The pressure reading module 622 can be, for example, machine or computer-implemented at least in part. For example, the controller 602 can execute instructions encoded on a computer-readable medium or machine-readable medium that implement the techniques and algorithms ascribed to the pressure reading module 622.

One advantage of tracking the shift in wavelength of the FBG sensor by modulating the drive current of the laser is that it can linearize the response of the circuit and can be more forgiving of different power levels. That is, regardless of the built in or fixed insertion loss of the pressure sensor, which can vary by construction variables or variations in connecting in-line optical connectors, the amount by which the drive current will change for a given wavelength shift will be constant. Optical fiber pressure sensors that utilize a change in power to demodulate the signal are sensitive to changes in insertion loss. By knowing the shift in laser wavelength for a given drive current change, the current reading can be converted to a wavelength and hence to a pressure reading.

Optical sensing schemes exist that directly measure the change in wavelength of the sensor response. In one example, the sensor can be illuminated with broadband light and the spectral response can be measured with an Optical Spectrum Analyzer (OSA). This is not feasible for this application as the update times can be too slow and the required wavelength precision is beyond this type of instrument. Alternatively, techniques exist that measure the change in intensity of the optical power as the laser tracks up and down the slope of the FBG sensor. One disadvantage of this techniques, however, is that the power response will be non-linear for large excursions as the laser approaches the top of the filter (lower slope) and the bottom of the filter (higher slope). Without compensation this technique can yield inaccurate results.

Continuing with the description of FIG. 6A, the output of the first comparator 610 can be applied as a first input to a second comparator 616. A zero pressure DC value 618 can be applied as a second input to the second comparator 616, which can subtract the initial DC value and output a zero pressure reading. The outputted zero pressure reading from the second comparator 616 can be multiplied at a multiplier 620 by a coefficient of wavelength shift with the drive current that results in an output of an actual wavelength shift. The outputted actual wavelength shift can then be converted to a pressure reading at 622.

As indicated above, laser temperature monitoring techniques can be used to correct for temperature drifts that can affect the accuracy of the pressure readings. The lasers used to implement the various techniques described in this application have a wavelength dependency on the temperature at which they operate. A typical laser will have a wavelength dependency on operating temperature of 100 pm per degree Celsius (° C.). A well controlled laser may have temperature stability of 0.01° C. giving a wavelength drift of 1 pm. As indicated above, however, a shift of 1 pm is equivalent to a very large pressure difference and, as such, should be accounted for in the final pressure reading.

Rather than stabilize the laser temperature to the degree required, which can increase the complexity and expense of the system 600, this disclosure describes techniques that can accurately monitor the temperature through a thermistor that is built-in to the submount of the laser 604 and that can apply this temperature information to a correction algorithm for the final pressure reading 622. To accurately monitor the temperature through the thermistor, the system 600 of FIG. 6A can include an electronic circuit 624, e.g., outside the optical system, that is configured to measure the voltage across the thermistor of the submount of the laser 604. The electronic circuit 624 can include an amplifier that can amplify the voltage signal with high enough gain that to resolve temperature changes on the order of $1/1000^{th}$ of a degree Celsius. These changes are on the order of hundreds of microvolts ($\mu V$). As such, it can be desirable to use high quality circuits composed of instrumentation amplifiers, for example.

In one example implementation, rather than amplifying the voltage across the thermistor, the electronic circuit 624 can subtract an offset voltage from the voltage across the thermistor, e.g., the operating voltage of the laser, before amplification. Then, the electronic circuit 624 can amplify the resulting voltage value, which is close to zero. In this manner, the electronic circuit 624 allows small changes in the temperature of the laser to be determined. The temperature change can be converted to wavelength and then to the equivalent pressure, which can then be used to determine the true pressure reading at 622.

The output from the laser, e.g., laser 604, can have a strong degree of linear polarization at the exit from the laser package. It is technically possible to preserve this linear polarization by using polarization maintaining fiber and components along the entire optical path to the FBGs. If the polarization is preserved such that the light incident upon the FBGs is aligned preferentially with a particular birefringent axis, then the response of the light to the FBGs would not be affected by the birefringence. Unfortunately, preserving the polarization in this manner is both complex and expensive.

In the absence of polarization maintaining measures, the light from the laser can arrive at the FBGs with any state of polarization depending on the nature of the optical path through which the light has travelled. Significant bending or twisting of the fiber and the birefringent nature of any components through which the light has travelled can alter the state of polarization (SOP). Although the SOP that arrives at the FBGs is not controlled, it nevertheless can have a high degree of polarization (DOP) as this characteristic is very difficult to fully randomize. A high DOP means the exact interaction of the light and the birefringent axes of the FBGs can change if there are perturbations to the system, such as bending of the guidewire during a procedure. For this reason, the system 600 of FIG. 6A can utilize polarization scrambling techniques to overcome the effects of birefringence and determine a true pressure reading. The polarization scrambling techniques scramble or average a range of polarization states so the final result is not biased to any given combination of birefringent axis of the FBG and incident polarization state.

Optical fiber pressure sensors such as the FBGs of this disclosure are subject to the effects of birefringence in the optical fiber, due to the physical imperfections of the fiber. With birefringence, different polarizations of light can have slightly different effective optical refractive indices. An effective index of the fiber that is different for different polarizations can result in a slightly different Bragg wavelength. A different Bragg wavelength can result in the appearance of movement of the point on the slope of the transmission notch at which the laser is locked. In reality, however, the point may not have moved at all.

A typical optical fiber can have birefringence on the order of $2.5 \times 10^{-6}$, which translates to a wavelength shift between the most different polarizations of 4 pm. A 4 pm wavelength shift would be equivalent to a relatively massive pressure change and, as such, should be accounted for in the final pressure reading.

The exact wavelength of the FBG can be determined by a combination of the refractive index of the medium and the physical spacing of the planes or fringes that make up the FBG, as in the following equation:

$$l_B = 2n_e L,$$

where $l_B$=Bragg wavelength, $n_e$=effective refractive index, and L=spacing of fringes.

The polarization scrambling techniques of this disclosure can be implemented by sweeping a series of "optical waveplates" through a pseudo-random pattern with sufficient frequency that the desired signal will be averaged satisfactorily. Optical waveplates are devices that can alter the state of polarization. In order to measure a typical cardiovascular pressure profile with a heart rate of 0 beats per minute to 200 beats per minute, scrambling techniques can average at a rate that is sufficient to capture the dynamic profile, e.g., an effective frequency of several hundred hertz.

In the system 600 of FIG. 6A, the optical waveplates can be physically located between where the laser beam exits laser 604 and the FBGs of the optical fiber pressure sensor. In one example, an optical waveplate can be formed by wrapping a portion of the optical fiber around a piezoelectric material and by stretching the fiber upon application of a voltage to the piezoelectric material. In another example, an optical waveguide can be used to form an optical waveplate. The application of a voltage across electrodes built into the optical waveguide can result in the change of the refractive index.

Using the polarization scrambling techniques of this disclosure, it is not necessary to know the levels or patterns of birefringence in the system because the polarization controlling techniques do not rely upon feedback. Instead, the polarization scrambling techniques rely on an averaged polarization that is achieved by sweeping through as many available polarization states to get an average polarization value so the final result is not biased to any given combination of birefringent axis of the FBG and incident polarization state. Additional information regarding how the polarization scrambling techniques are used to determine a true pressure reading are disclosed in U.S. Provisional Application No. 61/709,700, titled "POLARIZATION SCRAMBLING FOR INTRA-BODY FIBER OPTIC SENSOR", by Howard Rourke, et al. and filed on Oct. 4, 2012, the entire content of which being incorporated herein by reference.

Figure 6B:
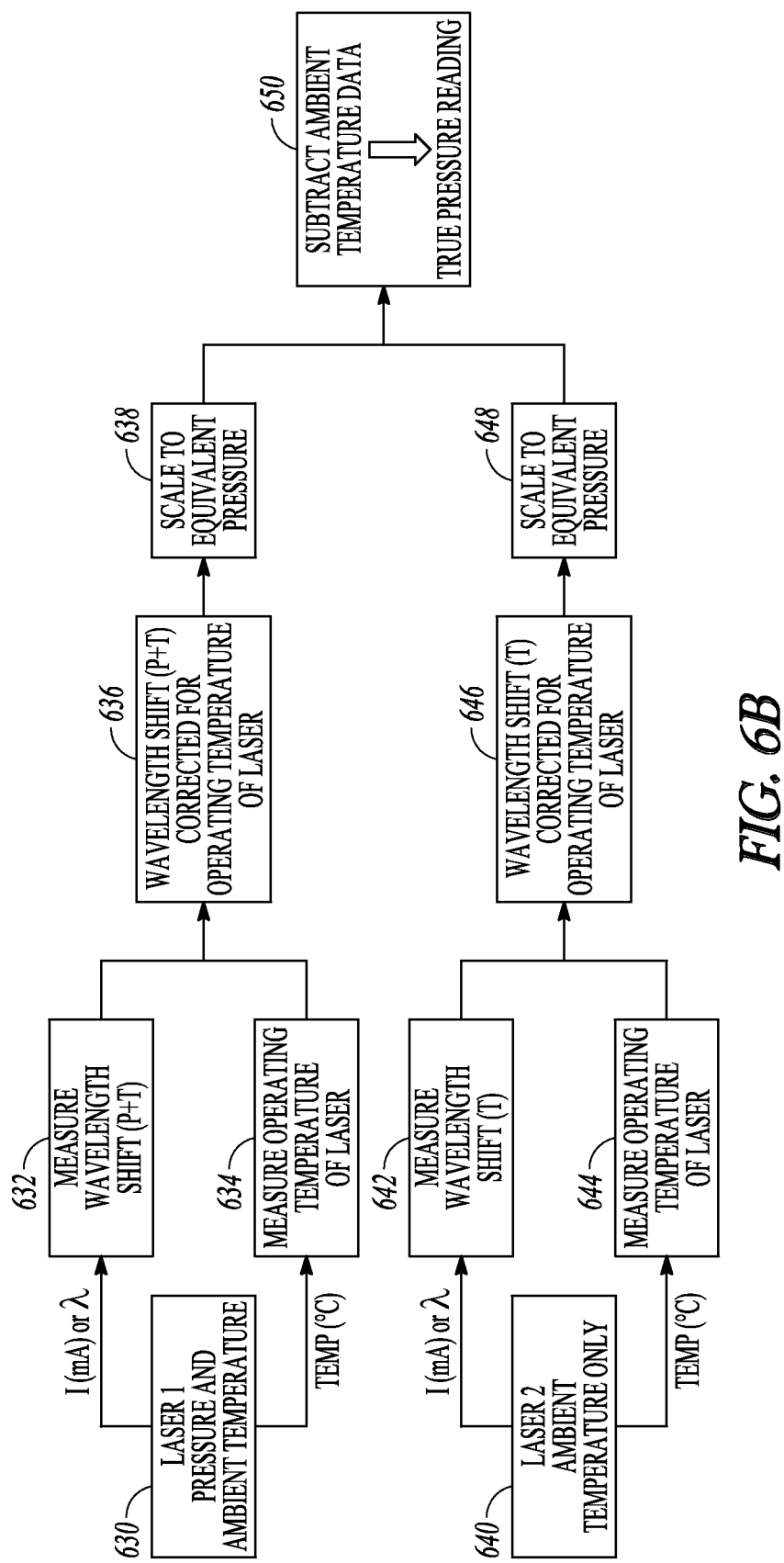
FIG. 6B is a block diagram of an example of a temperature compensation technique in accordance with this disclosure.

FIG. 6B is a block diagram of an example of a temperature compensation technique in accordance with this disclosure. As described above, in order to determine an accurate pressure reading, both the ambient temperature of the optical fiber pressure sensor and the temperature drift of the laser should be accounted for in the final pressure reading at 622 of FIG. 6A. In FIG. 6B, a first laser 630 can be locked onto a phase-shift region, e.g., phase-shift region 312A between FBG 2 and FBG 3 of FIG. 3. This phase-shift region, however, is not compensated for the ambient temperature of the pressure sensor and, as such, reacts to both pressure and temperature. Using either a measurement of the change in drive current of the laser, e.g., in milliamps, or a measurement of the change in wavelength, the controller 602 of FIG. 6A can determine the shift in wavelength at 632. Further, using the techniques described above, the controller 602 can determine the operating temperature of the first laser 630 at 634 by measuring the voltage across the submount thermistor via the electronic circuit 624 of FIG. 6A. The controller 602 can correct the determined shift in wavelength for the operating temperature of the first laser 630 by subtracting the determined operating temperature of the first laser 630 from the shift in wavelength determined at 636. Next, the corrected wavelength shift can be scaled to an equivalent pressure at 638, e.g., converted from a voltage value to a pressure value. The corrected wavelength shift at 636 and its scaled value at 638, however, have not been corrected for the ambient temperature of the pressure sensor.

In order to correct for the ambient temperature of the pressure sensor, a second laser 640 can be locked onto another phase-shift region, e.g., phase-shift region 312B between FBG 1 and FBG 4 of FIG. 3. This phase-shift region is insensitive to pressure and responds only to the ambient temperature of the pressure sensor. Using either a measurement of the change in drive current of the laser, e.g., in milliamps, or a change in wavelength, the controller 602 of FIG. 6A can determine the shift in wavelength at 642. The controller 602 can also determine the temperature of the second laser 640 at 644 by measuring the voltage across the submount thermistor via the electronic circuit 624 of FIG. 6A. The controller 602 can correct the determined shift in wavelength for the operating temperature of the second laser 640 by subtracting the determined operating temperature of the second laser 640 from the shift in wavelength determined at 646. Next, the corrected wavelength shift can be scaled to an equivalent pressure at 648, e.g., converted from a voltage value to a pressure value. Finally, at 650, the pressure determined at 648 can be subtracted from the pressure determined at 638 in order to determine a true pressure reading.

FIGS. 7A-7C depict an example of a pressure sensor that can be used to implement one or more techniques of this disclosure. The example of the pressure sensor depicted in FIGS. 7A-7C is an example of a standalone pressure sensor that can use one or more phase shift gratings. The type of grating written into the fiber can be, for example, a "phase shift" grating or a "Fabry Perot" grating. A "standalone" sensor can be capable of sensing pressure independently of the fiber being attached to a guide wire core subassembly. In contrast, an "integrated" pressure sensor can involve placing the fiber with the appropriate gratings written in it on a guide wire core and then completing the sensor once the fiber is positioned on the wire.

FIG. 7A is an example of a perspective view of an example of a optical fiber pressure sensor 700 that can include an optical fiber 702, which can be configured to transmit one or more optical sensing signals, and a temperature compensated Fiber Bragg Grating (FBG) interferometer (shown generally at 704 in FIG. 7C) that can be included in, or in optical communication with, the optical fiber 702. The FBG interferometer 704 can be configured to receive pressure (e.g., from pressure waves), and to modulate, in response to the received pressure, an optical sensing signal being delivered via the optical fiber 702 to the FBG interferometer 704. The pressure sensor 700 can include a sensor membrane 706, which can be in physical communication with the FBG interferometer 704. The sensor membrane 706 can be configured to help transmit the pressure to the FBG interferometer 704. The pressure sensor 700 can further include a sheath 708 that can, for example, help contain components of the pressure sensor 700 and/or help ease the pressure sensor through the vascular system.

FIG. 7B is an example of a cross-sectional end view of the pressure sensor 700 of FIG. 7A. As seen in FIG. 7B, the optical fiber 702 can extend through the pressure sensor 700, such as at substantially an axial center of the pressure sensor 700.

FIG. 7C is an example of a cross-sectional side view of the pressure sensor 700 of FIG. 7A, such as can be taken along section A-A of FIG. 7B. FIG. 7C depicts the optical fiber 702 extending through a proximal portion 710 and a distal portion 712 of the pressure sensor 700. A proximal portion of the phase shift grating of FBG interferometer 704 can be captured by a stiff, rigid, or solid supporting member 714, e.g., via bonding. The supporting member 714 can be a capillary tube, for example.

In the distal portion 712, the pressure sensor 700 can define a cavity 716, e.g., filled with air, such as laterally below the distal portion of the phase shift grating of FBG interferometer 704 and laterally below the remaining distal length of the fiber 702 extending distally axially beyond the phase shift grating. In the example shown in FIG. 7C, the flexible sensor membrane 706 can be thick enough such that it contacts the fiber 702 and the fiber 702 can be attached to the flexible sensor membrane 706, e.g., via bonding. The flexible sensor membrane 706 can include, for example, a thin polymer film, a heat seal film, or a thin metal foil. The flexible sensor membrane 706 can be attached to the pressure sensor 700, such as via bonding or solder. In an example, the membrane 706 can be made by casting a silicone layer.

The pressure sensor 700 can be sealed on both the proximal end 718 and the distal end 720. In addition, the sensor membrane 706 can be sealed creating the sealed cavity 706.

The example pressure sensor 700 of FIG. 7C depicts three FBGs, namely FBGs 1-3, along with an optional FBG, namely FBG 4. FBG 1 is independent of pressure and can be used for temperature measurements to provide a temperature compensated optical fiber pressure sensor, as described above with respect to FIG. 3 and FIG. 4A.

FBGs 2 and 3 can form a phase-shift FBG structure. The surface area of the membrane 706 can concentrate a change in pressure and can focus a mechanical response to the change in pressure at the phase-shift region between FBG 2 and FBG 3. This can enhance the sensitivity of the pressure sensor 700. The mechanical forces acting upon the phase-shift region between FBG 2 and FBG 3 can concentrate a stress in the phase-shift region. The concentrated stress in the phase-shift region can change the refractive index of the optical fiber 702, which, in turn, alters the phase relationship between FBG 2 and FBG 3. The change in phase-shift between FBG 2 and FBG 3 can be detected and quantified, and the change in pressure can be determined from the quantified phase-shift.

In an example, the pressure sensor 700 can optionally further include FBG 4, e.g., located axially more proximal than FBG 1. As described above with respect to FIG. 3 and FIG. 4C, FBGs 1 and 4 can form a phase-shifted FBG structure that can be used to detect and quantify a change in temperature in the pressure sensor 700, which can be substantially independent of any pressure variations, due to the location of FBGs 1 and 4 within the stiff, rigid, or solid supporting member 714. In the configuration shown in FIG. 7C, the supporting member 714 can be disposed about FBGs 1, 2, and 4.

FIGS. 8A-8C depict another example of a pressure sensor that can be used to implement one or more techniques of this disclosure, such as can use a standalone pressure sensor that can use one or more phase shift gratings.

FIG. 8A is a perspective view of an example of an optical fiber pressure sensor 800 that can include an optical fiber 802, which can be configured to transmit one or more optical sensing signals, and a temperature compensated Fiber Bragg Grating (FBG) interferometer (shown generally at 804 in FIG. 8C) in optical communication with the optical fiber 802. The FBG interferometer 804 can be configured to receive pressure (e.g., from pressure waves), and to modulate, in response to the received pressure, the optical sensing signal. The pressure sensor 800 can include a sensor membrane 806 that can be in physical communication with the FBG interferometer 804. The sensor membrane 806 can be configured to transmit the pressure to the FBG interferometer 804. The pressure sensor 800 can further include a sheath 808 that can, for example, help contain components of the pressure sensor 800 and/or help ease the pressure sensor through the vascular system.

FIG. 8B is an example of a cross-sectional end view of the pressure sensor 800 of FIG. 8A. As seen in FIG. 8B, the optical fiber 802 can extend through the pressure sensor 800, such as at substantially an axial center of the pressure sensor 800.

FIG. 8C is an example of a cross-sectional side view of the pressure sensor 800 of FIG. 8A, such as can be taken along section A-A of FIG. 8B. The optical fiber 802 can be supported in part by a stiff, rigid, or solid supporting member 814. The pressure sensor 800 can defines a cavity 816, e.g., filled with air.

As seen in FIG. 8C, the sensor membrane 806 can include a tapered portion 818 that can extend inwardly toward an axial center of the pressure sensor 804. The tapered portion 818 can help focus the response of the membrane 806 against the phase-shift region between FBG 2 and FBG 3, thereby further concentrating a stress in the phase-shift region, which can enhance the sensitivity of the pressure sensor 800.

In an example, a portion of the supporting member 814 can define a reservoir 820 that can be adjacent to the fiber 802. The reservoir 820 can be filled with a gas, e.g., air. In one example, the reservoir can be filled with a gas, e.g., nitrogen, that can provide greater temperature stability than air. In one example, the reservoir 820 can be a vacuum that can provide temperature stability. The reservoir 820 can provide a configuration that can be adjacent a limited cavity 816 immediately laterally below the fiber 802 between FBG 2 and FBG 3 such that it can be acted upon by the portion 818 yet the reservoir 820 still includes a large compressible volume.

In an example, such as shown in FIG. 8C, the flexible sensor membrane 806 can include, for example, a thin polymer film, a heat seal film, or a thin metal foil. The flexible sensor membrane 806 can be attached to the pressure sensor 800, such as via bonding or solder. In an example, the membrane 806 can be made by casting a silicone layer.

The pressure sensor 800 can be sealed on both the proximal end 817 and the distal end 819. The sensor membrane 806 can be sealed, such as for creating the sealed cavity 816.

The example of a pressure sensor 800 of FIG. 8C can include three FBGs (e.g., FBGs 1-3) along with an optional FBG (e.g., FBG 4). FBG 1 can be configured to be independent of pressure and can be used for temperature measurement, such as to provide a temperature compensated optical fiber pressure sensor, such as described above with respect to FIG. 3 and FIG. 4A.

FBGs 2 and 3 can form a phase-shifted FBG structure. The surface area of the membrane 806 can be configured to concentrate a change in pressure onto the portion 818, which can focus a mechanical response to the pressure at the phase-shift region between FBG 2 and FBG 3. The mechanical force acting upon the phase-shift region between FBG 2 and FBG 3 can concentrate a stress in the phase-shift region. The concentrated stress in the phase-shift region can change the refractive index of the optical fiber 802, such as to alter the phase relationship between FBG 2 and FBG 3. The change in phase-shift between FBG 2 and FBG 3 can be detected and quantified, and the change in pressure can be determined from the quantified phase-shift.

The pressure sensor 800 can optionally further include FBG 4, e.g., located axially more proximal than FBG 1. As described above with respect to FIG. 3 and FIG. 4C, FBGs 1 and 4 can form a phase-shifted FBG structure that can be used to detect and quantify a change in temperature in the pressure sensor 800. In the configuration shown in FIG. 8C, the supporting member 814 is not disposed about FBGs 1, 2, and 4, in contrast to the configuration example of FIG. 7C.

Figure 9B:
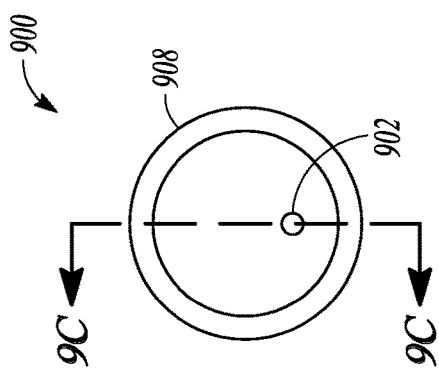
FIGS. 9A-9C depict another example of a pressure sensor that can be used to implement various techniques of this disclosure.
Figure 9A:
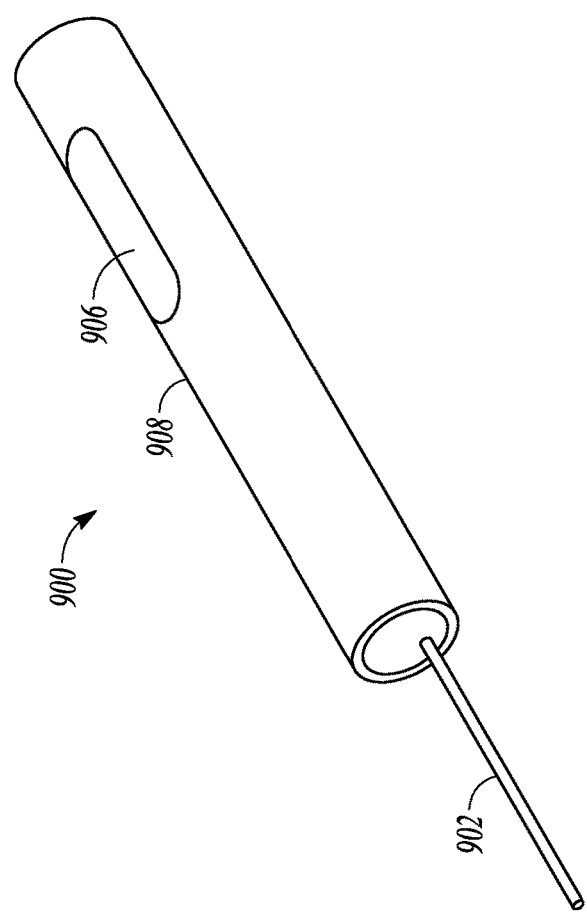
Figure 9C:
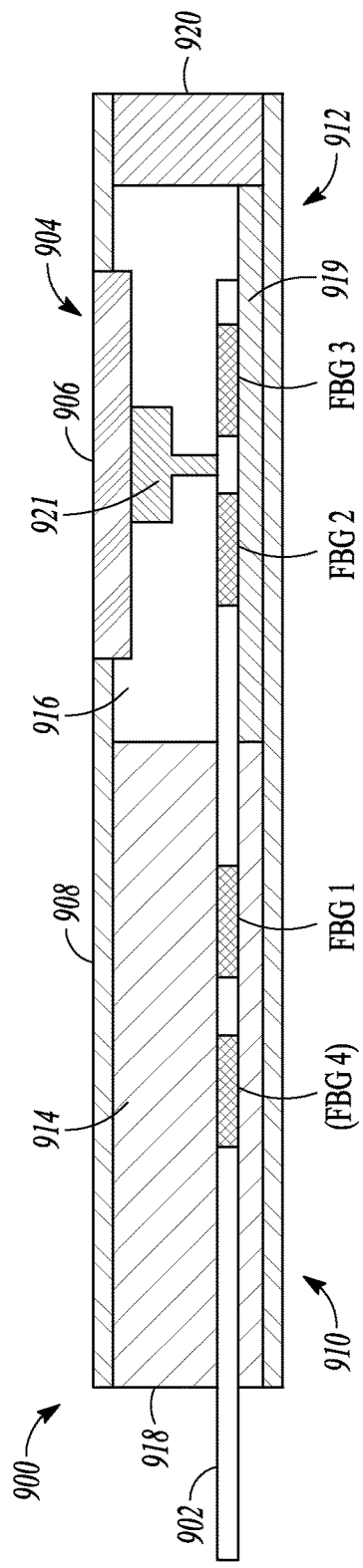

FIGS. 9A-9C depict another example of a pressure sensor that can be used to implement one or more techniques of this disclosure. The example of the pressure sensor depicted in FIGS. 9A-9C can provide a standalone pressure sensor that can use one or more phase shift gratings.

FIG. 9A is a perspective view of an optical fiber pressure sensor 900 that can include an optical fiber 902, which can be configured to transmit one or more optical sensing signals, and a temperature compensated Fiber Bragg Grating (FBG) interferometer (shown generally at 904 in FIG. 9C), such as in optical communication with the optical fiber 902. The FBG interferometer 904 can be configured to receive pressure (e.g., from pressure waves), and to modulate, in response to the received pressure, the optical sensing signal. The pressure sensor 900 can include a sensor membrane 906 that can be in physical communication with the FBG interferometer 904. The sensor membrane 906 can be configured to transmit the pressure to the FBG interferometer 904. The pressure sensor 900 can further include a sheath 908 that can, for example, help contain components of the pressure sensor 900 and/or help ease the pressure sensor through the vascular system.

FIG. 9B is an example of a cross-sectional end view of the pressure sensor 900 of FIG. 9A. As seen in FIG. 9B, the optical fiber 902 can extend through the pressure sensor 900 at a position that is offset from an axial center of the pressure sensor 900.

FIG. 9C is an example of a cross-sectional side view of the pressure sensor 900 of FIG. 9A, such as can be taken along section A-A of FIG. 9B. FIG. 9C depicts the optical fiber 902 extending through a proximal portion 910 and a distal portion 912 of the pressure sensor 904. A proximal portion of the FBG interferometer 904 can be captured by a supporting member 914, e.g., via bonding. The supporting member 914 can include a capillary tube, for example. In the distal portion 912, the pressure sensor 900 can define a cavity 916, e.g., filled with air.

As seen in the example shown in FIG. 9C, the sensor membrane 906 can be in mechanical communication with a portion 921 that can extend laterally inwardly into the pressure sensor 904. The portion 921 can focus the response of the membrane 906 against the phase-shift region between FBG 2 and FBG 3, which can thereby further concentrate a stress in the phase-shift region, which can enhance the sensitivity of the pressure sensor 900.

In the example shown in FIG. 9C, the flexible sensor membrane 906 can include, for example, a thin polymer film, a heat seal film, or a thin metal foil. The flexible sensor membrane 806 can be attached to the pressure sensor 900, such as via bonding or solder. In an example, the membrane 906 can be made by casting a silicone layer.

The pressure sensor 900 can be sealed on both the proximal end 918 and the distal end 920. In addition, the sensor membrane 906 can be sealed creating the sealed cavity 916.

The example of a pressure sensor 900 of FIG. 9C can include three FBGs (e.g., FBGs 1-3), along with an optional FBG (e.g., FBG 4). FBG 1 can be configured to be independent of pressure, such as explained above, and can be used for temperature measurement, such as to provide a temperature compensated optical fiber pressure sensor, such as described above with respect to FIG. 3 and FIG. 4A.

FBGs 2 and 3 can form a phase-shifted FBG structure. The surface area of the membrane 906 can concentrate any change in pressure into the portion 921, which can focus a mechanical response to the pressure at the phase-shift region between FBG 2 and FBG 3. The mechanical forces acting upon the phase-shift region between FBG 2 and FBG 3 can concentrate a stress in the phase-shift region. The concentrated stress in the phase-shift region can change the refractive index of the optical fiber 902, such as to alter the phase relationship between FBG 2 and FBG 3. The change in phase-shift between FBG 2 and FBG 3 can be detected and quantified, and the change in pressure can be determined from the quantified phase-shift. The pressure sensor 900 can include a compliant layer 919 laterally underneath the optical fiber 902, such as to allow the portion 921 to act on the optical fiber 902 without damaging the optical fiber 902.

The pressure sensor 900 can optionally further include FBG 4, e.g., located more proximal than FBG 1. As described above with respect to FIG. 3 and FIG. 4C, FBGs 1 and 4 can form a phase-shifted FBG structure that can be used to quantify a change in temperature in the pressure sensor 800. In the configuration shown in FIG. 9C, the supporting member 914 can be disposed about FBGs 1 and 4.

FIGS. 10A-10D depict an example of a pressure sensor that can be used to implement one or more techniques of this disclosure. The example of a pressure sensor depicted in FIGS. 10A-10D can provide an example standalone pressure sensor that can use one or more "Fabry Perot" grating arrangements.

Figure 10C:
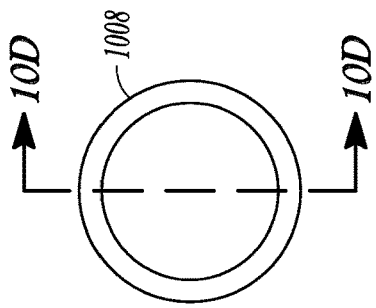
FIGS. 10A-10D depict another example of a pressure sensor that can be used to implement various techniques of this disclosure.
Figure 10B:
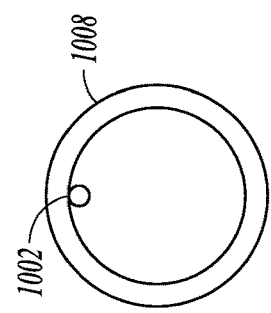
Figure 10A:
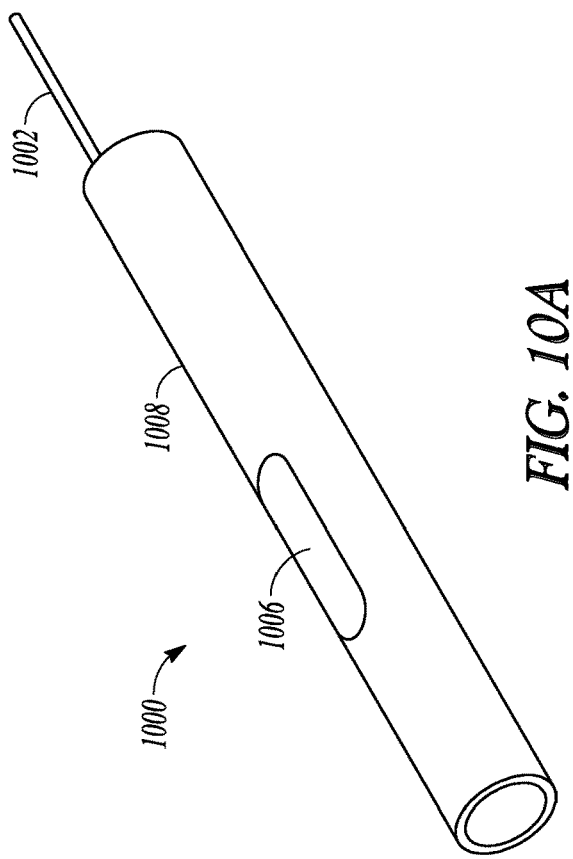

FIG. 10A is an example of a perspective view of an optical fiber pressure sensor 1000 that can include an optical fiber 1002, which can be configured to transmit one or more optical sensing signals, and a temperature compensated Fiber Bragg Grating (FBG) interferometer (shown generally at 1004 in FIG. 10D) that can be in optical communication with the optical fiber 1002. The FBG interferometer 1004 can be configured to receive pressure (e.g., from pressure waves), and to modulate, in response to the received pressure, the optical sensing signal. The pressure sensor 1000 can include a sensor membrane 1006 that can be in physical communication with the FBG interferometer 1004. The sensor membrane 1006 can be configured to transmit the pressure to the FBG interferometer 1004. The pressure sensor 1000 can further include a sheath 1008 that can, for example, help contain components of the pressure sensor 1000 and/or help ease the pressure sensor through the vascular system.

FIG. 10B is an example of a cross-sectional end view of the pressure sensor 1000 of FIG. 10A, depicting an example of a location of the optical fiber 1002. As seen in the example of FIG. 10B, the optical fiber 1002 can extend axially through the pressure sensor 1000, such as at a position that is axially offset from an axial center of the pressure sensor 1000. FIG. 10C is an example of a cross-sectional end view of the pressure sensor without the optical fiber 1002.

Figure 10D:
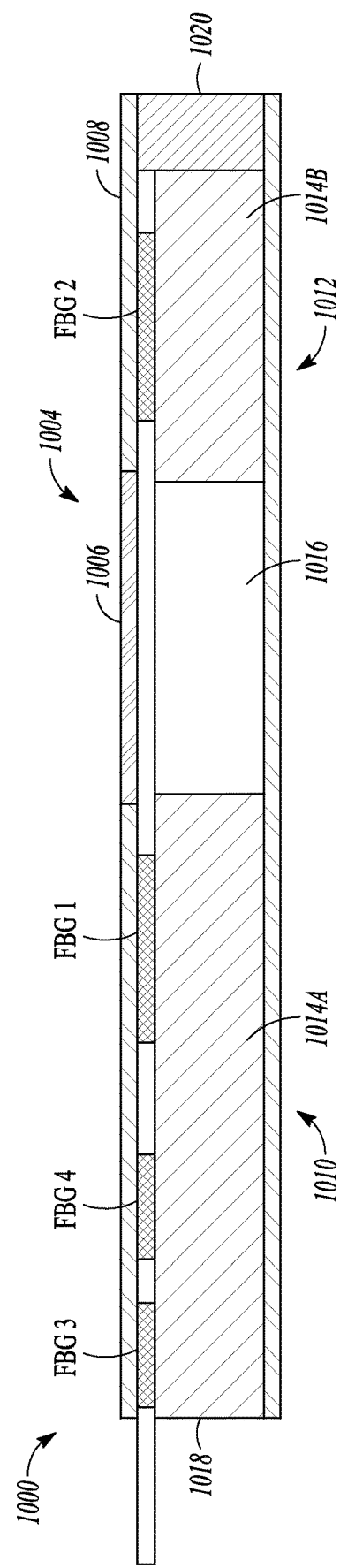

FIG. 10D is an example of a cross-sectional side view of the pressure sensor 1000 of FIG. 10A, such as can be taken along section A-A of FIG. 10C. FIG. 10D depicts an example of the optical fiber 1002 extending through a proximal portion 1010 and a distal portion 1012 of the pressure sensor 1004. A proximal portion of the optical fiber 1002 can be captured by a first supporting member 1014A and a distal portion 1012 of the optical fiber 1002 can be captured by a second supporting member 1014B, e.g., via bonding.

The pressure sensor 1000 can include a sensor member 1006. The pressure sensor 1000 can define a cavity 1016, e.g., filled with air, laterally below the sensor membrane 1006. The sensor membrane 1006 and the cavity 1016 can concentrate a stress in the area between the Fabry-Perot gratings FBG 1 and FBG 2, which can enhance the sensitivity of the pressure sensor 1000.

The flexible sensor membrane 1006 can include, for example, a thin polymer film, a heat seal film, or a thin metal foil. The flexible sensor membrane 1006 can be attached to the pressure sensor 1000, such as via bonding or solder. In an example, the membrane 1006 can be made by casting a silicone layer.

The pressure sensor 1000 can be sealed on both the proximal end 1018 and the distal end 1020. The sensor membrane 1006 can be sealed, such as for creating the sealed cavity 1016.

The example of a pressure sensor 1000 of FIG. 10D can include four FBGs (e.g., FBGs 1-4). FBGs 3 and 4 can form a phase-shifted FBG structure, such as for sensing temperature. The change in phase-shift between FBG 3 and FBG 4 can be detected and quantified, and the change in temperature can be determined from the quantified phase-shift, such as described above.

The pressure sensor 1000 can further include Fabry-Perot gratings FBG 1 and FBG 2, which can be used to sense changes in pressure. Similar to the phase-shift grating structures described above with respect to FIGS. 7-9, the Fabry- Perot gratings FBG 1 and FBG 2 can create a phase shift that can be tracked in a manner similar to that described above. That is, a notch can be created in the wavelength response to the Fabry-Perot gratings FBG 1 and FBG 2, as shown and described in more detail with respect to FIG. 11. A point on a slope of the notch can be set and tracked, a phase shift can be detected and quantified, and the change in pressure can be determined from the quantified phase-shift, such as described in detail above.

Figure 11:
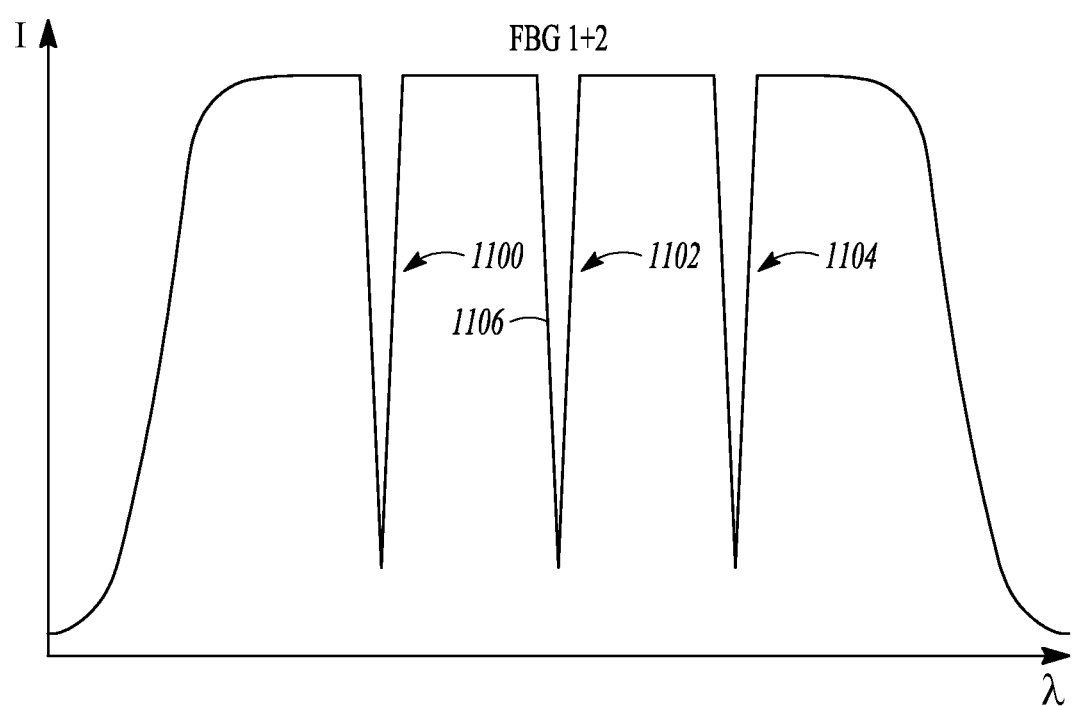
FIG. 11 depicts a conceptual response diagram related to the example of a pressure sensor shown in FIG. 10D.

FIG. 11 depicts an example of a conceptual response diagram related to the example of a pressure sensor shown in FIG. 10D. In particular, FIG. 11 depicts a conceptual wavelength response of the Fabry-Perot gratings FBG 1 and FBG 2 of FIG. 10D. As seen in the example shown in FIG. 11, the wavelength response of the Fabry-Perot gratings FBG 1 and FBG 2 can include three notches, 1100, 1102, 1104. This is in contrast to the wavelength responses of the phase-shift structures shown in FIGS. 4A-4C, which can include a single notch for a pair of FBGs. The additional notches in FIG. 11 can be a result of the increased distance between the Fabry-Perot gratings FBG 1 and FBG 2. As the distance between the Fabry-Perot gratings FBG 1 and FBG 2 increases, additional notches can occur. As the distance between the Fabry-Perot gratings FBG 1 and FBG 2 decreases, notches can disappear until the response resembles that of the phase-shift structures described above.

In a manner similar to that described above, a wavelength of a narrow band laser (in relation to the response of FBGs 1 and 2) can be locked on a point on a slope 1106 of a narrow transmission notch, e.g., notch 1102, in FIG. 11, e.g., at about 50% of the length of the notch 1102. As the pressure changes, the notch 1102 and, consequently, the point on the slope 1106 shifts. A tracking circuit can then track the point on the slope 1106 and a phase-shift can be determined from its change in position. The intensity of reflected light will be modified when the notch 1106 moves. A phase shift can be quantified, and the change in pressure can be determined from the quantified phase-shift, such as described in detail above.

Figure 12B:
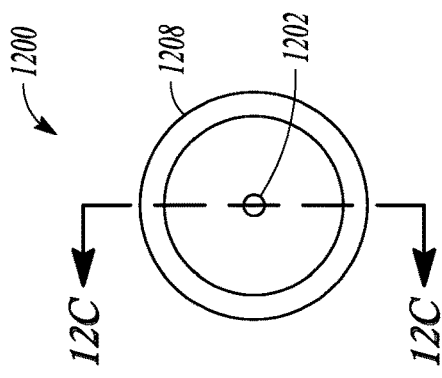
FIGS. 12A-12C depict another example of a pressure sensor that can be used to implement various techniques of this disclosure.
Figure 12A:
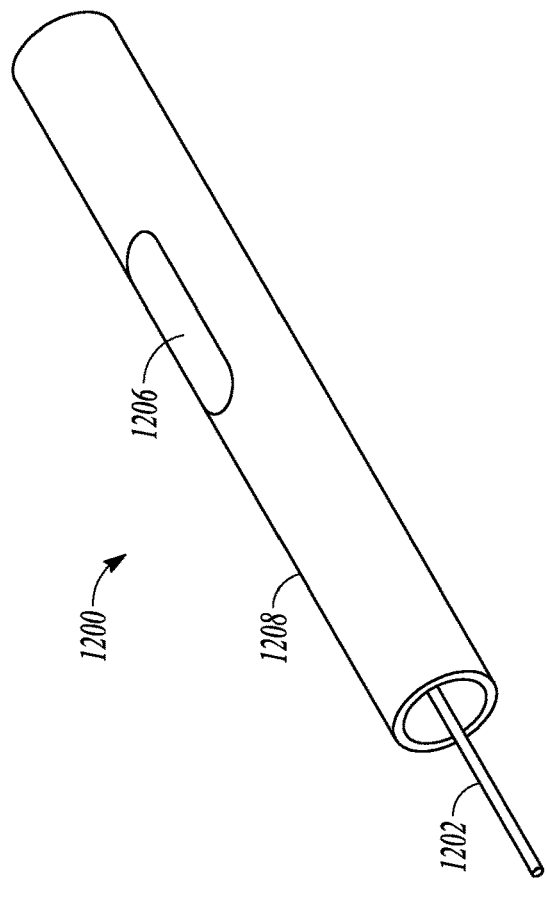
Figure 12C:
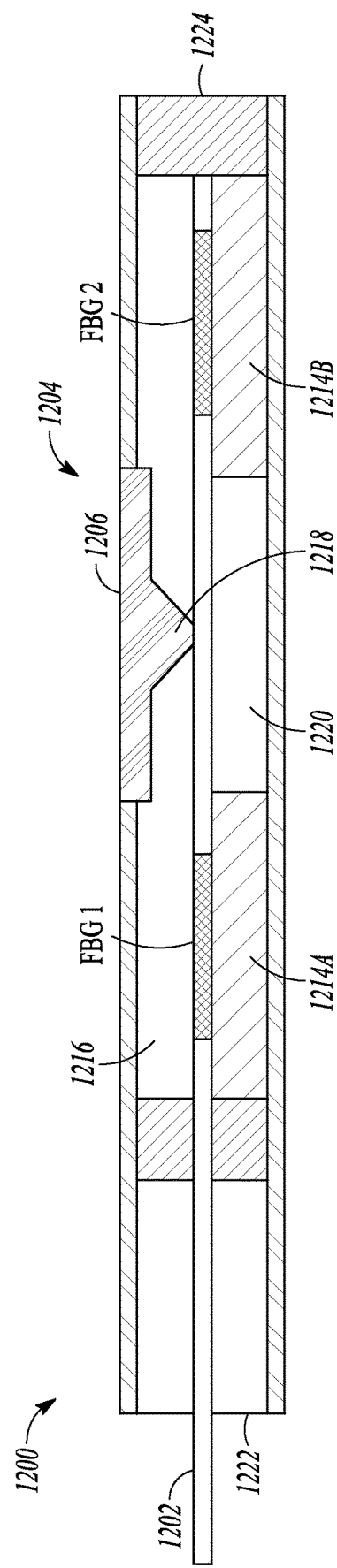

FIGS. 12A-12C depict another example of a pressure sensor that can be used to implement one or more techniques of this disclosure. The example of a pressure sensor depicted in FIGS. 12A-12C can provide another example standalone pressure sensor that can use one or more Fabry-Perot grating arrangements.

FIG. 12A is an example of a perspective view of an optical fiber pressure sensor 1200 that can include an optical fiber 1202 that can be configured to transmit one or more optical sensing signals and a temperature compensated Fiber Bragg Grating (FBG) interferometer (shown generally at 1204 in FIG. 12C) in optical communication with the optical fiber 1202. The FBG interferometer 1204 can be configured to receive pressure, e.g., from pressure waves, and to modulate, in response to the received pressure, the optical sensing signal. The pressure sensor 1200 can include a sensor membrane 1206 that can be in physical communication with the FBG interferometer 1204. The sensor membrane 1206 can be configured to transmit the pressure to the FBG interferometer 1204. The pressure sensor 1200 can further include a sheath 1208 that can, for example, help contain components of the pressure sensor 1200 and/or help ease the pressure sensor through the vascular system.

FIG. 12B is an example of a cross-sectional end view of the pressure sensor 1200 of FIG. 12A. As seen in FIG. 12B, the optical fiber 1202 can extend axially through the pressure sensor 1200 such as at substantially an axial center of the pressure sensor 1200.

FIG. 12C is an example of a cross-sectional side view of the pressure sensor 1200 of FIG. 12A, such as can be taken along section A-A of FIG. 12B. The optical fiber 1202 can be supported in part by supporting members 1214A, 1214B. The pressure sensor 1200 can define a cavity 1216, e.g., filled with air.

As seen in the example of FIG. 12C, the sensor membrane 1206 can include a portion 1218 that can extend inwardly toward a center of the pressure sensor 1204 and that can taper, such as to a point. The portion 1218 can focus the response of the membrane 1206 against the area between FBG 1 and FBG 2, such as for thereby further concentrating a stress in the phase-shift region, which can enhance the sensitivity of the pressure sensor 1200.

A portion of the supporting member 1214 can define a reservoir 1220, such as laterally below the area extending axially between FBG 1 and FBG 2. The reservoir 1220 can further enhance the sensitivity of the pressure sensor 1200, such as by allowing the area between FBG 1 and FBG 2 to deflect into the reservoir 1220.

In the example shown in FIG. 12C, the flexible sensor membrane 1206 can include, for example, a thin polymer film, a heat seal film, or a thin metal foil. The flexible sensor membrane 1206 can be attached to the pressure sensor 1200, such as via bonding or solder. In an example, the membrane 1206 can be made by casting a silicone layer.

The pressure sensor 1200 can be sealed, such as on both the proximal end 1222 and the distal end 1224. The sensor membrane 1206 can be sealed, such as for creating the sealed cavity 1216.

The example of a pressure sensor 1200 of FIG. 12C can include two FBGs (e.g., Fabry-Perot gratings FBG 1 and FBG 2), which can be used to sense changes in pressure, such as described above with respect to FIG. 10D. The pressure sensor 1200 can optionally further include one or more temperature compensating FBGs. For example, the pressure sensor 1200 can include two additional FBGs (e.g., FBGs 3 and 4 of FIG. 10D), which can form a phase-shifted FBG structure, such as for sensing temperature. The change in phase-shift between FBG 3 and FBG 4 can be quantified and the change in temperature can be determined from the quantified phase-shift, such as described above.

FIGS. 13A-13C depict an example of a guidewire in combination with an optical pressure sensor. FIG. 13A is an example of a perspective view illustrating a combination 1300 of a guidewire 1302 and an optical fiber 1304 attached to an optical fiber pressure sensor. An optical fiber pressure sensor can be attached at a distal end of the guidewire 1302. The optical fiber 1304 can be disposed in a smooth, rounded groove (groove 1306 of FIG. 13C) extending axially along an outer diameter of the guidewire 1302 and optionally helically wound about the guidewire 1302, such as within a helically axially extending groove. FIG. 13B is an example of a cross-sectional side view of the combination 1300 of FIG. 13A, illustrating the optional helical pitch of the combination.

FIG. 13C is an example of a cross-sectional end view of the combination 1300 of FIG. 13A, such as can be taken along section A-A of FIG. 13B. The guidewire 1302 can include a solid guidewire with a smooth, rounded groove 1306 etched out, for example, of the guidewire material (or etched out of a coating thereupon), thereby preserving most of the guidewire material, which can help preserve its mechanical properties. In this manner, the guidewire can be substantially solid, which can avoid the kinking issues that can be associated with hollow guidewires. Using a substantially solid guidewire can improve the guidewire's torque capabilities. In an example, a coating can be applied over the guidewire 1302 and over the fiber 1304, such as to help protect the fiber 1304 or to help secure the fiber 1304 to the guidewire 1302.

In some examples, the guidewires shown and described in this disclosure can have a maximum diameter (or maximum width if the guidewire does not have a circular cross-section) of less than about 0.018 inches (18 mil). In one specific example, a guidewire can have a maximum diameter (or maximum width if the guidewire does not have a circular cross-section) of about 0.014 inches (14 mil).

The grooves in the guidewires shown and described in this disclosure account for a small fraction of the overall cross-sectional area of the guidewire. In one specific example, the groove accounts for less than one percent of the cross-sectional area of the guidewire.

FIGS. 14A-14C depict an example of a guidewire in combination with an optical fiber pressure sensor. FIG. 14A is an example of a perspective view illustrating a combination 1400 of a guidewire 1402 and an optical fiber 1404 that can be attached to an optical fiber pressure sensor. An optical fiber pressure sensor can be attached at a distal end of the guidewire 1402. The optical fiber 1402 can be disposed in a flat groove (flat groove 1406 of FIG. 14C) extending axially along an outer diameter of the guidewire 1402 (or along a coating thereupon) and optionally helically wound about the guidewire 1402. FIG. 14B is a cross-sectional side view of the combination 1400 of FIG. 14A, illustrating the helical pitch of the combination. The helical design can allow any stresses, e.g., from compression and tension, to be more evenly distributed along the length of the guidewire.

FIG. 14C is a cross-sectional end view of the combination 1400 of FIG. 14A, such as can be taken along section A-A of FIG. 14B. The guidewire 1402 can include a solid guidewire with a flat groove 1406 etched out, for example, of the guidewire material, or a coating thereupon, thereby preserving most of the guidewire material and the mechanical properties associated therewith. In this manner, the guidewire can be substantially solid, which can help avoid the kinking issues that can be associated with hollow guidewires. Using a substantially solid guidewire can provide better torque capability of the guidewire. In an example, a coating can be applied over the guidewire 1402 and the fiber 1404, such as to help protect the fiber 1404 or to help secure the fiber 1404 to the guidewire 1402.

FIGS. 15A-15C depict an example of a guidewire in combination with an optical fiber pressure sensor. FIG. 15A is an example of a perspective view illustrating a combination 1500 of a multifilar guidewire 1502 and an optical fiber 1504 that can be attached to an optical fiber pressure sensor. An optical fiber pressure sensor can be attached at a distal end of the guidewire 1502. The optical fiber 1504 can be disposed in an interstice between filaments of the multifilar guidewire 1502 and optionally axially helically wound about the guidewire 1502. FIG. 15B is an example of a cross-sectional side view of the combination 1500 of FIG. 15A, illustrating an example of the helix pitch of the combination.

FIG. 15C is an example of a cross-sectional end view of the combination 1500 of FIG. 15A, such as can be taken along section A-A of FIG. 15B. The multifilar guidewire 1502 can include multiple filaments 1506. The optical fiber 1504 can be disposed in an interstice between two filaments 1506, for example, toward an outer diameter of the guidewire 1502. In this manner, the guidewire can be substantially rigid, like a solid guidewire, which can help avoid the kinking issues that can be associated with hollow guidewires. Using a substantially solid guidewire can help provide desired torque capability of the guidewire. In an example, a coating can be applied over the guidewire 1502 and the fiber 1504, such as to help protect the fiber 1504 or to help secure the fiber 1504 to the guidewire 1502.

Figure 16:
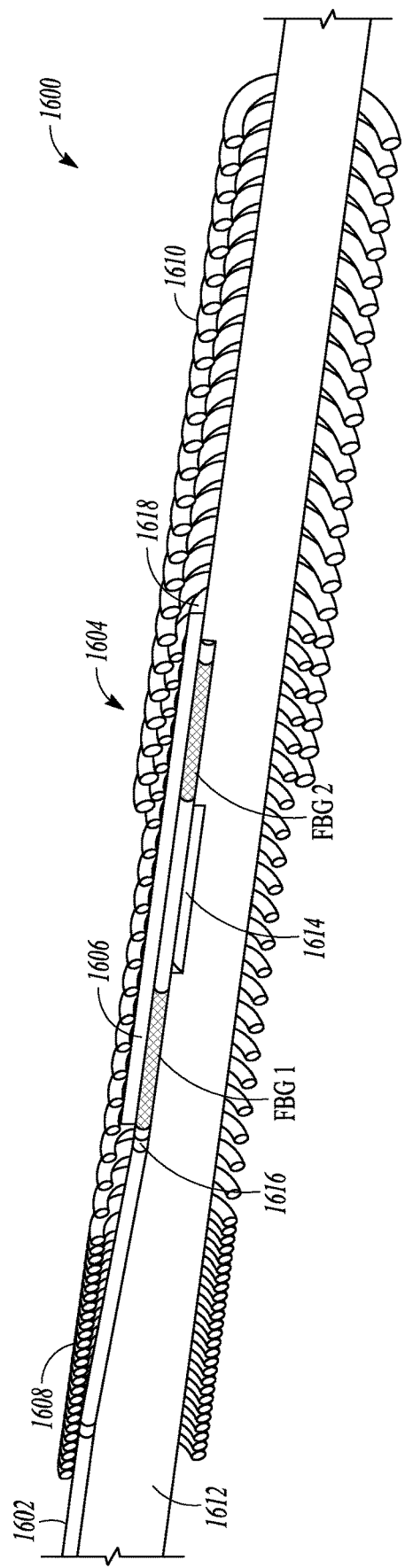
FIG. 16 depicts another example of a pressure sensor that can be used to implement various techniques of this disclosure.

FIG. 16 depicts another example of a pressure sensor that can be used to implement various techniques of this disclosure. The example of a pressure sensor depicted in FIG. 16 can provide an example of an integrated pressure sensor that can use one or more Fabry-Perot grating arrangements. Again, an "integrated" pressure sensor can involve placing the fiber with the appropriate gratings written in the fiber on a guidewire and then completing the sensor once the fiber is positioned on the wire.

FIG. 16 is an example of a perspective cross-sectional view of an optical fiber pressure sensor 1600 that can include an optical fiber 1602 that can be configured to transmit one or more optical sensing signals and a temperature compensated Fiber Bragg Grating (FBG) interferometer 1604 in optical communication with the optical fiber 1602. The FBG interferometer 1604 can be configured to receive pressure, e.g., from pressure waves, and to modulate, in response to the received pressure, the optical sensing signal. The pressure sensor 1600 can include a sensor membrane 1606 that can be in physical communication with the FBG interferometer 1604. The sensor membrane 1606 can be configured to transmit the pressure to the FBG interferometer 1604.

The example of a pressure sensor 1600 of FIG. 16 can further include Fabry-Perot gratings FBG 1 and FBG 2, which can be used to sense changes in pressure. The Fabry-Perot gratings FBG 1 and FBG 2 can create a phase shift that can be tracked in a manner similar to that described above.

The pressure sensor 1600 of FIG. 16 can further include a proximal coil 1608 and a distal coil 1610. The proximal and distal coils 1608, 1610 can provide flexibility to aid advancement of the pressure sensor 1600 through tortuous pathways. In one example, the proximal and distal coils 1608, 1610 can be affixed together via a mechanical joint (not depicted), e.g., via solder or adhesive. The FBG interferometer 1604 can, in some examples, be positioned underneath the mechanical joint to provide additional protection to the FBG interferometer 1604.

The pressure sensor 1600 of FIG. 16 can further include a guidewire 1612 to which the optical fiber 1602 can be attached. In the example depicted in FIG. 16, a portion of the guidewire 1612 can define a machined gap (not depicted) underneath the proximal coil 1608. The machined gap can allow the optical fiber 1602 to extend longitudinally or helically along the outer surface of the guidewire 1612 and then transition underneath the proximal coil gradually into the machined gap.

The guidewire 1612 can also define cavity 1614, e.g., filled with air, laterally below the sensor membrane 1606. The sensor membrane 1606 and the cavity 1614 can concentrate a stress in the area between the Fabry-Perot gratings FBG 1 and FBG 2, which can enhance the sensitivity of the pressure sensor 1600. The optical fiber 1602 can be securely attached to the guidewire 1612 on each side of the cavity 1614. In addition, the sensor membrane 1606 can be sealed 360 degrees around the guidewire 1612 at an optical fiber entry end 1616 of the sensor membrane 1606 and at a distal end 1618 of the optical fiber 1602 and along the edges of the membrane 1606.

Figure 17:
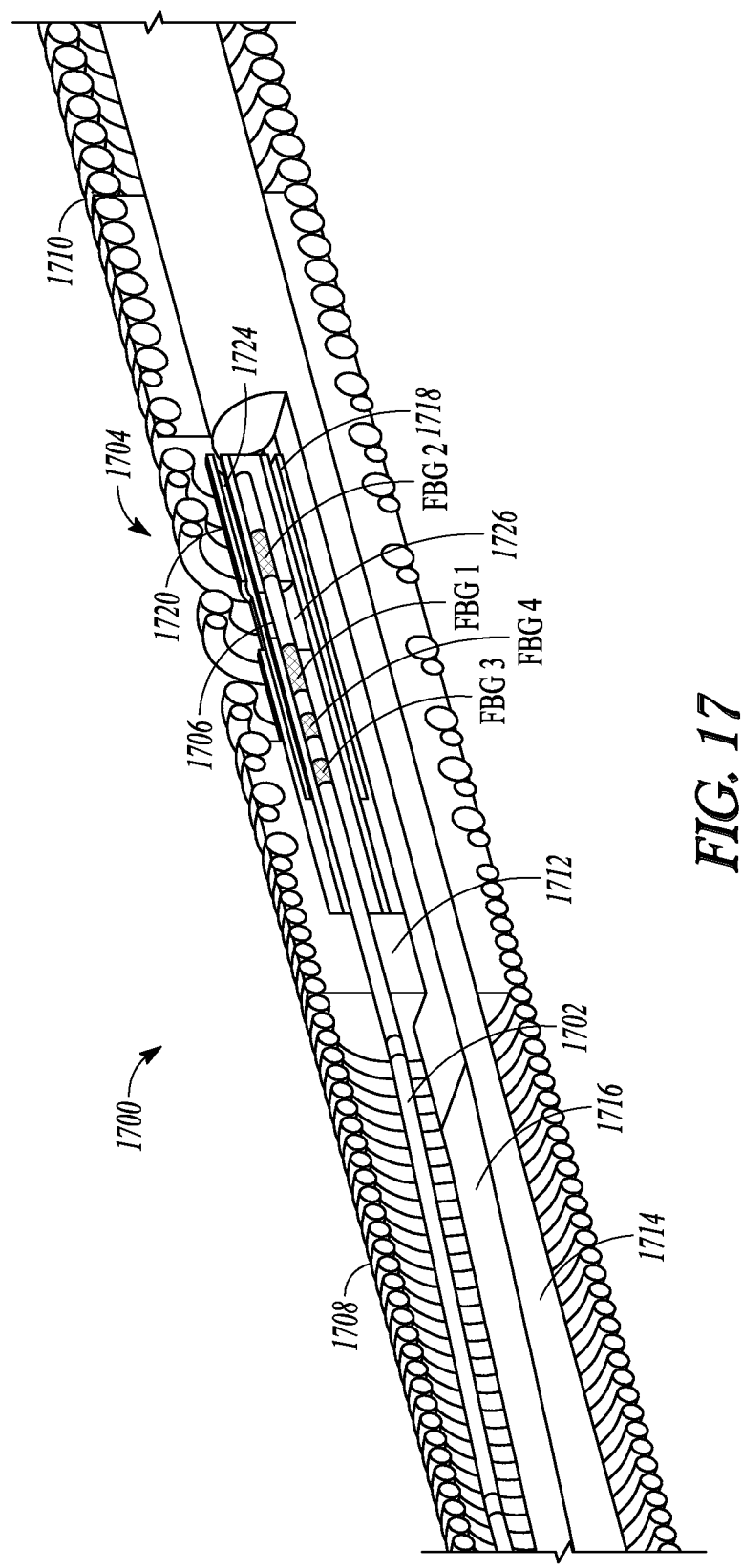
FIG. 17 depicts another example of a pressure sensor that can be used to implement various techniques of this disclosure.

FIG. 17 depicts another example of a pressure sensor that can be used to implement various techniques of this disclosure. FIG. 17 depicts another example of a pressure sensor that can be used to implement various techniques of this disclosure. The example of a pressure sensor 1700 depicted in FIG. 17 can provide an example standalone pressure sensor that can use one or more Fabry-Perot grating arrangements.

FIG. 17 is an example of a perspective cross-sectional view of an optical fiber pressure sensor 1700 that can include an optical fiber 1702 that can be configured to transmit one or more optical sensing signals and a temperature compensated Fiber Bragg Grating (FBG) interferometer 1704 in optical communication with the optical fiber 1702. The FBG interferometer 1704 can be configured to receive pressure, e.g., from pressure waves, and to modulate, in response to the received pressure, the optical sensing signal. The pressure sensor 1700 can include a sensor membrane 1706 that can be in physical communication with the FBG interferometer 1704. The sensor membrane 1706 can be configured to transmit the pressure to the FBG interferometer 1704.

The example of a pressure sensor 1700 of FIG. 17 can include four FBGs (e.g., FBGs 1-4.) FBGs 3 and 4 can form a phase-shifted FBG structure, such as for sensing temperature. The change in phase-shift between FBG 3 and FBG 4 can be detected and quantified, and the change in temperature can be determined from the quantified phase-shift, such as described above.

The pressure sensor 1700 can further include Fabry-Perot gratings FBG 1 and FBG 2, which can be used to sense changes in pressure. Similar to the phase-shift grating structures described above with respect to FIG. 10D, the Fabry-Perot gratings FBG 1 and FBG 2 can create a phase shift that can be tracked in a manner similar to that described above. That is, a notch can be created in the wavelength response to the Fabry-Perot gratings FBG 1 and FBG 2, as shown and described in detail above. A point on a slope of the notch can be set and tracked, a phase shift can be detected and quantified, and the change in pressure can be determined from the quantified phase-shift, such as described in detail above.

The pressure sensor 1700 of FIG. 17 can further include a proximal coil 1708 and a distal coil 1710. The proximal and distal coils 1708, 1710 can provide additional flexibility to aid advancement of the pressure sensor 1700 through tortuous pathways. In one example, the proximal and distal coils 1708, 1710 can be affixed together via a mechanical joint 1712, e.g., via solder or adhesive. The FBG interferometer 1704 can, in some examples, be positioned underneath the mechanical joint 1712 to provide additional protection to the FBG interferometer 1704.

The pressure sensor 1700 of FIG. 17 can further include a guidewire 1714 to which the FBG interferometer 1704 can be attached. In the example depicted in FIG. 17, a portion of the guidewire can define a machined gap 1716 underneath a portion of the proximal coil 1708 and the distal coil 1710. The machined gap 1716 can allow the optical fiber 1702 to extend longitudinally or helically along the outer surface of the guidewire 1714 and then transition underneath the proximal coil 1708 gradually into the machined gap 1716.

The example of a pressure sensor 1700 in FIG. 17 can include a cantilevered design, which can be applied to any of the examples of standalone pressure sensors described in this disclosure. More particularly, the pressure sensor 1700 can include a cantilever tube 1718 that is disposed about a distal portion of the optical fiber 1702 within the machined gap 1716. In addition, the pressure sensor 1700 can include a sensor tube 1720 disposed within the cantilever tube 1718 and about the distal portion of the optical fiber 1702. To provide support to a portion of the optical fiber 1702, the pressure sensor 1700 can also include a fiber support 1722 that is positioned between the sensor tube 1720 and a portion of the optical fiber 1702.

Between a portion of an inner surface of the cantilever tube 1718 and an outer surface of the sensor tube 1720, the pressure sensor 1700 can define a space 1724, thereby providing a double-walled housing construction. The double-walled housing construction and the space 1724 can allow the outer surface of the sensor tube 1720 to be mounted to the guidewire 1714 while isolating the FBG interferometer 1704 from motion of the guidewire 1714 and contact with the proximal coil 1708.

The FBG interferometer 1704 can also define cavity 1726, e.g., filled with air, laterally below the sensor membrane 1706 and a portion of the optical fiber 1702 and within the region defined by the sensor tube 1720. The sensor membrane 1706 and the cavity 1726 can concentrate a stress in the area between the Fabry-Perot gratings FBG 1 and FBG 2, which can enhance the sensitivity of the pressure sensor 1700.

Figure 18:
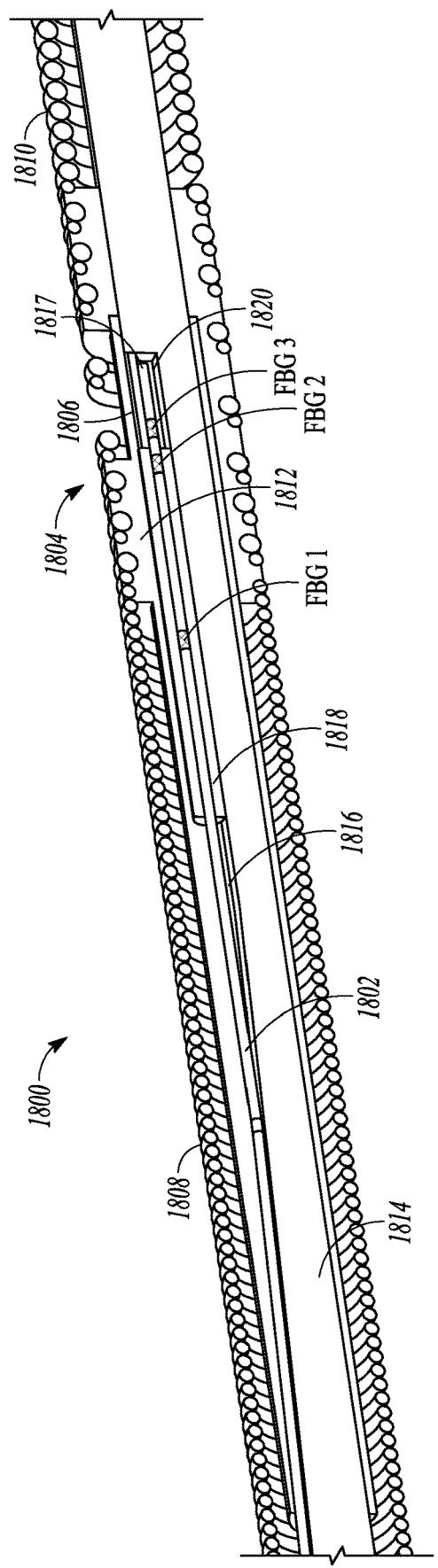
FIG. 18 depicts another example of a pressure sensor that can be used to implement various techniques of this disclosure.

FIG. 18 depicts another example of a pressure sensor that can be used to implement various techniques of this disclosure. The example of a pressure sensor depicted in FIG. 18 can provide an example of an integrated pressure sensor that can use one or more Fabry-Perot grating arrangements.

FIG. 18 is an example of a perspective cross-sectional view of an optical fiber pressure sensor 1800 that can include an optical fiber 1802 that can be configured to transmit one or more optical sensing signals and a temperature compensated Fiber Bragg Grating (FBG) interferometer 1804 in optical communication with the optical fiber 1802. The FBG interferometer 1804 can be configured to receive pressure, e.g., from pressure waves, and to modulate, in response to the received pressure, the optical sensing signal. The pressure sensor 1800 can include a sensor membrane 1806 that can be in physical communication with the FBG interferometer 1804. The sensor membrane 1806 can be configured to transmit the pressure to the FBG interferometer 1804.

The pressure sensor 1800 of FIG. 18 can further include a proximal coil 1808 and a distal coil 1810. The proximal and distal coils 1808, 1810 can provide additional flexibility to aid advancement of the pressure sensor 1800 through tortuous pathways. In one example, the proximal and distal coils 1808, 1810 can be affixed together via a mechanical joint 1812, e.g., via solder or adhesive. The FBG interferometer 1804 can, in some examples, be positioned underneath the mechanical joint 1812 to provide additional protection to the FBG interferometer 1804.

The pressure sensor 1800 of FIG. 18 can further include a guidewire 1814 to which the FBG interferometer 1804 can be attached. In the example depicted in FIG. 18, a portion of the guidewire 1814 can define a machined gap 1816 underneath a portion of the proximal coil 1808 and the distal coil 1810. The machined gap 1816 can allow the optical fiber 1802 to extend longitudinally or helically along the outer surface of the guidewire 1814 and then transition underneath the proximal coil 1808 gradually into the machined gap 1816.

The example of a pressure sensor 1800 in FIG. 18 can include a capillary tube design. More particularly, the pressure sensor 1800 can include a capillary tube 1818 to support a portion of the optical fiber 1802. The capillary tube 1818 can be disposed about a distal portion of the optical fiber 1802 within the machined gap 1816.

As seen in FIG. 18, a portion 1817 of the optical fiber 1802 can extend beyond a distal end of the capillary tube 1818 and over a cavity 1820, e.g., filled with air, that is laterally below the portion of the optical fiber 1802 that extends beyond the distal end of the capillary tube 1818. The example of a pressure sensor 1800 of FIG. 18 can include at least three FBGs (e.g., FBGs 1-3.) FBG 1 can be configured to be independent of pressure and can be used for temperature measurement, such as to provide a temperature compensated optical fiber pressure sensor, such as described above with respect to FIG. 3 and FIG. 4A.

FBGs 2 and 3 can form a phase-shift FBG structure. The surface area of the membrane 1806 can concentrate a change in pressure and can focus a mechanical response to the change in pressure at the phase-shift region between FBG 2 and FBG 3. This focused mechanical response can enhance the sensitivity of the pressure sensor 1800. The mechanical forces acting upon the phase-shift region between FBG 2 and FBG 3 can concentrate a stress in the phase-shift region. The concentrated stress in the phase-shift region can change the refractive index of the optical fiber 1802, which, in turn, alters the phase relationship between FBG 2 and FBG 3. The change in phase-shift between FBG 2 and FBG 3 can be detected and quantified, and the change in pressure can be determined from the quantified phase-shift.

As seen in FIG. 18, the sensor membrane 1806 can be disposed about the guidewire 1814, the capillary tube 1818, and the portion of the optical fiber that extends beyond the distal end of the capillary tube 1818.

Figure 19:
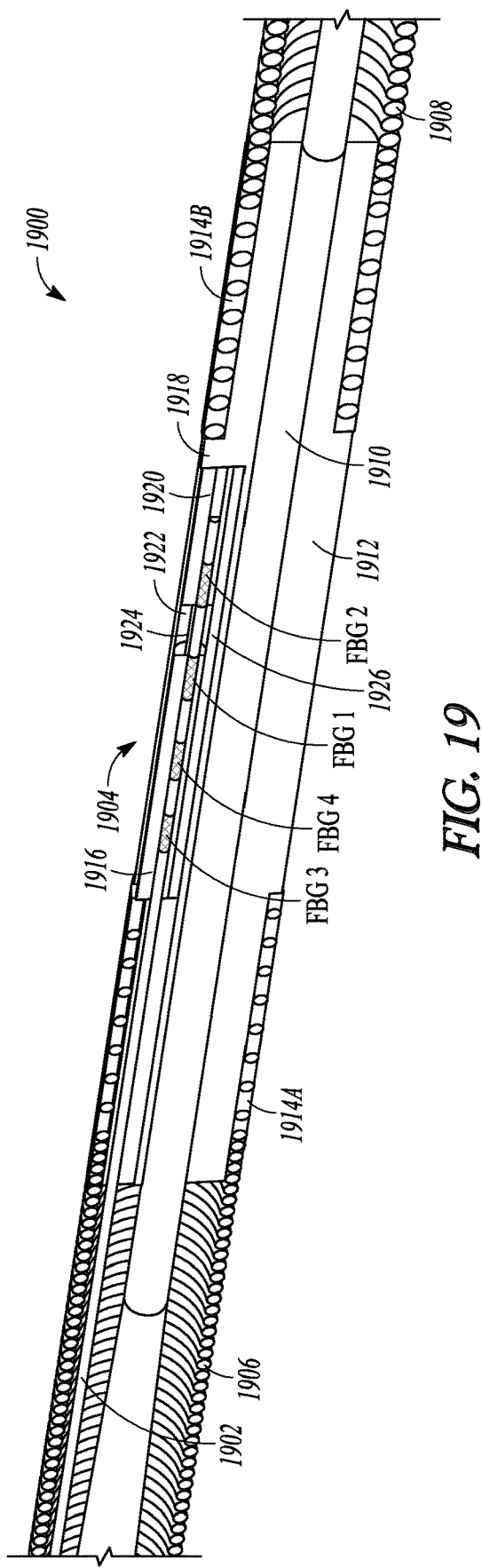
FIG. 19 depicts another example of a pressure sensor that can be used to implement various techniques of this disclosure.

FIG. 19 depicts another example of a pressure sensor that can be used to implement various techniques of this disclosure. FIG. 19 depicts another example of a pressure sensor that can be used to implement various techniques of this disclosure. The example of a pressure sensor 1900 depicted in FIG. 19 can provide an example standalone pressure sensor that can use one or more Fabry-Perot grating arrangements.

FIG. 19 is an example of a perspective cross-sectional view of an optical fiber pressure sensor 1900 that can include an optical fiber 1902 that can be configured to transmit one or more optical sensing signals and a temperature compensated Fiber Bragg Grating (FBG) interferometer 1904 in optical communication with the optical fiber 1902. The FBG interferometer 1904 can be configured to receive pressure, e.g., from pressure waves, and to modulate, in response to the received pressure, the optical sensing signal.

The example of a pressure sensor 1900 of FIG. 19 can include four FBGs (e.g., FBGs 1-4.) FBGs 3 and 4 can form a phase-shifted FBG structure, such as for sensing temperature. The change in phase-shift between FBG 3 and FBG 4 can be detected and quantified, and the change in temperature can be determined from the quantified phase-shift, such as described above.

The pressure sensor 1900 can further include Fabry-Perot gratings FBG 1 and FBG 2, which can be used to sense changes in pressure. Similar to the phase-shift grating structures described above with respect to FIG. 10D, the Fabry-Perot gratings FBG 1 and FBG 2 can create a phase shift that can be tracked in a manner similar to that described above. That is, a notch can be created in the wavelength response to the Fabry-Perot gratings FBG 1 and FBG 2, as shown and described in detail above. A point on a slope of the notch can be set and tracked, a phase shift can be detected and quantified, and the change in pressure can be determined from the quantified phase-shift, such as described in detail above.

The pressure sensor 1900 of FIG. 19 can further include a proximal coil 1906, a distal coil 1908, and a guidewire 1910. The proximal and distal coils 1906, 1908 can provide additional flexibility to aid advancement of the pressure sensor 1900 through tortuous pathways.

The pressure sensor 1900 of FIG. 19 can further include a tubular housing 1912 that can be disposed about the guidewire 1912 between the proximal and distal coils 1906, 1908. In one example, the proximal and distal coils 1906, 1908 can be affixed to the housing 1912 via mechanical joints 1914A, 1914B, e.g., via solder or adhesive. The housing 1912 can be affixed to the guidewire 1910 via a mechanical joint 1915.

In addition, the pressure sensor 1900 can include a sensor tube 1916 disposed within the housing 1912 and disposed about a distal portion of the optical fiber 1902. More particularly, the sensor tube 1916 can be positioned within an area machined out of a portion of the outer wall 1918 of the housing 1912. To provide support to the optical fiber 1902, a fiber support 1920 can be disposed about the optical fiber 1902 between the sensor tube 1916 and the optical fiber 1902.

To allow the received pressure to reach the optical fiber 1902, a portion of the sensor tube 1916 can be removed in order to define a sensor window 1922. The sensor window 1922 can be covered with the sensor membrane 1924.

The example of a pressure sensor 1900 of FIG. 19 can include four FBGs (e.g., FBGs 1-4). FBGs 3 and 4 can form a phase-shifted FBG structure, such as for sensing temperature. The change in phase-shift between FBG 3 and FBG 4 can be detected and quantified, and the change in temperature can be determined from the quantified phase-shift, such as described above.

The pressure sensor 1900 can further include Fabry-Perot gratings FBG 1 and FBG 2, which can be used to sense changes in pressure. The Fabry-Perot gratings FBG 1 and FBG 2 can create a phase shift that can be tracked in a manner similar to that described above. That is, a notch can be created in the wavelength response to the Fabry-Perot gratings FBG 1 and FBG 2, as shown and described in detail above. A point on a slope of the notch can be set and tracked, a phase shift can be detected and quantified, and the change in pressure can be determined from the quantified phase-shift, such as described in detail above.

The pressure sensor 1900 can define a cavity 1926, e.g., filled with air, laterally below the sensor membrane 1924 and the optical fiber 1902. The sensor membrane 1924 and the cavity 1926 can concentrate a stress in the area between the Fabry-Perot gratings FBG 1 and FBG 2, which can enhance the sensitivity of the pressure sensor 1900.

Figure 20:
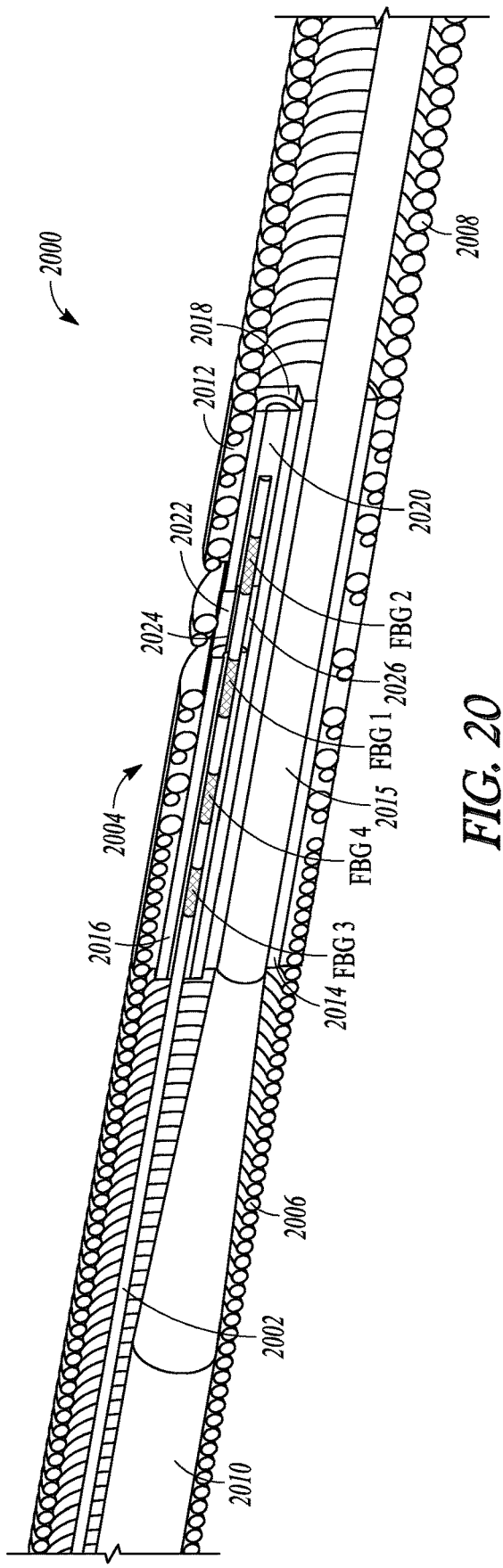
FIG. 20 depicts another example of a pressure sensor that can be used to implement various techniques of this disclosure.

FIG. 20 depicts another example of a pressure sensor that can be used to implement various techniques of this disclosure. FIG. 20 depicts another example of a pressure sensor that can be used to implement various techniques of this disclosure. The example of a pressure sensor 2000 depicted in FIG. 20 can provide an example standalone pressure sensor that can use one or more Fabry-Perot grating arrangements.

FIG. 20 is an example of a perspective cross-sectional view of an optical fiber pressure sensor 2000 that can include an optical fiber 2002 that can be configured to transmit one or more optical sensing signals and a temperature compensated Fiber Bragg Grating (FBG) interferometer 2004 in optical communication with the optical fiber 2002. The FBG interferometer 2004 can be configured to receive pressure, e.g., from pressure waves, and to modulate, in response to the received pressure, the optical sensing signal.

The example of a pressure sensor 2000 of FIG. 20 can include four FBGs (e.g., FBGs 1-4.) FBGs 3 and 4 can form a phase-shifted FBG structure, such as for sensing temperature. The change in phase-shift between FBG 3 and FBG 4 can be detected and quantified, and the change in temperature can be determined from the quantified phase-shift, such as described above.

The pressure sensor 2000 can further include Fabry-Perot gratings FBG 1 and FBG 2, which can be used to sense changes in pressure. Similar to the phase-shift grating structures described above with respect to FIG. 10D, the Fabry-Perot gratings FBG 1 and FBG 2 can create a phase shift that can be tracked in a manner similar to that described above. That is, a notch can be created in the wavelength response to the Fabry-Perot gratings FBG 1 and FBG 2, as shown and described in detail above. A point on a slope of the notch can be set and tracked, a phase shift can be detected and quantified, and the change in pressure can be determined from the quantified phase-shift, such as described in detail above.

The pressure sensor 2000 of FIG. 20 can further include a proximal coil 2006, a distal coil 2008, and a guidewire 2010. The proximal and distal coils 2006, 2008 can provide additional flexibility to aid advancement of the pressure sensor 2000 through tortuous pathways. In one example, the proximal and distal coils 2006, 2008 can be affixed together via a mechanical joint 2012, e.g., via solder or adhesive. The FBG interferometer 2004 can, in some examples, be positioned underneath the mechanical joint 2012 to provide additional protection to the FBG interferometer 2004.

The pressure sensor 2000 of FIG. 20 can further include a tubular housing 2014 that can be disposed about the guidewire 2010 and underneath the mechanical joint 2012. The housing 2014 can be affixed to the guidewire 2010 via a mechanical joint 2015. In addition, the pressure sensor 2000 can include a sensor tube 2016 disposed within the housing 2014 and disposed about a distal portion of the optical fiber 2002. In contrast to the tubular housing of FIG. 19, the tubular housing 2014 of FIG. 20 can define a lumen 2018 that extends longitudinally through the housing 2014. The sensor tube 2016 of FIG. 20 can be positioned within the lumen 2018. To provide support to the optical fiber 2002, a fiber support 2020 can be disposed about the optical fiber 2002 between the sensor tube 2016 and the optical fiber 2002.

To allow the received pressure to reach the optical fiber 2002, a portion of the sensor tube 2016 can be removed in order to define a sensor window 2022. The sensor window 2022 can be covered with a sensor membrane 2024.

The example of a pressure sensor 2000 of FIG. 20 can include four FBGs (e.g., FBGs 1-4). FBGs 3 and 4 can form a phase-shifted FBG structure, such as for sensing temperature. The change in phase-shift between FBG 3 and FBG 4 can be detected and quantified, and the change in temperature can be determined from the quantified phase-shift, such as described above.

The pressure sensor 2000 can further include Fabry-Perot gratings FBG 1 and FBG 2, which can be used to sense changes in pressure. The Fabry-Perot gratings FBG 1 and FBG 2 can create a phase shift that can be tracked in a manner similar to that described above. That is, a notch can be created in the wavelength response to the Fabry-Perot gratings FBG 1 and FBG 2, as shown and described in detail above. A point on a slope of the notch can be set and tracked, a phase shift can be detected and quantified, and the change in pressure can be determined from the quantified phase-shift, such as described in detail above.

The pressure sensor 2000 can define a cavity 2026, e.g., filled with air, laterally below the sensor membrane 2024 and the optical fiber 2002. The sensor membrane 2024 and the cavity 2026 can concentrate a stress in the area between the Fabry-Perot gratings FBG 1 and FBG 2, which can enhance the sensitivity of the pressure sensor 2000.

FIGS. 21A-21D depict another example of a guidewire in combination with an optical fiber pressure sensor. FIG. 21A is an example of a partial cutaway view illustrating a combination 2100 of a guidewire 2102 and an optical fiber 2104 attached to an optical fiber pressure sensor 2106 (FIG. 21C).

In one example, the guidewire 2102 can be substantially similar to the guidewire shown and described in U.S. Pat. No. 5,341,818 to Abrams et al. and assigned to Abbott Cardiovascular Systems, Inc. of Santa Clara, Calif., the entire contents of which being incorporated herein by reference. The guidewire 2102 can include a proximal portion 2108 and a distal portion 2110. The distal portion 2110 can be formed at least partially of superelastic materials. The guidewire 2102 can further include a tubular connector 2112 that can connect a distal end 2114 of the proximal portion 2108 and a proximal end 2116 of the distal portion 2110.

The guidewire 2102 can further include a core wire 2118 having an elongated portion 2120 and a tapered portion 2122 extending distally beyond the elongated portion 2120. In addition, the guidewire 2102 can include a proximal coil 2124 disposed about the elongated portion 2120 and a distal coil 2126 disposed about a portion of each of the elongated portion 2120 and the tapered portion 2122 and extending distally beyond the tapered portion 2122. The proximal coil 2124 and the distal coil 2126 can be joined together via a mechanical joint 2128, e.g., solder or adhesive. The guidewire 2102 can further include a distal plug 2130, about which a portion of the distal coil 2126 can be wound, or a conventional solder tip. Additional information regarding the components and construction of the guidewire 2102 can be found in U.S. Pat. No. 5,341,818.

Regarding construction of the combination 2100 of the guidewire 2102 and the optical fiber 2104 attached to an optical fiber pressure sensor 2106 (FIG. 21C), in one example, a narrow, shallow channel or groove 2132 (FIG. 21B) can be cut into the outer wall of the components that form the guidewire 2102, e.g., the core wire 2118 and the tubular connector 2112. The optical fiber 2104 can be positioned within the groove 2132. Due to the relatively small dimensions of optical fiber 2104, the dimensions of the groove 2132 can have minimal impact on the performance of the guidewire 2102.

The groove 2132 can extend along the length of the guidewire 2102 substantially parallel to a longitudinal axis of the guidewire 2102. In another example, the groove 2132 can spiral about the guidewire 2102, e.g., a helically axially extending groove. In other examples, the groove 2132 can extend along a portion of the length of the guidewire 2102 substantially parallel to a longitudinal axis of the guidewire 2102 and then the groove 2132 can spiral about another portion of the length of the guidewire 2102, e.g., a helically axially extending groove. The pitch of the spiral can be varied along the length of the guidewire.

The groove 2132 can be fabricated using various techniques that include, but are not limited to, etching, machining, and laser ablation. In addition, the groove 2132 can be fabricated at various stages during the construction of the guidewire 2102, e.g., before or after applying a coating to the guidewire 2102.

The optical fiber 2104 can be bonded to the groove 2132 using various techniques. For example, the optical fiber 2104 can be bonded to the groove 2132 by applying a hot melt adhesive to the optical fiber 2104 prior to positioning the optical fiber 2104 in the groove 2132 and then subsequently applying heat.

In other examples, rather than a groove 2132 that is cut into the outer wall of the components that form the guidewire 2102, the guidewire 2102 can define a lumen (not depicted) that extends along a portion of the length of the guidewire 2102 substantially parallel to a longitudinal axis of the guidewire 2102. The lumen can be coaxial with the longitudinal axis of the guidewire 2102, or the lumen can be radially offset from the longitudinal axis of the guidewire 2102. The optical fiber 2104 can extend along the length of the guidewire 2102 through the lumen. The dimensions of the lumen can have minimal impact on the performance of the guidewire 2102.

In another example, the guidewire 2102 can be constructed to include an annular gap (not depicted) between the proximal coil 2124 and the elongated portion 2120. The optical fiber 2104 can then extend along the length of the elongated portion 2120 between an outer surface of the elongated portion 2120 and an inner surface of the proximal coil 2124. The optical fiber 2104 can be wound about the elongated portion 2120. In some examples, the optical fiber 2104 can be secured to the elongated portion 2120, e.g., via an adhesive.

FIG. 21B is an example of a cross-sectional view of the combination 2100 of FIG. 21A, such as taken along section B-B of FIG. 21A. The guidewire 2102, e.g., a solid guidewire, can include the fabricated groove 2132. FIG. 21B illustrates the optical fiber 2104 positioned within the groove 2132 of the core wire 2118 of the guidewire 2102.

FIG. 21C is an example of a cross-sectional view of the combination 2100 of FIG. 21A, such as taken along section E-E of FIG. 21A. More particularly, FIG. 21C depicts another example of a pressure sensor 2106 that can be used to implement various techniques of this disclosure.

The optical fiber pressure sensor 2106 can include the optical fiber 2104 that can be configured to transmit one or more optical sensing signals and a temperature compensated Fiber Bragg Grating (FBG) interferometer 2134 in optical communication with the optical fiber 2104. The FBG interferometer 2134 can be configured to receive pressure, e.g., from pressure waves, and to modulate, in response to the received pressure, the optical sensing signal.

The example of a pressure sensor 2106 of FIG. 21C can further include FBGs (not depicted) similar to those described in detail above with respect to various examples of pressure sensors, e.g., FIG. 10D, which can be used to sense changes in pressure. The FBGs can create a phase shift that can be tracked in a manner similar to that described above.

The pressure sensor 2106 of FIG. 21C can further include the proximal coil 2124 and the distal coil 2126. The proximal and distal coils 2124, 2126 can provide flexibility to aid advancement of the pressure sensor 2106 through tortuous pathways. In one example, the proximal and distal coils 2124, 2126 can be affixed together via a mechanical joint 2136. The FBG interferometer 2134 can, in some examples, be positioned underneath the mechanical joint 2136 to provide additional protection to the FBG interferometer 2134.

As indicated above, the guidewire 2102 can be fabricated with a groove 2132 (FIG. 21B) to which the optical fiber 2104 can be attached. A portion of the optical fiber 2104 can extend underneath the mechanical joint 2136. To allow the received pressure to reach the optical fiber 2104, a portion of the mechanical joint 2136 can be removed in order to define a sensor window, shown generally at 2138. The sensor window 2138 can be covered with the sensor membrane 2140.

In the example depicted in FIG. 21C, the pressure sensor 2106 can be constructed by fabricating a small cavity 2142 in the core wire 2118 that is in communication with the groove 2132 at the distal end of the optical fiber 2104. The cavity 2142 can, for example, be 100 microns in diameter by 100 microns in depth. The guidewire 2102 can be constructed of the superelastic material, or a different super stiff material may be substituted at this location (not depicted), for example, aluminum oxide ($Al_2O_3$) or Alumina ceramic which can be precision molded to define the cavity 2142 and the groove 2132.

The pressure sensor 2106 can further include a microballoon 2144 placed into the cavity 2142. In some examples, an adhesive (not depicted) can be placed in the cavity 2142 to secure the microballoon 2144 in place. The microballoon 2144 can be filled with a gas, sealed, and heat expanded such that, when expanded, the microballoon 2144 can fill the cavity 2142 and maintain a sealed reference chamber. If an upper surface of the microballoon 2144 is constricted during its expansion, a flat diaphragm can be achieved. The optical fiber 2104 with FBGs can be positioned in the groove 2132 and across the flat diaphragm of the microballoon 2144.

The remaining space of the cavity 2142 and the groove 2132 can be filled with an adhesive (not depicted) such as silicone to capture the optical fiber 2104, to attach the optical fiber 2104 to the guidewire 2102, to attach the optical fiber 2104 to the microballoon 2144, and to define a relatively thin silicone diaphragm in mechanical communication with the chamber defined by the microballoon 2144 where the optical fiber 2104 is embedded. As a pressure is applied, each of the silicone, the optical fiber 2104, and the microballoon 2144 can flex due to compression of the sealed chamber. The flexing can transmit the received pressure to the FBG interferometer 2134, which can create a responsive phase shift between FBGs (not depicted) that can be tracked in a manner similar to that described above.

FIG. 21D is an example of a cross-sectional view of the combination 2100 of FIG. 21A, such as taken along section A-A of FIG. 21A. More particularly, FIG. 21D depicts a cross-sectional view of the pressure sensor 2106 of FIG. 21C. As seen in FIG. 21D and as described above with respect to FIG. 21C, the pressure sensor 2106 of FIG. 21C can include the microballoon 2144 positioned within the cavity 2142. The optical fiber 2104 with FBGs can be positioned in the groove 2132 and across the flat diaphragm 2146 of the microballoon 2144.

Any of optical fiber pressure sensors described in this disclosure can be combined with the guidewire 2102 shown and described above with respect to FIG. 21A and in U.S. Pat. No. 5,341,818. Further, the techniques of this disclosure are not limited to the use of a single sensor in combination with a guidewire, e.g., guidewire 2102. Rather, two or more sensors, e.g., pressure sensors, can be combined with a guidewire by defining sensor regions in which each of the two or more sensors can function at a respective, unique wavelength and can be addressed accordingly by a laser matching the wavelength of the respective sensor. Each laser can be multiplexed onto the optical fiber using standard techniques, e.g., wavelength-division multiplexing (WDM), found in telecommunications systems.

In another example, the guidewire 2102 of FIG. 21A can be combined with other sensor techniques. For example, the same guidewire can be used for both intravascular ultrasound (IVUS) imaging and pressure sensing by using the imaging sensor configurations described in U.S. Pat. No. 7,245,789 to Bates et al., and assigned to Vascular Imaging Corp, the entire contents of which being incorporate herein by reference. By way of specific example, one of the optical fibers in a 32 fiber arrangement can extend distally beyond an imaging sensor region, where an optical fiber pressure sensor, such as any of the optical fiber pressure sensors described in this disclosure, can be included that utilizes a different wavelength than that used by the imaging arrangement.

Figure 22:
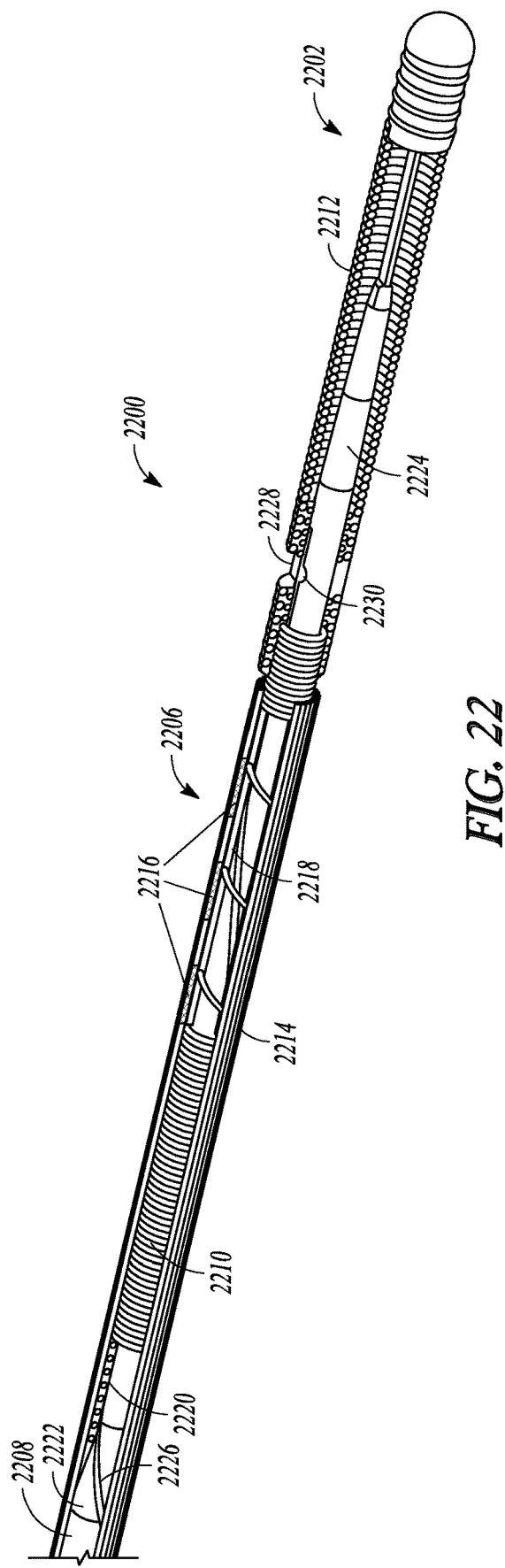
FIG. 22 depicts an example of a combination of a guidewire with an optical fiber pressure sensor and an imaging sensor, in accordance with this disclosure.

FIG. 22 depicts an example of a combination 2200 of a guidewire 2202 with an optical fiber pressure sensor 2204 and an imaging sensor 2206, e.g., using the imaging sensor configurations described in U.S. Pat. No. 7,245,789. In particular, FIG. 22 is an example of a perspective partial cutaway view of the combination 2200.

The guidewire 2202 is similar in construction to the guidewire 2102 described above with respect to FIG. 21A, and as shown and described in U.S. Pat. No. 5,341,818. The guidewire 2202 can include a core wire 2208, a proximal coil 2210, and a distal coil 2212.

The imaging sensor 2206 can include an optical fiber ribbon 2214 having a plurality of optical fibers, e.g., 32 optical fibers, disposed about the core wire 2208 of the guidewire 2202, and a plurality of imaging gratings 2216 to couple light into and/or out of one or more respective optical fibers of the ribbon 2214.

The guidewire 2202 can further include a backing 2218 disposed about the core wire 2208 and positioned between the core wire 2208 and the optical fiber ribbon 2214. In addition, the guidewire 2202 can include a mechanical joint 2220 for joining a proximal portion 2222 of the guidewire 2202 to a distal portion 2224 of the guidewire 2202.

In one example, the pressure sensor 2204 can be similar to the pressure sensor 2106 of FIG. 21C. For purposes of conciseness, the pressure sensor 2204 will not be described in detail again. The pressure sensor 2204 can include a single optical fiber 2226 that extends longitudinally along the length of the guidewire 2202, e.g., within a groove in the outer surface of the core wire 2208 and underneath the optical fiber ribbon 2214. The pressure sensor 2204 can further include a pressure sensing window 2228 and pressure sensor membrane 2230, as described in detail above. The pressure sensor 2204 of FIG. 22 is not limited to the design of the pressure sensor 2106 of FIG. 21C. Rather, any of the pressure sensor configurations described in this disclosure can be applied to the combination 2200.

In one example, an outer diameter of the guidewire 2202 can be reduced along the length of the guidewire 2202 up to the distal coil 2212 to allow the optical fiber ribbon 2214 to be disposed about the outer surface of the guidewire 2202. By way of specific example, the outer diameter of the proximal coil 2210 can be reduced from 0.014" to 0.011" and the pressure sensor 2204 can be incorporated with the guidewire 2202 either in a surface groove or a coaxial hole of the core wire 2208. The optical fiber ribbon 2214, e.g., a 32 optical fiber arrangement, of the imaging sensor 2206 can then be positioned over the 0.011" outer diameter of the guidewire 2202 so that the assembly contains 33 optical fibers, for example. This configuration can separate the multiplexing requirements of the imaging sensor 2206 and the pressure sensor 2204, and can allow the pressure sensor 2204 to operate at any wavelength, including that of the imaging sensor 2206.

Figure 23A:
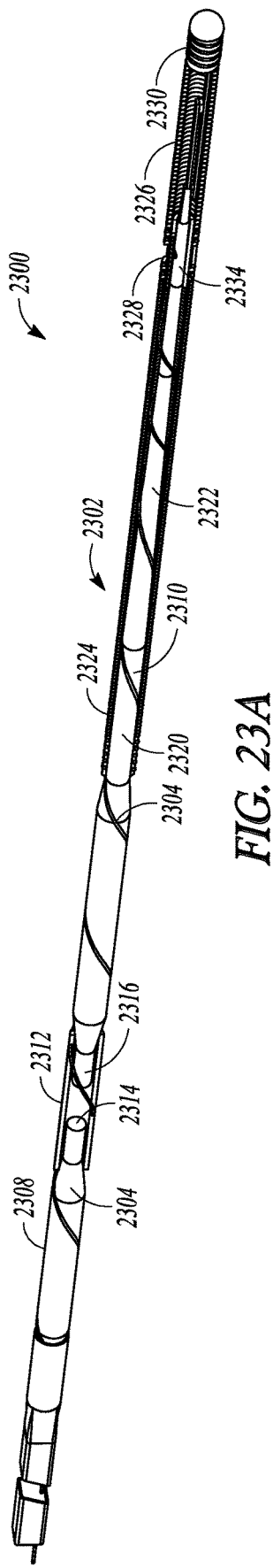
FIGS. 23A-23B depict another example of a guidewire in combination with an optical fiber pressure sensor, in accordance with this disclosure.
Figure 23B:
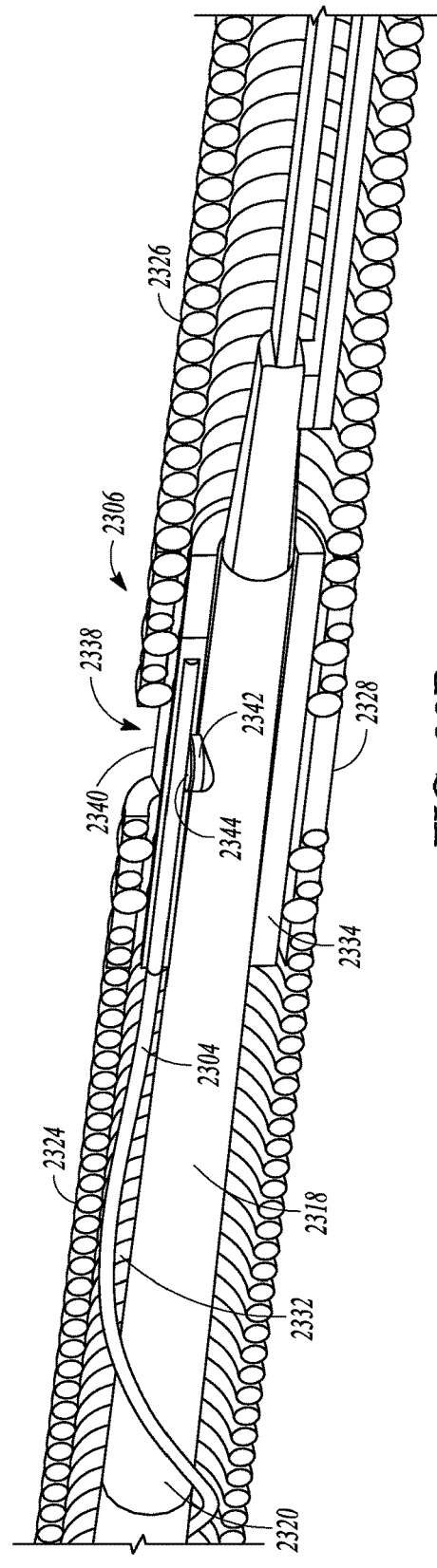

FIGS. 23A-23B depict another example of a guidewire in combination with an optical fiber pressure sensor. FIG. 23A is an example of a partial cutaway view illustrating a combination 2300 of a guidewire 2302 and an optical fiber 2304 attached to an optical fiber pressure sensor 2306 (FIG. 23B).

The guidewire 2302 can include a proximal portion 2308 and a distal portion 2310. The distal portion 2310 can be formed at least partially of superelastic materials. The guidewire 2302 can further include a tubular connector 2312 that can connect a distal end 2314 of the proximal portion 2308 and a proximal end 2316 of the distal portion 2310.

The guidewire 2302 can further include a core wire 2318 having an elongated portion 2320 and a tapered portion 2322 extending distally beyond the elongated portion 2320. In addition, the guidewire 2302 can include a proximal coil 2324 disposed about the elongated portion 2320 and the tapered portion 2322. The guidewire 202 can also include a distal coil 2326 disposed about a portion of the tapered portion 2322 and extending distally beyond the tapered portion 2322. The proximal coil 2324 and the distal coil 2326 can be joined together via a mechanical joint 2328, e.g., solder or adhesive. The guidewire 2302 can further include a distal plug 2330, about which a portion of the distal coil 2326 can be wound, or a conventional solder tip.

Regarding construction of the combination 2300 of the guidewire 2302 and the optical fiber 2304 attached to an optical fiber pressure sensor 2306, in one example, a narrow, shallow channel or groove (not depicted) can be cut into the outer wall of the components that form the guidewire 2302, e.g., the core wire 2318 and the tubular connector 2312. The optical fiber 2304 can be positioned within the groove. Due to the relatively small dimensions of optical fiber 2304, the dimensions of the groove can have minimal impact on the performance of the guidewire 2302.

The groove can extend along the length of the guidewire 2302 substantially parallel to a longitudinal axis of the guidewire 2302. In another example, the groove can spiral about the guidewire 2302, e.g., a helically axially extending groove. In other examples, the groove can extend along a portion of the length of the guidewire 2302 substantially parallel to a longitudinal axis of the guidewire 2302 and then the groove can spiral about another portion of the length of the guidewire 2302, e.g., a helically axially extending groove. The pitch of the spiral can be varied along the length of the guidewire.

The groove can be fabricated using various techniques that include, but are not limited to, etching, machining, and laser ablation. In addition, the groove can be fabricated at various stages during the construction of the guidewire 2302, e.g., before or after applying a coating to the guidewire 2302.

The optical fiber 2304 can be bonded to the groove using various techniques. For example, the optical fiber 2304 can be bonded to the groove by applying a hot melt adhesive to the optical fiber 2304 prior to positioning the optical fiber 2304 in the groove and then subsequently applying heat.

The guidewire 2302 can be constructed to include an annular gap, shown in FIG. 23B at 2332, between the proximal coil 2324 and the portions 2320, 2322. The optical fiber 2304 can then extend along the length of the portions 2320, 2322 of the distal portion 2310 between an outer surface of the portions and an inner surface of the proximal coil 2324. The optical fiber 2304 can be wound about the elongated portion 2320. In some examples, the optical fiber 2304 can be secured to the elongated portion 2320, e.g., via an adhesive.

The combination 2300 can further include a sleeve 2334 disposed about the core wire 2318 and underneath the mechanical joint 2328, to receive a distal portion of the optical fiber 2304. In one example, sleeve 2334 can be constructed of aluminum oxide ($Al_2O_3$), or other stiff material. The core wire 2318 can taper as it extends underneath the mechanical joint.

FIG. 23B is an example of a partial cutaway view of a portion of the combination 2300 of FIG. 23A. More particularly, FIG. 23B depicts another example of a pressure sensor 2306 that can be used to implement various techniques of this disclosure.

The optical fiber pressure sensor 2306 can include the optical fiber 2304 that can be configured to transmit one or more optical sensing signals and a temperature compensated Fiber Bragg Grating (FBG) interferometer 2334 in optical communication with the optical fiber 2304. The FBG interferometer 2334 can be configured to receive pressure, e.g., from pressure waves, and to modulate, in response to the received pressure, the optical sensing signal.

The example of a pressure sensor 2306 of FIG. 23B can further include FBGs (not depicted) similar to those described in detail above with respect to various examples of pressure sensors, e.g., FIG. 10D, which can be used to sense changes in pressure. The FBGs can create a phase shift that can be tracked in a manner similar to that described above.

The pressure sensor 2306 of FIG. 23B can further include the proximal coil 2324 and the distal coil 2326. The proximal and distal coils 2324, 2326 can provide flexibility to aid advancement of the pressure sensor 2306 through tortuous pathways. In one example, the proximal and distal coils 2324, 2326 can be affixed together via a mechanical joint 2328. The FBG interferometer 2334 can, in some examples, be positioned underneath the mechanical joint 2328 to provide additional protection to the FBG interferometer 2334.

As indicated above, the guidewire 2302 can be constructed to include an annular gap 2332 between the proximal coil 2324 and the portion 2320 to allow the optical fiber 2304 to extend along the length of the portion 2320. The sleeve 2334 can include a lumen, groove, or pocket to receive the distal end of the optical fiber 2304. To allow the received pressure to reach the optical fiber 2304, a portion of the mechanical joint 2328 and the sleeve 2334 can be removed in order to define a sensor window, shown generally at 2338. The sensor window 2338 can be covered with the sensor membrane 2340.

In the example depicted in FIG. 23B, the pressure sensor 2306 can be constructed by fabricating a small cavity 2342 in the core wire 2318. The cavity 2342 can, for example, be 100 microns in diameter by 100 microns in depth. The guidewire 2302 can be constructed of the superelastic material, or a different super stiff material may be substituted at this location (not depicted), for example, $Al_2O_3$, or Alumina ceramic which can be precision molded to define the cavity 2342.

The pressure sensor 2306 can further include a microballoon 2344 placed into the cavity 2342. In some examples, an adhesive (not depicted) can be placed in the cavity 2342 to secure the microballoon 2344 in place. The microballoon 2344 can be filled with a gas, sealed, and heat expanded such that, when expanded, the microballoon 2344 can fill the cavity 2342 and maintain a sealed reference chamber. If an upper surface of the microballoon 2344 is constricted during its expansion, a flat diaphragm can be achieved. The optical fiber 2304 with FBGs can be positioned in the sleeve 2334 and across the flat diaphragm of the microballoon 2344.

As a pressure is applied, the optical fiber 2304 and the microballoon 2344 can flex due to compression of the sealed chamber. The flexing can transmit the received pressure to the FBG interferometer 2334, which can create a responsive phase shift between FBGs (not depicted) that can be tracked in a manner similar to that described above.

Figure 24:
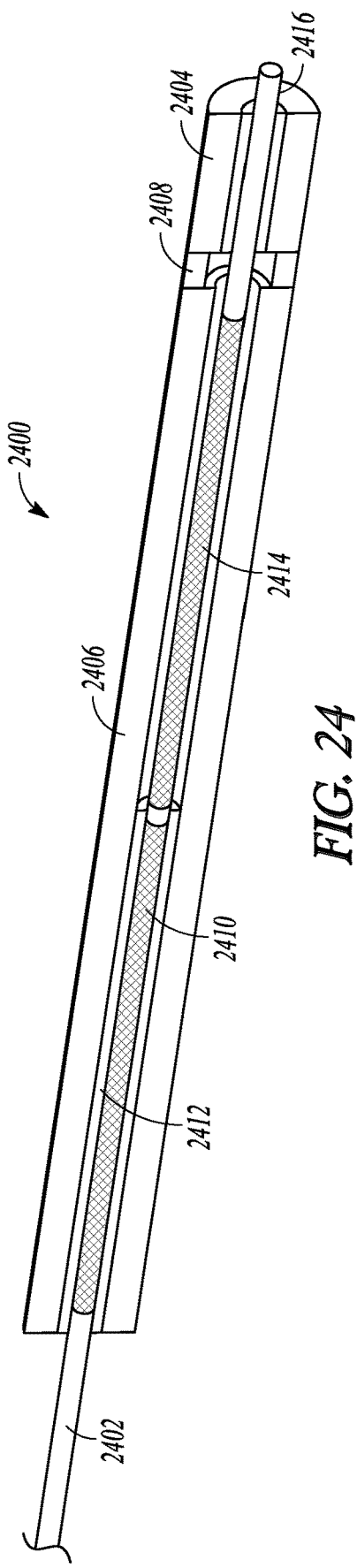
FIG. 24 shows an example of a portion of a concentric pressure sensor assembly.

FIG. 24 shows an example of a portion of a concentric pressure sensor assembly 2400. The concentric pressure sensor assembly 2400 can include or be coupled to an optical fiber 2402, such as a reduced-diameter longitudinally extending central optical fiber 2402. The concentric pressure sensor assembly 2400 can be located at or near a distal region of the optical fiber 2402. In an example, the pressure sensor assembly 2400 can include at least one Fabry-Perot interferometer, such as in the optical fiber 2402. The Fabry-Perot interferometer can modulate the wavelength of light in the optical fiber 2402, such as in response to environmental pressure variations that can stretch or compress the optical fiber 2402, e.g., longitudinally and linearly. The modulated light in the optical fiber 2402 can be used to communicate information about the environmental pressure variations at or near the distal end of the optical fiber 2402 to a proximal end of the optical fiber 2402, such as for coupling the resulting optical signal to an optoelectronic or other optical detector, which, in turn, can be coupled to electronic or optical signal processing circuitry, such as for extracting or processing the information about the sensed environmental pressure variations.

A distal portion of the optical fiber 2402 (e.g., more distal than the one or more Fabry-Perot interferometers) can be securely captured, anchored, or affixed, such as at a hard, solid, or inelastic distal disk assembly, distal endcap, or other distal anchor 2404, such as can be located at a distal end portion of the concentric pressure sensor assembly 2400. The hard, solid, or inelastic material (e.g., fused silica or other suitable material) of the distal anchor 2404 can be relatively inflexible, e.g., relative to the dimensional variation of the optical fiber 2402 in response to the targeted environmental pressure variations to be measured. In an illustrative example, any dimensional variation of the distal anchor 2404 can be less than or equal to $\frac{1}{20}$, $\frac{1}{100}$, or $\frac{1}{1000}$ of any dimensional variation of a pressure-sensing portion of the optical fiber 2402 measured in response to the targeted environmental pressure variations, such as the pressure variations that can be present in a percutaneous in vivo intravascular human blood pressure sensing application.

The tubular or other distal anchor 2404 can be attached to a hard, solid, or inelastic (e.g., fused silica) tubular or other housing 2406, such as by a soft, flexible, elastic, or compliant gasket 2408 that can be located therebetween. A first sensing region 2410 of the optical fiber 2402 can be securely captured, anchored, or affixed, to the housing 2406, such as via a tubular or other attachment (e.g., hardened epoxy or other adhesive) region 2412. A second sensing region 2414 of the optical fiber 2402 can be located within the housing 2406, such as suspended (e.g., freely or within a compliant material) between the encapsulator or attachment region 2412 and the hard distal anchor 2404. The suspended portion of the optical fiber 2402 can be installed or securely held longitudinally under tension. This can permit both positive and negative direction longitudinal displacement variations in the suspended portion of the optical fiber 2402, which, in turn, can permit sensing of both positive and negative environmental pressure variations, as explained herein.

The gasket 2408 material (e.g., medical grade silicone) can be relatively more flexible, soft, elastic, or compliant than the housing 2406 and than the distal anchor 2404, such as to allow longitudinal dimensional variation of gasket 2408 and the suspended second sensing region 2414 of the optical fiber 2402 in response to the targeted environmental pressure variations to be measured, such as the pressure variations that can be present in a percutaneous in vivo intravascular human blood pressure sensing application. The first sensing region 2410 can be securely fixed to the hard housing 2406 by the encapsulator or attachment region 2412, while the second sensing region 2414 can be suspended within the hard housing 2406 and subject to longitudinal dimensional variation (along with longitudinal dimensional variation of the compliant gasket 2408). Therefore, the first sensing region 2410 can be shielded from or made insensitive to environmental pressure variations, but sensitive to environmental temperature variations, while the second sensing region 2414 can be sensitive to both environmental pressure and temperature variations. In this way, light modulation in the first sensing region 2410 due to temperature variations can be measured and used to compensate for or null-out the light modulation effect of similar temperature variations experienced by the second sensing region 2414 that is being used to measure environmental pressure variations. In an illustrative example, the first sensing region 2410 can include a first Fabry-Perot interferometer, and the second sensing region 2414 can include a second Fabry-Perot interferometer. These respective interferometers can be written with different wavelengths. This can permit each interferometer to be individually separately addressed by selecting a corresponding wavelength of light to provide to the proximal end of the optical fiber 2402 to perform the selective individual addressing of the interferometers.

FIG. 24 can be conceptualized as an arrangement in which at least one optical fiber sensing region can be suspended from or between two anchors (e.g., hard tubes 2404, 2406) that can be separated from each other by a compliant region (e.g., gasket 2408) that can allow the anchoring tubes 2404, 2406 (and hence the suspended portion of the optical fiber 2402) to experience longitudinal displacement in response to environmental pressure variations. Based on finite element modeling (FEM) simulation analysis and experimental laboratory data obtained from prototypes, corresponding to the arrangement illustrated in FIG. 24, a pressure sensitivity can be obtained that can be at least 100 to 150 times the pressure sensitivity of an optical fiber without such arrangement of hard tubes 2404, 2406 separated from each other by the compliant gasket 2408.

In an illustrative example, the entire pressure sensor assembly 2400 can be less than or equal to 1.5 millimeters in length, such as less than or equal to 1.0 millimeter in length. The pressure sensor assembly 2400 can have an outer diameter that can be less than or equal to 125 micrometers. For comparison, 125 micrometers is the outer diameter of a typical single standard optical fiber as used in telecommunications. The tubular housing 2406 can have an inner lumen diameter of about 50 micrometers. In an example, the entire pressure sensor assembly 2400 can be conveniently incorporated within a percutaneous or other guidewire, such as can be used for guiding an intravascular device (e.g., a stent, such as a coronary stent) to a desired location within a blood vessel. For example, the entire pressure sensor assembly 2400 can be included within a solder or other joint of such a guidewire, such as between spring coils forming a body of the guidewire. Using fused silica or other glass components for all or portions of the tubular housing 2406 or the fused silica distal anchor 2404 can provide components that can provide a good matching of the temperature coefficient of expansion of these materials to the temperature coefficient of expansion of the material of the optical fiber 2402.

The arrangement shown in the illustrative example of FIG. 24 can advantageously be durable, can be easy to make, can perform well such as in detecting and amplifying an environmental pressure variation, or can consistently be made in a small form factor.

Figure 25:
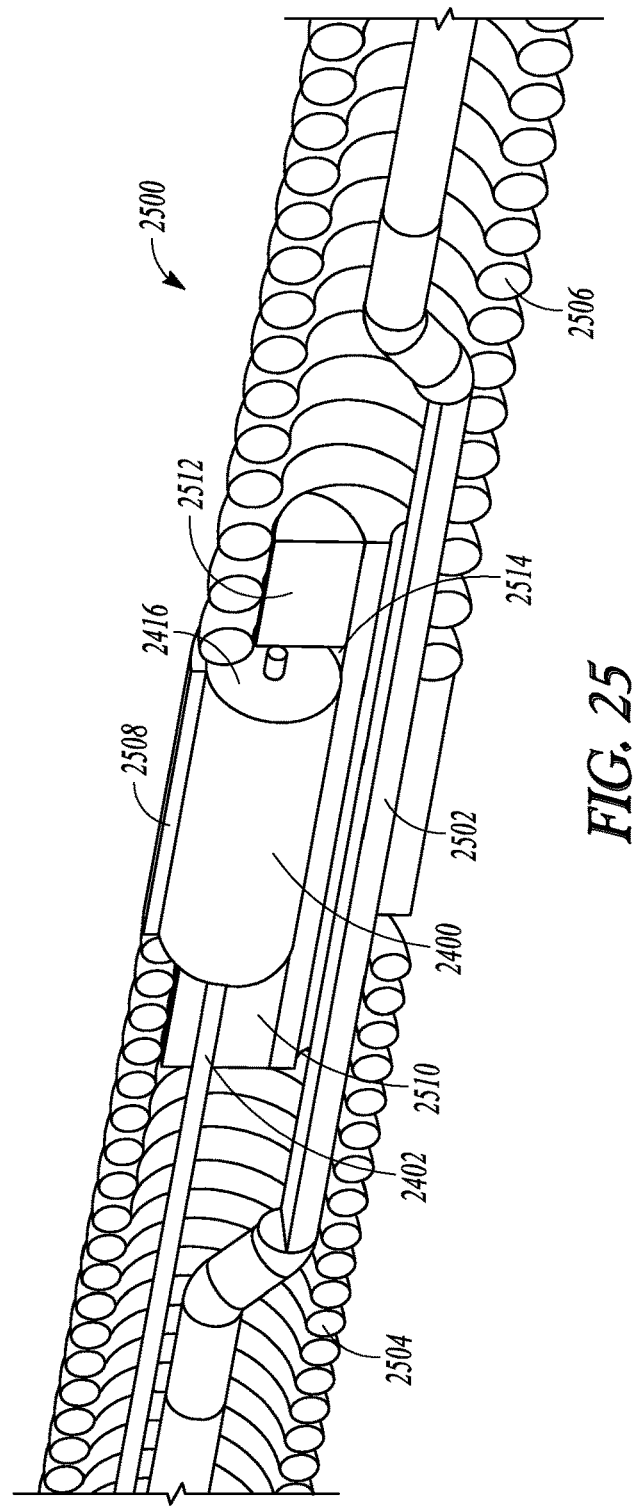
FIG. 25 shows an example of the pressure sensor assembly as it can be prefinished and included or otherwise incorporated into a percutaneous intravascular guidewire assembly.

FIG. 25 shows an example of the pressure sensor assembly 2400 as it can be prefinished and included or otherwise incorporated into a percutaneous intravascular guidewire assembly 2500. The guidewire assembly 2500 can include a core guidewire 2502, a flexible proximal spring coil region 2504 and a flexible distal spring coil region 2506 that can terminate at a rounded and atraumatic distal tip. A generally cylindrical or other connector block 2508 can be included between and interconnecting the proximal spring coil region 2504 and the distal spring coil region 2506. The connector block 2508 can include a reduced diameter proximal end seat region 2510 and a reduced diameter distal end seat region 2512, about which windings of the flexible proximal spring coil region 2504 and a flexible distal spring coil region 2506 can respectively be wound, such as with their outer circumferences flush with an outer circumference of a midportion of the connector block 2508 between the proximal end seat region 2510 and the reduced diameter distal end seat region 2512. The connector block 2508 can provide a housing for the pressure sensor assembly 2400. The optical fiber 2402 can extend proximally from the pressure sensor assembly 2400 in the connector block 2508 through the proximal spring coil region 2504, such as to an optical connector at a proximal end of the guidewire assembly 2500, where it can be optically coupled to optical, electronic, or optoelectronic signal generation or processing circuitry. The core guidewire 2502 of the guidewire assembly 2500 can bend or jog off of the concentric longitudinal axis of the guidewire assembly 2500, such as at or near the connector block 2508, if needed to allow enough room for the pressure sensor assembly 2500 to be housed within the connector block 2508 while also allowing passage of the core guidewire 2502 through the connector block 2508 in such a lateral offset arrangement.

The connector block 2508 can provide a lateral axis portal 2514 that can be located beyond a distal end region 2516 of the pressure sensor assembly 2400 such as to leave a distal end region 2516 of the pressure sensor assembly 2400 exposed to nearby environmental pressures to be measured, while providing a ceramic or other hard protective circumferential housing region that can protect the pressure sensor assembly 2400 from lateral pressure or lateral torque that may otherwise influence the pressure sensor measurement to be obtained by longitudinal spatial variations of the pressure sensor assembly 2400.

Figure 26:
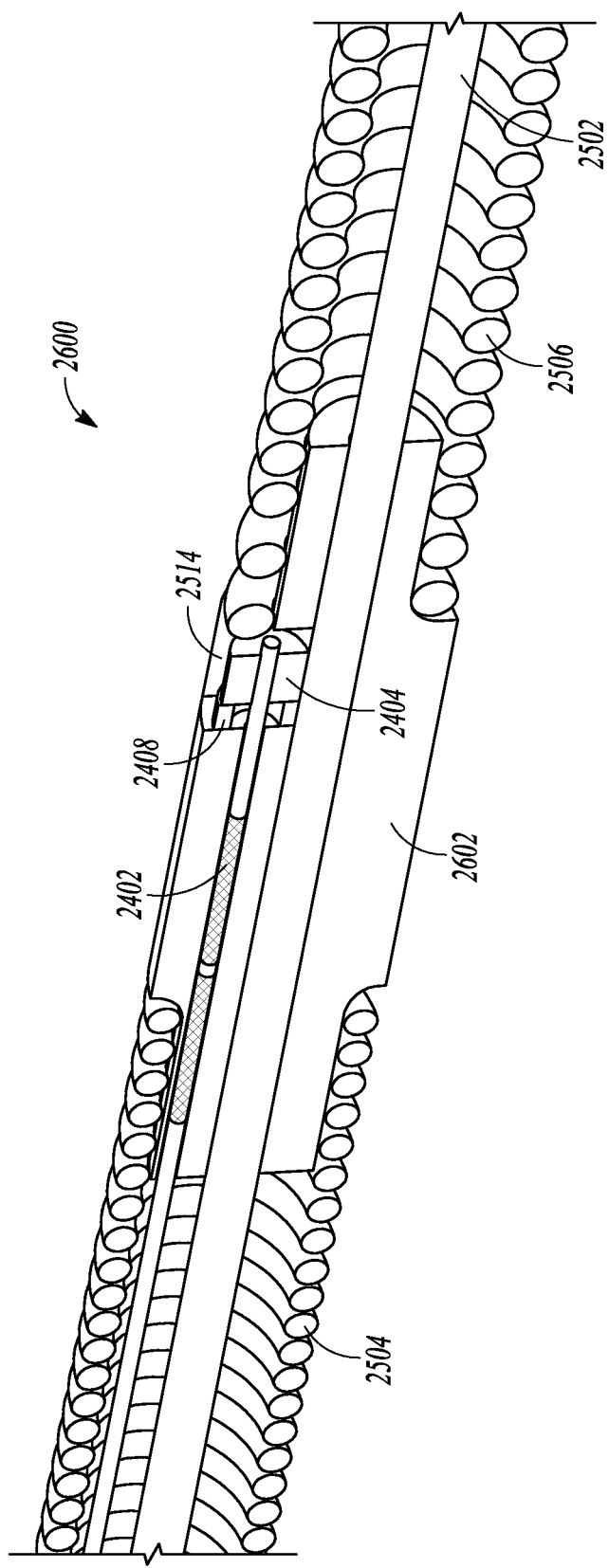
FIG. 26 shows an example illustrating how components of the pressure sensor assembly can be integrated into or otherwise incorporated into a percutaneous intravascular guidewire assembly.

FIG. 26 shows an example illustrating how components of the pressure sensor assembly 2400 can be integrated into or otherwise incorporated into a percutaneous intravascular guidewire assembly 2600. FIG. 26 is similar to FIG. 25 in some respects, but in FIG. 26 the connector block 2602 can provide a concentric axially aligned longitudinal passage for the core guidewire 2502, such that it need not bend or jog as shown in FIG. 25. This can help preserve or utilize the mechanical properties or characteristics of the core guidewire 2502 or those of the guidewire assembly 2600. One or more components of the pressure sensor assembly 2400 can be laterally offset from the concentric axially aligned core guidewire 2502, such as within the connector block 2602. The connector block 2602 can include a lateral axis portal 2514. The distal anchor 2404 and the gasket 2408 can be located in or near the lateral axis portal 2514, and can optionally be laterally recessed or otherwise shielded from lateral pressure or torque that may otherwise influence the pressure sensor measurement to be obtained by longitudinal spatial variations of the integrated components of the pressure sensor assembly 2400, such as explained above with respect to FIG. 25. The connector block 2602 can be constructed with a passage for the optical fiber 2402 sized, shaped, or otherwise configured such as to provide a first sensing region 2410 of the optical fiber 2402 that can be affixed to a housing provided by the connector block 2602, such as explained herein. A second sensing region 2414 of the optical fiber 2402 can be suspended within a housing provided by the connector block 2602, such as explained herein. The optical fiber 2402 can extend outward from the connector block 2602 proximally, such as through the proximal spring coil region 2504, such as with the optical fiber 2402 extending so as to be laterally offset from a longitudinal central axis of the guidewire assembly 2600.

Figure 27:
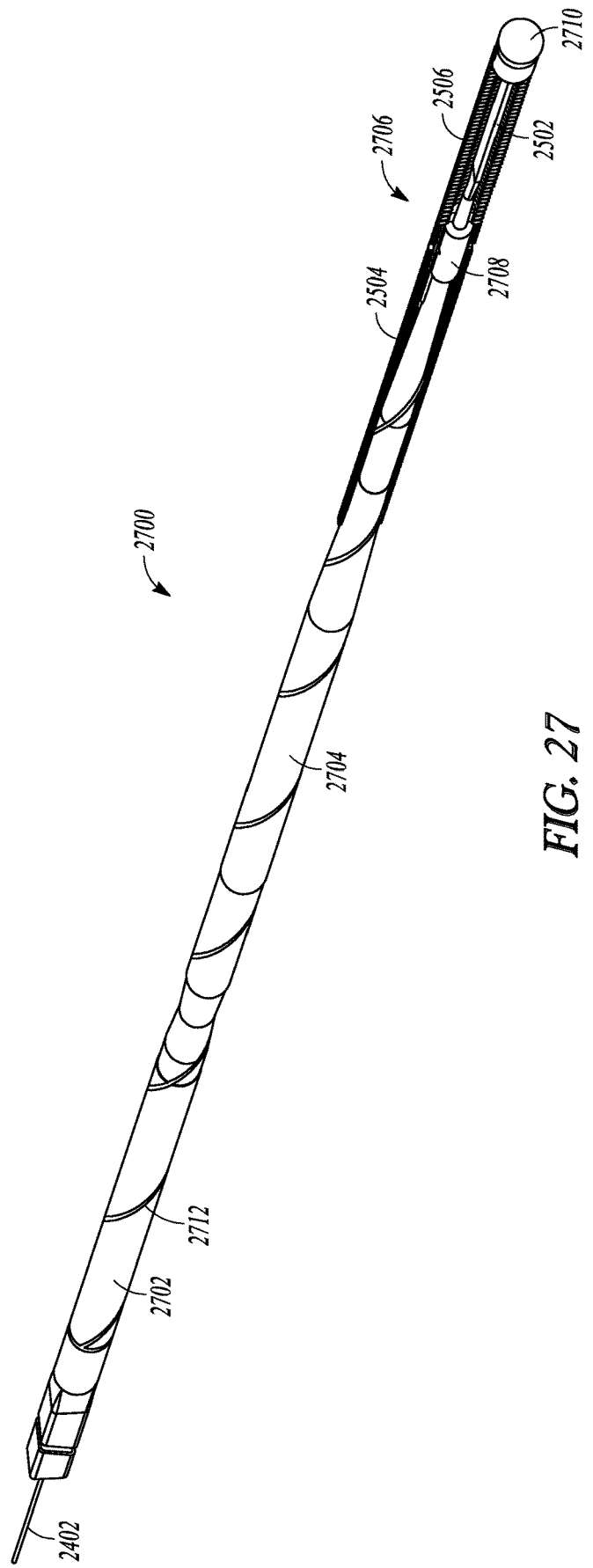
FIG. 27 shows an example in which components of the pressure sensing assembly can be retrofitted to or otherwise integrated into an existing guidewire assembly.

FIG. 27 shows an example in which components of the pressure sensing assembly 2400 can be retrofitted to or otherwise integrated into an existing guidewire assembly 2700, such as a RUNTHROUGH® guidewire, available from Terumo Kabushiki Kaisha, also known as Terumo Corp. The guidewire assembly 2700 can include a proximal region 2702, that can be constructed from a first material, such as stainless steel, and a distal region 2706 that can be constructed from a second material, such as nitinol. Either or both of the proximal region 2702 and the distal region 2704 can taper inward in a direction toward the distal end of the guidewire assembly 2700, such as in one or more tapering regions, which can be contiguous or separated by respective non-tapering regions. A distal region 2706 of the guidewire assembly 2700 can include a proximal spring coil region 2504, a distal spring coil region 2506, a connector block 2708 (e.g., containing components of the pressure sensor assembly 2400, such as described herein) therebetween from which a flattened or other core guidewire can extend distally toward and connecting to an atraumatic rounded distal tip 2710.

At least one groove 2712 can be formed on an outward circumferential surface of the guidewire assembly 2700. The groove 2712 can extend from a proximal end or region of the guidewire assembly 2700 toward and to a distal portion of the guidewire assembly 2700 and can terminate at a proximal side of the connector block 2708. The groove 2712 can extend along all or a portion of the length of the guidewire assembly 2700, such as in a spiral helix or otherwise. The pitch of the helix can be fixed or multi-valued (e.g., a looser pitch (e.g., between 30 mm and 50 mm) at a proximal portion of the guidewire assembly 2700 and a tighter pitch (e.g., between 5 mm and 10 mm pitch) at the distal (e.g., over a length of about 30 centimeters) portion of the guidewire assembly 2700). The helical arrangement can help accommodate flexing curvature in the guidewire assembly 2700 as it is introduced along tortuous vascular or other non-linear paths. A tighter pitch can be more accommodating to curvature in the guidewire assembly 2700. The groove 2712 can carry the optical fiber 2402 therein, such as can be secured therein by an adhesive underlayer (e.g., UV-cured adhesive, hot-melt adhesive, epoxy or other two-part adhesive) or overlayer (e.g., such as any suitable overcoating used for an existing guidewire). In an example, the groove 2712 can be about 40 micrometers across and about 40 micrometers deep, and can be constructed so as to only occupy about 1/100 or less of the surface area of the guidewire assembly 2700, thereby leaving the mechanical properties of the guidewire assembly 2700 substantially intact as though the groove 2712 were not present. For retrofitting an existing guidewire, the groove 2712 can be formed by laser-etching or other suitable process. The guidewire can additionally or alternatively formed together with the groove 2712, such as during drawing of the guidewire body during its manufacture, such as by mechanically scoring the guidewire body or otherwise. If a portion of the guidewire body is tapered down (e.g., toward a distal end, such as using centerless or other grinding), then any grooves that were formed during the guidewire drawing, but removed by the grinding, can be replaced by a respective connecting groove that can be formed after grinding, such as by laser-etching the ground portion of the guidewire body.

Figure 28:
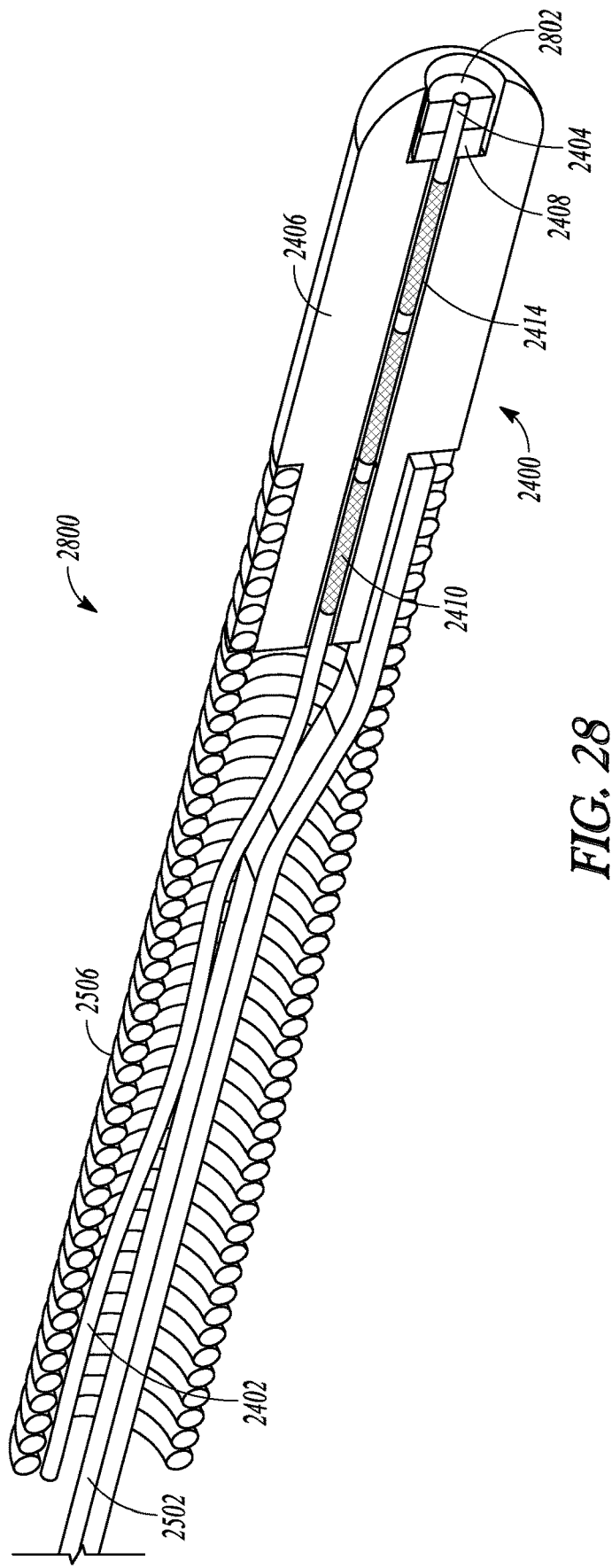
FIG. 28 shows an example in which the pressure sensor assembly (e.g., as explained herein) can be located at a distal end of a guidewire assembly.

FIG. 28 shows an example in which the pressure sensor assembly 2400 (e.g., as explained herein) can be located at a distal end of a guidewire assembly 2800, e.g., more distal than the distal spring coil region 2506, such as within or providing a rounded atraumatic distal tip. A flattened or other distal end of the core guidewire 2502 can connect to a proximal end of the housing 2406 of the pressure sensor assembly 2400. More proximal regions of the guidewire assembly 2800 can include a proximal spring coil region 2504, a connector block (such as a connector block 2508, which can optionally include a second, more proximal pressure sensor as described with respect to FIG. 25), and other elements such as shown in FIG. 25.

The distal end pressure sensor assembly 2400 can include an anchored first sensing region 2410 and a suspended second sensing region 2414, such as explained herein. The gasket 2408 and the distal anchor 2404 can be located within a cylindrical or other recess 2802 that can be exposed to the ambient environment about the distal end of the guidewire assembly 2800. In an example such as shown in FIG. 28, the recess 2802 can be cylindrical and can extend longitudinally along the central axis of the guidewire assembly 2800, such as to face longitudinally outward from the distal end of the guidewire assembly 2800. In an example, the distal end of the optical fiber 2402 can be attached to the anchor 2404, and both the anchor 2404 and the gasket 2408 can be suspended within the recess 2802, such as by tension in the optical fiber 2402 to which the anchor 2404 can be attached with the gasket 2408 captured proximal to the anchor 2404. This can help provide pressure sensing due to longitudinal optical fiber tension variations near the distal end of the guidewire assembly 2800, and can help isolate the effect of lateral pressure variations or torque upon the pressure sensor assembly 2400.

Having a pressure sensor located at a guidewire distal tip can provide advantages in certain applications, such as where information about pressure distal to an occlusion may be desirable. For example, when pushing a guidewire across a chronic total vascular occlusion, it may be difficult to determine whether the distal tip is within a lumen of the blood vessel or within a subintimal layer of the blood vessel. A distal-tip pressure sensor can permit providing distal-tip pressure information that can be useful in determining the nature of such location of the distal tip of the guidewire assembly 2800. In an example in which a distal tip pressure sensor is provided together with a more proximal pressure sensor (e.g., located between the proximal spring coil region 2504 and the distal spring coil region 2506), a pressure differential across an occlusion can be sensed and provided to a user, such as for diagnostic or interventional (e.g., stent-placement) purposes.

Figure 29:
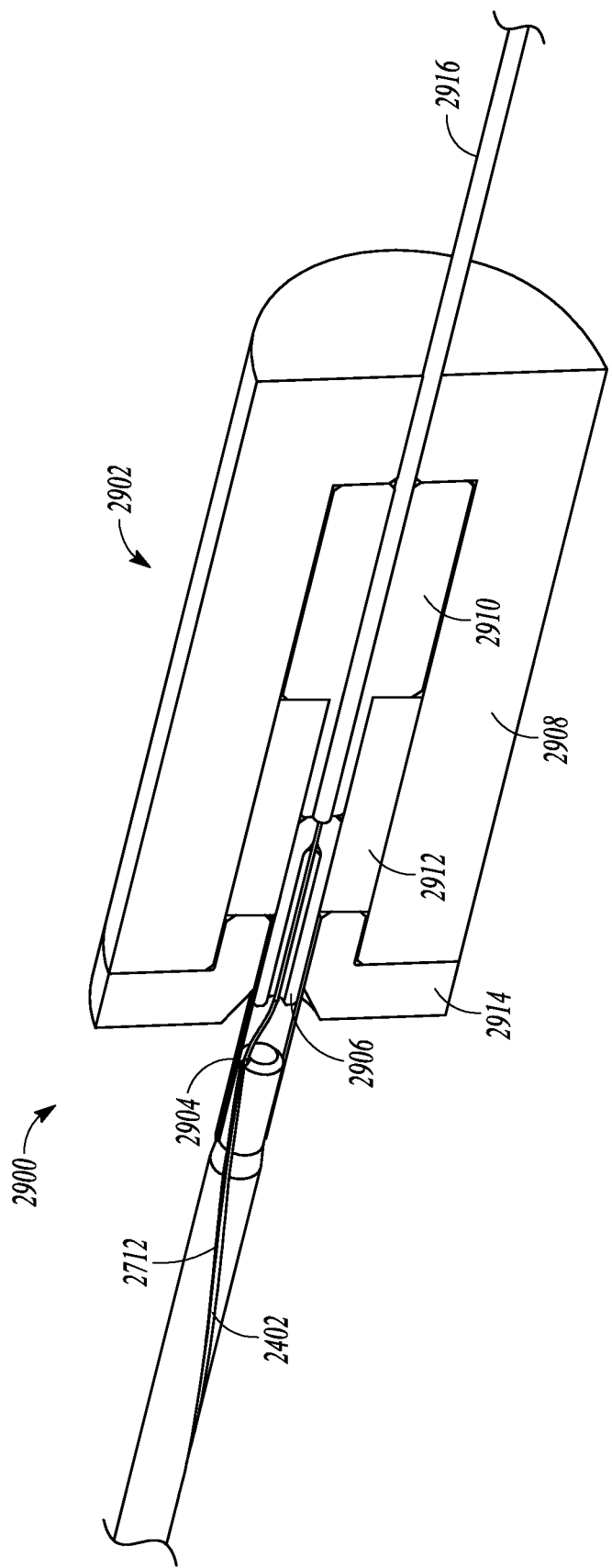
FIG. 29 shows an example of a proximal region of a guidewire assembly, such as one of the various guidewire assemblies described herein, terminating at a proximal end connector.

FIG. 29 shows an example of a proximal region of a guidewire assembly 2900, such as one of the various guidewire assemblies described herein, terminating at a proximal end connector 2902. The guidewire assembly 2900 can include a helically wound optical fiber 2402 that can be located in a helical groove 2712 along the guidewire body. The proximal end connector 2902 can include separable portions: (1) a distal portion that can include a metal or other tube 2904 (also referred to as a tubular coupler) having an interior lumen diameter that can be attached to both the outer diameter of the body of the proximal region of the guidewire assembly 2900 and the outer diameter of a ceramic or other distal ferrule 2906 such that the optical fiber can extend from a periphery of the guidewire body to and through a center axis lumen of the distal ferrule 2906; and (2) a proximal portion that can include a connector housing 2908 carrying a ceramic or other proximal ferrule 2910, a split sleeve ferrule guide 2912, and a distal receptacle guide 2914 that can provide a tapered portion into which a portion of the distal ferrule 2906 and the metal tube 2904 can be received. The optical fiber 2402 can terminate at a flat or dome polished (e.g., ultrapolished physical connector, "UPC") proximal end of the distal ferrule 2906, where it can butt against and optically couple with a flat or dome polished (e.g., UPC) distal end of the proximal ferrule 2910, which can provide a center axis lumen through which an optical fiber 2402 can extend in a proximal direction, such as to an optical, electronic, or optoelectronic signal generation or processing apparatus. While the optical fibers 2402 and 2916 can be the same diameter, in an example, the optical fiber 2402 can be a small diameter optical fiber (e.g., 25 micrometers outer diameter) and the optical fiber 2916 can be a standard sized telecommunications optical fiber (e.g., 125 micrometers outer diameter), such as with the mode field diameter (MFD) of the optical fiber 2402 being less than or equal to the MFD of the optical fiber 2916. When the proximal end of the guidewire terminating in connector portion 2902 is detached, other components can be easily slipped over the guidewire.

Using various techniques described above, changes in ambient pressure can be detected by measuring the wavelength change, e.g., quantified change in phase-shift, by an FBG sensor within a housing, e.g., housing 308 of FIG. 3. As described above with respect to FIGS. 4A-4C and FIG. 6A, the change in phase-shift can be quantified by locking a laser at a position on a slope of the transmission notch of the resonant feature, tracking a particular optical power level in the resonant feature, and adjusting the bias current of the laser which, in turn, subtly changes the wavelength to maintain this "locked" relationship.

These techniques can produce satisfactory results when the optical insertion loss is constant. In some example implementations, however, the overall insertion loss of the pressure sensor and/or system can change during the measurement, e.g., kinking in the optical fiber. As shown and described below with respect to FIG. 30, a change in the optical insertion loss can lead to an artificial shift in the tracking wavelength, and thus an offset error in the pressure reading, if the optical locking level or threshold is not adjusted accordingly.

Figure 30:
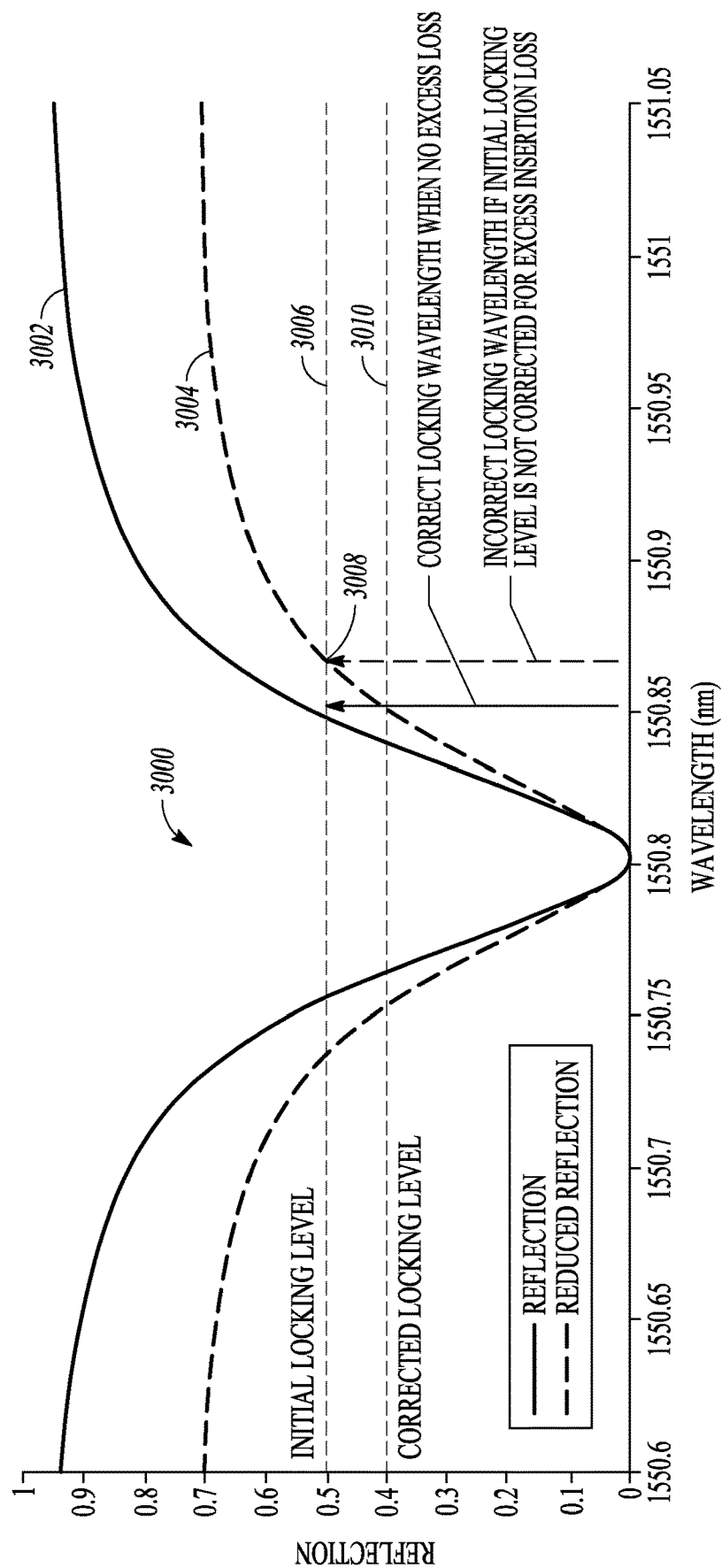
FIG. 30 depicts a conceptual response diagram illustrating the effect of an uncorrected locking level on a locking wavelength.

FIG. 30 depicts a conceptual response diagram illustrating the effect of an uncorrected locking level on a locking wavelength. In FIG. 30, where the x-axis represents wavelength and the y-axis represents the intensity of the reflected light, a transmission notch 3000 is shown within a reflection band 3002, and a reduced reflection band 3004, which is caused by insertion loss. An initial locking level, or optical threshold, 3006 is depicted, which corresponds to a wavelength of about 1550.85 nm and a reflection intensity of 50%.

If insertion loss is introduced, which results in the reduced reflection band 3004, then the locking level may move up or down the slope of the reduced reflection band 3004 in order to maintain its locking level, e.g., 50%, despite the fact that the transmission notch 3004 has not moved. If the insertion loss increases (optical power decreases), then the shift can be to a higher, incorrect locking wavelength because the locking circuit climbs the slope of the reduced reflection band 3004 to maintain the set optical level, as shown at 3008. If the insertion loss decreases (optical power increases)(not depicted in FIG. 30), then the shift can be to a lower, incorrect locking wavelength because the locking circuit moves down the slope of the reduced reflection band 3004 to maintain the set optical power level. Either of these conditions can lead to a significant drift in the apparent pressure level even if there has been no phase-shift change in the FBG filter.

As described in more detail below, using various techniques of this disclosure, the locking level 3006 can be corrected for insertion loss, resulting in a corrected locking level 3010. In accordance with this disclosure, a small dither signal can be added to the wavelength of the laser at, for example, a frequency outside those associated with the pressure sensing. Then, the AC component, which is the change in the optical signal reflected from the pressure sensor back to the optical detector, e.g., optical detector 608 of FIG. 6A, can be extracted from the optical signal via an electronic circuit associated with the optical detector. The magnitude of the AC component can then be used to make any adjustments to the locking level to null out any offset errors.

Figure 31:
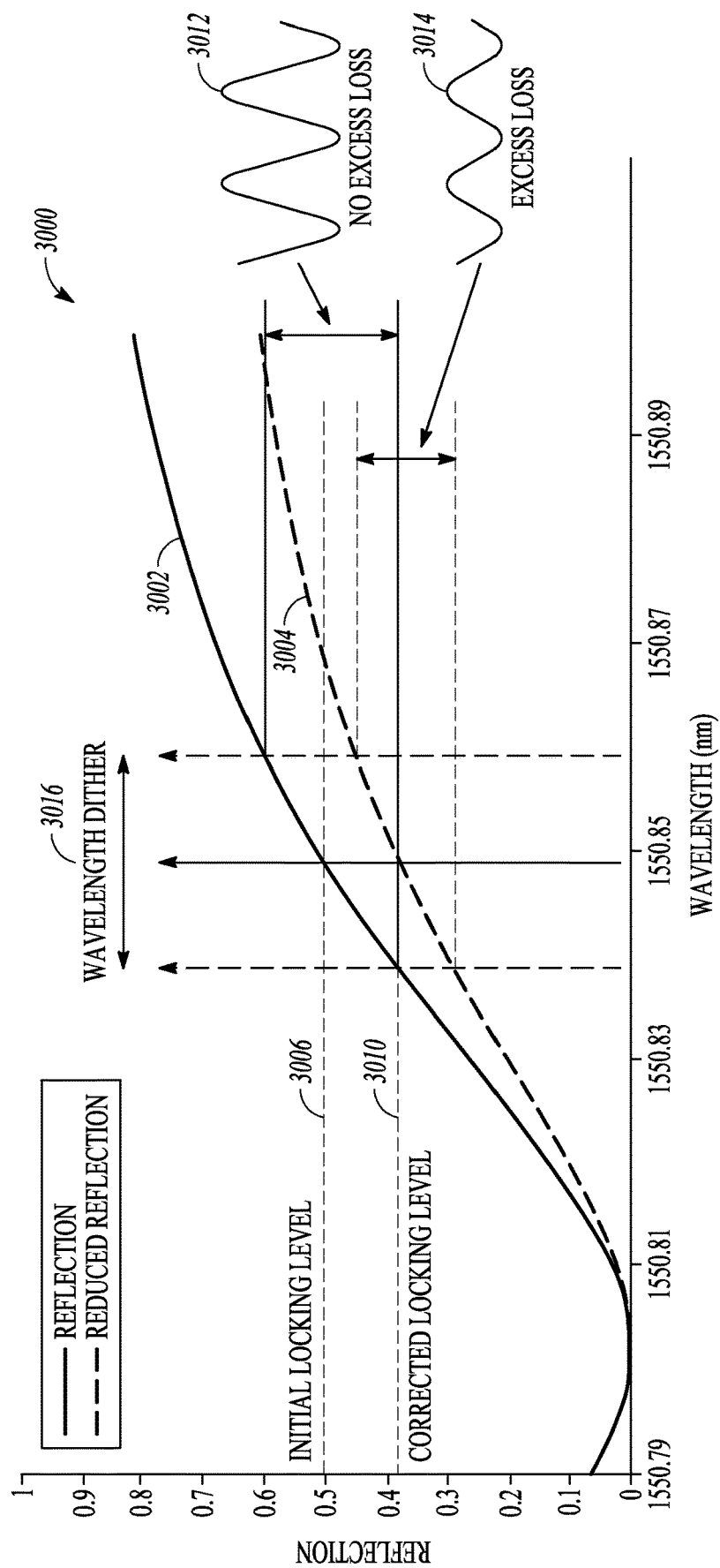
FIG. 31 depicts the conceptual response diagram of FIG. 30 compensated for optical insertion loss in an optical pressure sensor using various techniques of this disclosure.

FIG. 31 depicts the conceptual response diagram of FIG. 30 compensated for optical insertion loss in an optical pressure sensor using various techniques of this disclosure. In FIG. 31, where the x-axis represents wavelength and the y-axis represents the intensity of the reflected light, a transmission notch 3000 is shown within a reflection band 3002, and a reduced reflection band 3004, which is caused by insertion loss.

Two AC components 3012, 3014 are depicted in FIG. 31, where the AC component 3012 depicts a magnitude of the AC component with no excess loss and where the AC component 3014 depicts a magnitude of the AC component with excess loss. Thus, the magnitude of the AC component can change with insertion loss.

As indicated above, a small dither signal 3016 can be added to the wavelength of the laser. Then, an AC component can be extracted from the optical signal via an electronic circuit associated with the optical detector. As can be seen in FIG. 31, the amplitude of the AC components 3012, 3014 can vary in proportion to the overall signal level as long as the amount of wavelength dither is held constant. That is, if the wavelength range of the dither 3016 is held constant, the magnitude of the AC component can scale directly with the optical insertion loss.

By comparing a current value of the AC component, e.g., AC component 3014, to an initial value of the AC component, e.g., AC component 3012, the controller 602 (FIG. 6A) can determine whether the optical insertion loss has increased or decreased. The current value of the AC component can be fed back to the optical locking circuit of FIG. 6A, a portion of which is described below with respect to FIG. 33. Then, because the AC component is reduced in proportion to the change in insertion loss, the controller 602 of FIG. 6A can adjust the optical locking level accordingly to maintain the correct locking wavelength.

In some examples, a frequency and amplitude of the wavelength dither 3016 can be selected so as to be compatible with the pressure measurements. For example, for the dither frequency, a value can be selected that is higher than the necessary bandwidth for pressure sensing. Assuming, for example, that the pressure bandwidth is between 0-25 Hz, then it might be desirable to select a frequency for the wavelength dither at least five times higher than the pressure bandwidth.

Figure 32:
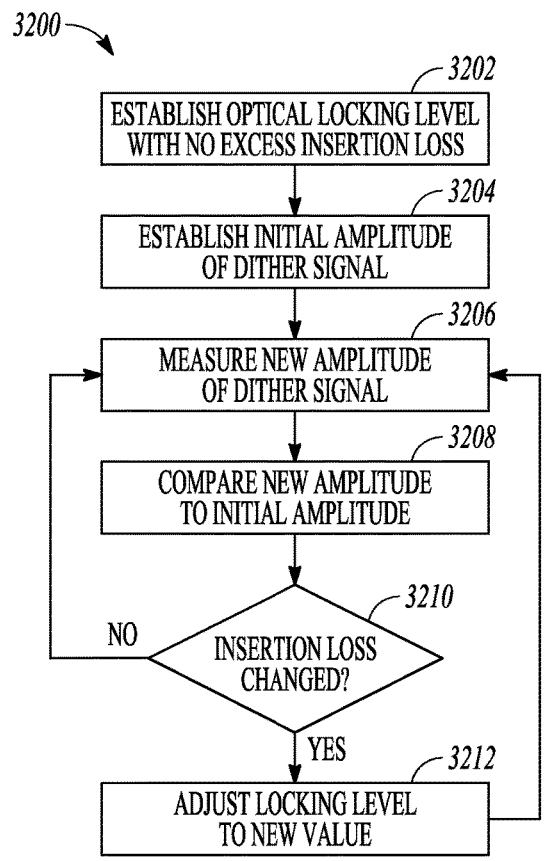
FIG. 32 is a flow diagram illustrating an example of a method for compensating for optical insertion loss in an optical pressure sensor using various techniques of this disclosure.

FIG. 32 is a flow diagram illustrating an example of a method 3200 for compensating for optical insertion loss in an optical pressure sensor using various techniques of this disclosure. The controller 602 of FIG. 6A can establish, or determine, an optical locking level with no excess insertion loss (3202), e.g., initial locking level 3006 of FIG. 31, and establish, or determine, an initial amplitude of a dither signal (3204), e.g., the AC component 3012 of FIG. 31, by extracting the dither signal from the optical signal reflected from the pressure sensor and measuring its amplitude. The controller 602 can measure a new amplitude of the dither signal (3206), e.g., the AC component 3014 and compare the new amplitude to the initial amplitude (3208). If the insertion loss has changed ("YES" branch of 3210), as determined by the comparison at 3208, then the controller 602 can control the laser drive current control 614 of FIG. 6A or the locking set point value 612 of FIG. 6A to adjust the locking level to a new value (3212), e.g., if the AC component decreases then the locking level is reduced by the appropriate amount. If the insertion loss has not changed ("NO" branch of 3210), as determined by the comparison at 3208, then the controller 602 can continue to measure the new amplitude of the dither signal at 3206.

Figure 33:
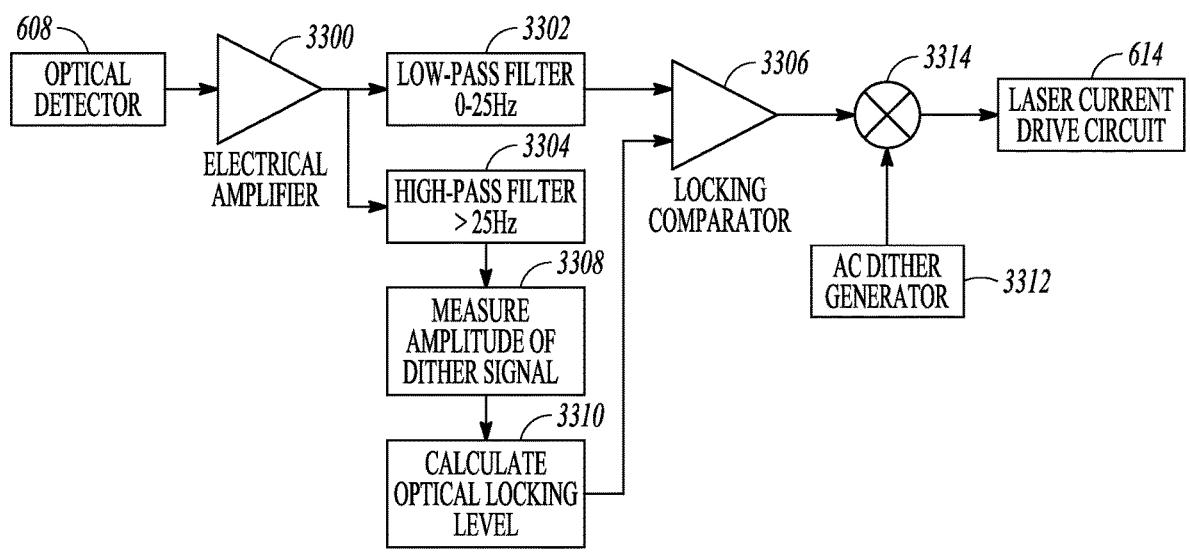
FIG. 33 is a block diagram of an example of a portion of the laser tracking system of FIG. 6A for compensating for optical insertion loss in an optical pressure sensor using various techniques of this disclosure, in accordance with this disclosure.

FIG. 33 is a block diagram of an example of a portion of the laser tracking system of FIG. 6A for compensating for optical insertion loss in an optical pressure sensor using various techniques of this disclosure, in accordance with this disclosure. An AC dither generator 3312 generates a dither signal that is summed together with the laser control current via summer 3314 and passed to the laser current drive circuit 614. The laser current drive circuit 614 generates a drive current for laser 604 of FIG. 6A.

An optical signal reflected back from the pressure sensor, e.g., pressure sensor 300 of FIG. 3, is detected by the optical detector 608, amplified by electrical amplifier 3300, and filtered by a low pass filter 3302, e.g., frequencies of about 0-25 Hz, and a high pass filter 3304, e.g., frequencies greater than 25 Hz. The low pass filter 3302 passes the DC level to a locking comparator 3306 and the high pass filter 3304 passes the high pass filtered signal, or AC component, to the controller 602, which measures the amplitude of the dither signal (3308), or AC component, and calculates the optical locking level (3310), e.g., if the AC component decreases then the locking level is reduced to the appropriate value. The controller 602 passes the calculated optical locking level to the locking comparator 3306, which compares the DC level and the calculated optical locking level. The laser current drive circuit 614 or the locking set point 612 can be adjusted based on the comparison. In this manner, a constant center wavelength is maintained. The same result can also be achieved by accounting for the wavelength shift in the form of a software correction.

In one example implementation, the frequency of the dither 3016 of FIG. 31 can be selected in order to design a low-pass filter 3302 that can reduce the residual AC dither component in the electrical path to the locking circuit controlled by the laser current drive circuit 614. This may be desirable in order to prevent the locking circuit from chasing the locking level at the frequency of the dither. It may be desirable for the locking circuit to see the average or DC level of the optical locking level.

There are many ways to filter the optical signal and only one example is presented in this disclosure. Other filtering techniques or techniques for suppressing the AC component could be employed and are considered within the scope of this disclosure.

In order to ensure that the laser is able to respond to the dither frequency chosen without any reduction in the actual wavelength shift desired, there may be factors to consider in selecting a dither frequency. For example, it has been found that the design of the laser submount has an effect on the frequency at which the laser can dither the laser.

Typical dither frequencies can range from around 100 Hz to 1000 Hz before the response starts to diminish. In one example implementation, it may be desirable to select a dither frequency between about 300 Hz and about 10400 Hz.

The dither magnitude can be selected to have an appropriate scale to give a detectable AC component, e.g., around ±10% of the overall DC signal level. In this example, if the maximum optical power level is assumed to be about 1000 µW and the slope is assumed to be about 50 µW/pm, then it may be desirable to shift the wavelength of the laser by the equivalent of about ±2 pm (±100 µW). If the laser is assumed to have a wavelength coefficient of about 5 pm/mA, then this would equate to a bias current dither of about ±0.4 mA. These numbers are given for purposes of illustration only and could be adjusted within sensible limits.

To summarize, with respect to FIGS. 31-33, this disclosure describes, among other things, the following techniques: compensating for changes in optical insertion loss of the pressure sensor that would otherwise be seen as large drifts in the apparent measured pressure; calculating and adjusting an optical locking level to achieve compensation of changes in optical insertion loss by wavelength dithering of the tracking laser; applying wavelength dither to a tracking laser to generate a signal with amplitude proportional to optical insertion loss; and applying feedback to an optical locking level to compensate optical insertion loss.

It should be noted that the dither techniques described above can be used in a similar manner to track the insertion loss of an intravascular ultrasound (IVUS) imaging device and to make adjustments to the optical locking levels. It may also be desirable to make dynamic adjustments to a sensitivity correction matrix for the imaging elements in a receive mode. The quality of imaging can be improved when the sensitivity of the elements are balanced in the reconstruction matrix to reduce side-lobe levels.

A first order calibration of the receive sensitivity of the elements can be made by measuring the AC component from the wavelength dither as this indicates the slope of the sensing element. The expected receive ultrasound signal is proportional to the ultrasound energy imparted on the element (this is converted to a change in the optical cavity length or phase-shift) multiplied by the slope of the cavity. Therefore, by knowing the slope from the dither, an expected signal sensitivity from the element can be calculated.

In the case of IVUS, the relationship of the frequencies is reversed, where the dither frequency is well below the ultrasound frequencies and is filtered out by the ultrasound electrical circuits.

To summarize, with respect to IVUS imaging devices, this disclosure describes, among other things, the following techniques: dynamically adjusting optical locking levels; dynamically adjusting an element calibration matrix to improve image reconstruction; and calibrating receive sensitivity of elements based on dither slope measurements. Many of the techniques described in this disclosure are applicable to intravascular imaging devices, such as those described in Bates & Vardi U.S. Pat. Nos. 7,245,789, 7,447,388, 7,660,492, 8,059,923, U.S. Pat. Pub. No. US-2012-0108943-A1, and U.S. Provisional Patent Application No. 61/783,716, titled "Optical Fiber Ribbon Imaging Guidewire and Methods" to Tasker et al. and filed on Mar. 14, 2013, each of which is hereby incorporated by reference herein in its entirety.

Turning to another aspect, in any optical system with highly coherent light sources, e.g., a narrow linewidth laser, there is a possibility that any unintended reflections, even very weak ones, can form a resonant optical cavity within the device. The cavity can exhibit a strong frequency component that depends on the optical path length of the cavity (in this case the length of optical fiber between reflection points). The frequency of the cavity is given by:

$$\Delta v = \frac{c}{2L}$$

where $\Delta v$=frequency separation of maxima (Hz), C=speed of light, and L=optical path length (Length×refractive index). The longer the cavity, the more closely spaced the ripples in the frequency and wavelength domains.

A large amount of optical energy can be circulated within the pressure sensing device and, under certain conditions, can form undesirable optical resonances with other elements of the system. The undesirable resonances can be formed between any two points of optical reflection. For instance, the undesirable resonances can be formed between the FBGs and a system connector, or the FBGs and a pressure wire connector. In accordance with this disclosure and as described in more detail below with respect to FIGS. 34-37, these undesirable resonances can be averaged out using dither techniques, thereby reducing their overall effect on the pressure measurements.

Figure 34:
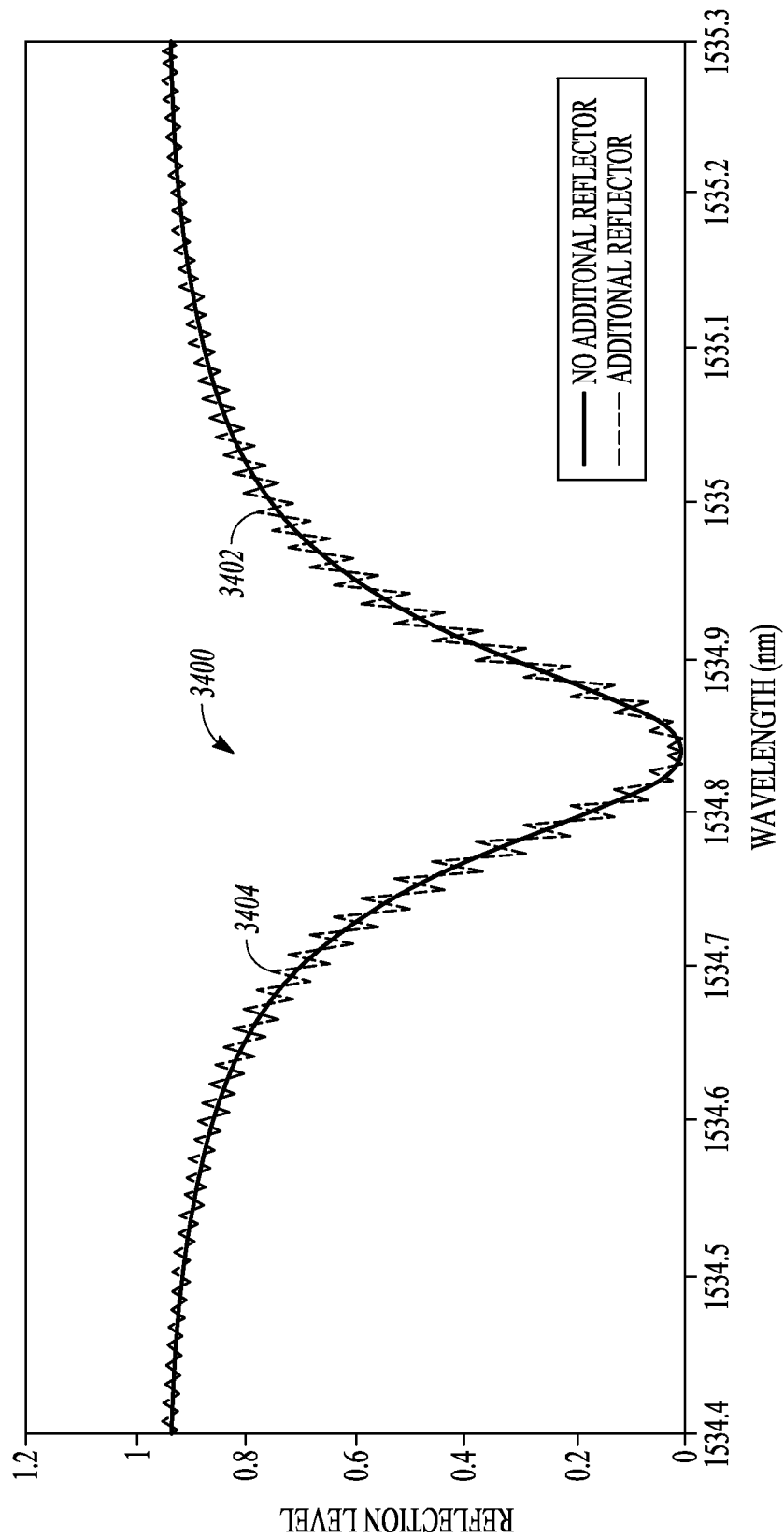
FIG. 34 depicts a conceptual response diagram illustrating undesirable optical resonances caused by additional reflection in an optical system.

FIG. 34 depicts a conceptual response diagram illustrating undesirable optical resonances caused by additional reflection in an optical system. In FIG. 34, where the x-axis represents wavelength and the y-axis represents the intensity of the reflected light, a transmission notch 3400 is shown within a reflection band 3402. The undesirable optical resonances are shown as ripples 3404 overlaid on the fundamental response. In this example the undesirable reflection point is at a distance of about 70 mm from the FBGs.

In an example of a pressure sensing device, there may be an optical connector to the system about two meters from the FBG filters that is a possible source of reflections. The calculated expected wavelength of the ripple caused by a reflection at two meters is approximately 0.4 pm (at 1550 nm). There is a possibility that the locking system can become confused by these ripples 3404 and hop between them, which appears as a sudden jump in the apparent pressure reading, e.g., 10 mm/Hg, shown and described below with respect to FIG. 35. In the context of pressure sensing, such a jump is unwanted and likely unacceptable due to the need for accurate pressure measurements.

Figure 35:
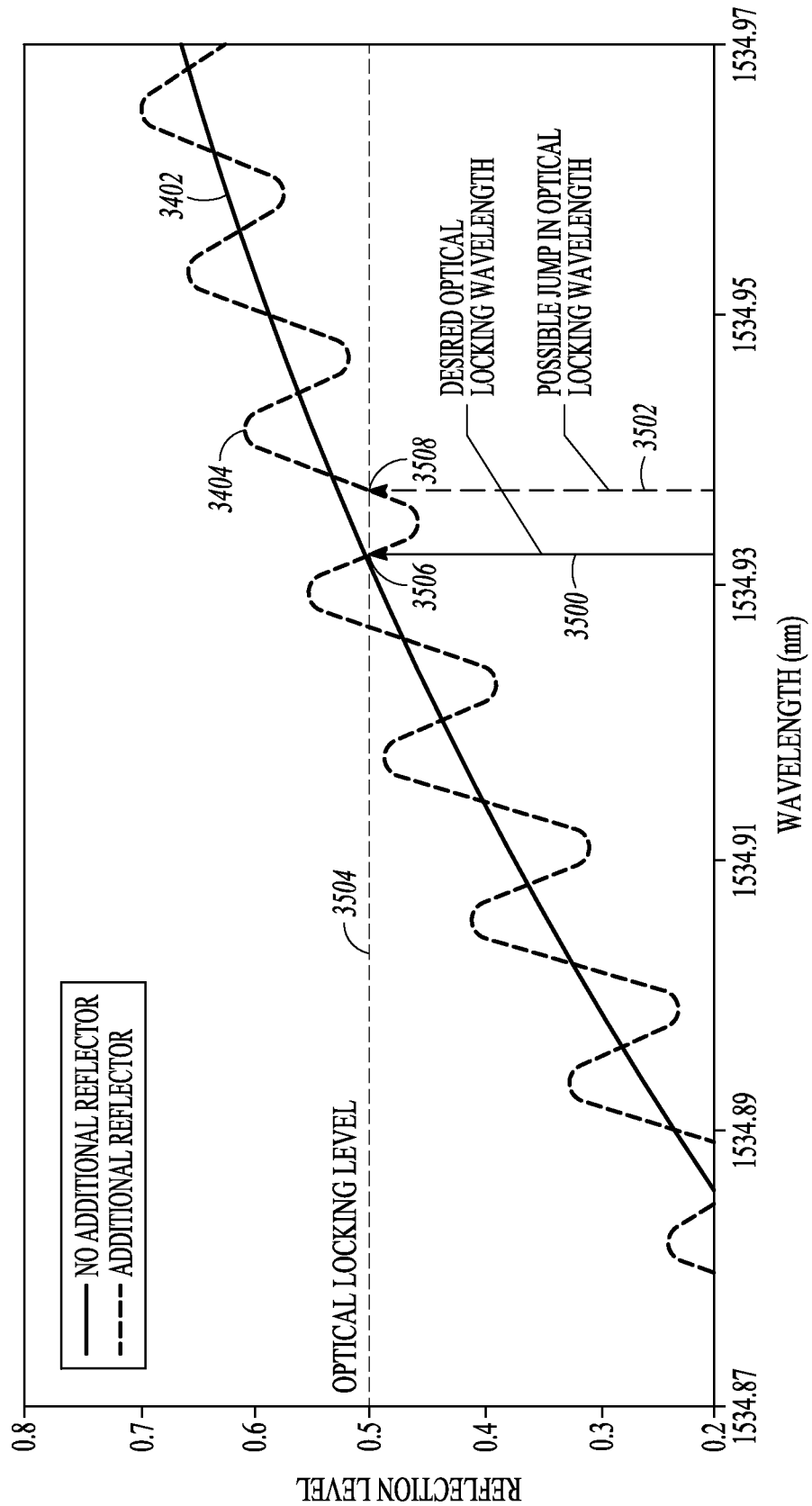
FIG. 35 depicts the conceptual response diagram of FIG. 34 further illustrating undesirable locking circuit wavelength hopping.

FIG. 35 depicts the conceptual response diagram of FIG. 34 further illustrating undesirable locking circuit wavelength hopping. FIG. 35 shows a calculated response for a weak reflection at 70 mm (a non-limiting example for purposes of illustration only) and how the locking circuit can become confused and shift to a different wavelength. More particularly, the locking circuit can become confused because the optical locking level 3504 can intersect both the fundamental response 3402 (at point 3506) and a ripple 3404 (at point 3508), resulting in two possible optical locking wavelengths. As a result of the ripple 3404, the desired optical locking wavelength at 3500 can jump to a higher optical locking wavelength 3502. Assuming that the sensor has a pressure-to-wavelength coefficient of around fpm for 25 mm/Hg and that the 2 m cavity has a ripple period of 0.4 pm, then the apparent shift is approximately 10 mm/Hg, which is highly undesirable.

In accordance with this disclosure and as described in more detail below with respect to FIG. 36, the optical dither techniques described above can be used to average through these ripples 3404 and to reduce or eliminate their effects on determining an optical locking wavelength.

Figure 36:
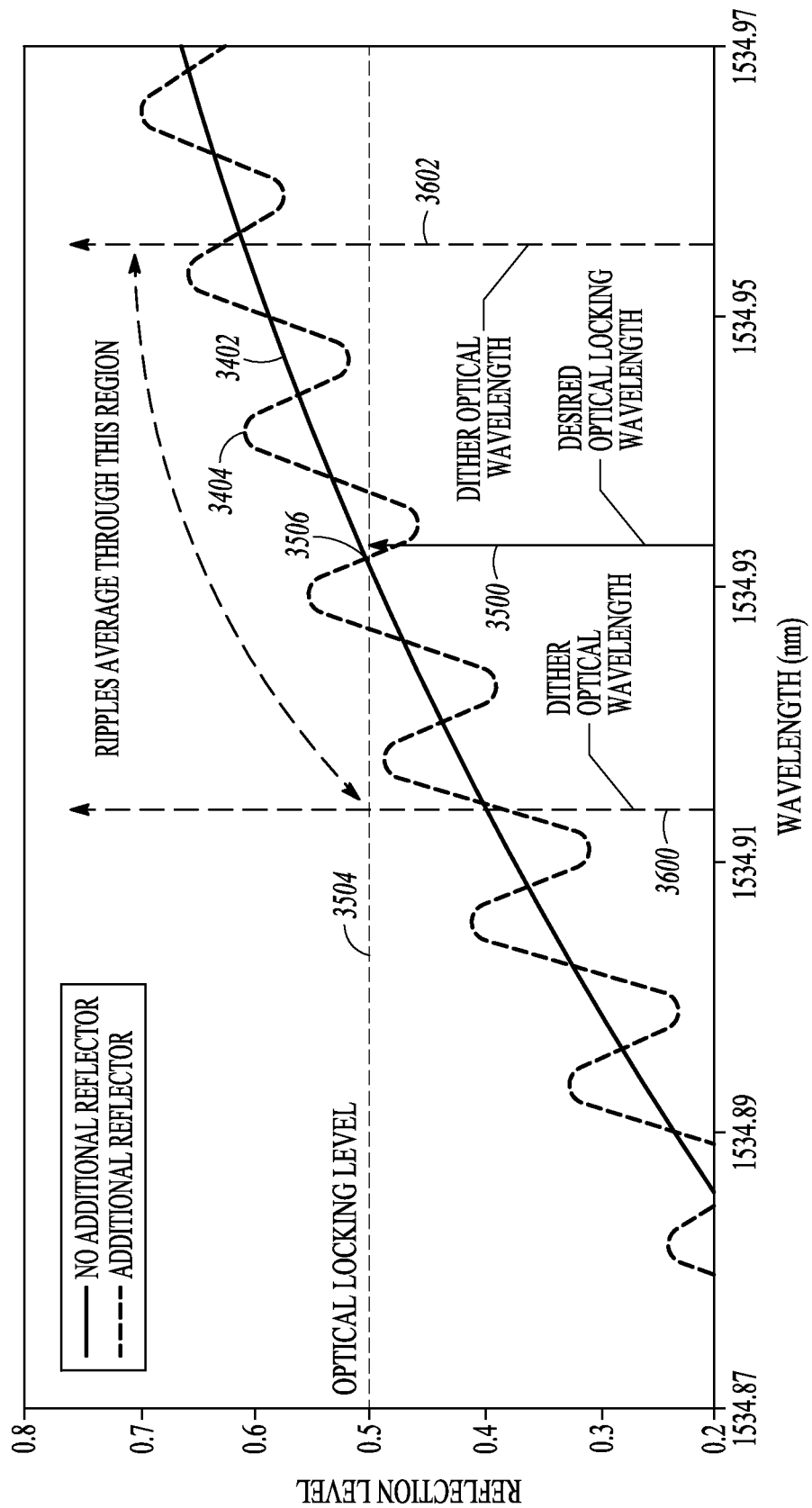
FIG. 36 depicts the conceptual response diagram of FIG. 35 compensated for optical cavity noise using various techniques of this disclosure.

FIG. 36 depicts the conceptual response diagram of FIG. 35 compensated for optical cavity noise using various techniques of this disclosure. In accordance with this disclosure, optical wavelength dither (described above) can be used to sweep or average through a number of the ripple periods. Examples of lower and upper bounds of the dither optical wavelength are depicted at 3600, 3602, respectively. In the example shown in FIG. 36, within the lower and upper wavelength bounds 3600, 3602 are four ripples 3404 that can be averaged. Less or more ripples can be averaged.

When the laser wavelength is dithered, e.g., at a frequency at least five times the bandwidth of the pressure signal, the high frequency AC component can be extracted from the optical signal by filtering, similar to what was described above with respect to the insertion loss compensation techniques and as depicted in FIG. 33. If the pressure signal has a bandwidth of about 0-25 Hz, then the dither frequency is at least 125 Hz, for example. In other examples, the dither frequency is about 300-400 Hz.

Once the high frequency AC component is extracted, then the controller 602 of FIG. 6 can average the AC component over the region of interest, e.g., over four ripples 3404 as in FIG. 36. The dithering occurs at a faster rate than the rate at which the ripples 3404 move side to side during the measurement. As a result, the controller 602 can average through the ripples 3404, thereby removing the optical cavity noise. The controller 602 can then determine an optical locking level and wavelength without becoming confused and jumping to an incorrect optical locking wavelength.

The amplitude and frequency requirements of the dither wavelength can be made to complement the insertion loss compensation (described above), e.g., a frequency of about 300-400 Hz. The amplitude of the wavelength dither can be calculated based on the wavelength separation of the undesirable ripples. In one example, it may be desirable to dither by a wavelength amount that would encompass a sufficient number of ripples to give satisfactory averaging. If the ripples are more closely spaced, then the controller 602 can control generation of a relatively smaller amount of dither than if the ripples were more widely spaced to achieve the same amount of averaging. Take, for example, a two meter long distance between the reflection points, the calculated wavelength of the ripple caused by a reflection at two meters is approximately 0.4 pm (at 1550 nm), then it may be desirable to dither the wavelength of the laser by 5 ripple periods to give satisfactory averaging. The wavelength of the laser can be dithered by a total of 2 pm (0.4 pm×5 ripples). This corresponds to a dither in the laser current of around 0.4 mA, where a typical laser is 5 pm/mA.

In one example implementation, the same dither frequency and electrical filtering used for the insertion loss compensation techniques described above can be used to compensate for the optical cavity noise to allow the usual detection of the pressure readings in the 0-25 Hz bandwidth. In some example implementations, the low frequencies, e.g., 0-25 Hz, that correspond to the pressure signals can be used to control the locking circuit in order to reduce the confusion presented by individual ripples. In one example, the electrical filter circuits can be used to present the average optical detector value to the locking circuits, thus reducing the discrete step nature of the individual ripples.

Figure 37:
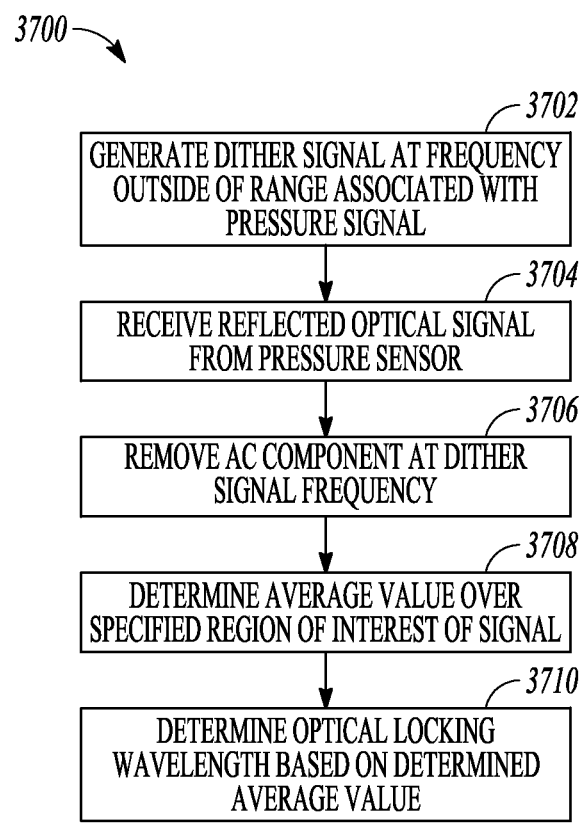
FIG. 37 depicts a flow diagram illustrating an example of a method for compensating for optical cavity noise in an optical pressure sensor using various techniques of this disclosure.

FIG. 37 depicts a flow diagram illustrating an example of a method 3700 for compensating for optical cavity noise in an optical pressure sensor using various techniques of this disclosure. In FIG. 37, the controller 602 of FIG. 6 can control the laser 604 to generate a dither signal at a frequency outside of the range associated with a pressure signal (3702). For example, for a pressure signal having a bandwidth of about 0-25 Hz, the dither frequency can be at least 125 Hz. In one specific example, the dither frequency can be about 300-400 Hz. Next, the optical detector 608 of FIG. 6A can receive the reflected optical signal from the pressure sensor (3704). A low pass filter, e.g., filter 3302 of FIG. 33, can remove or suppress the AC component at the dither signal frequency (3706). Then, the controller 602 can determine a low frequency value, e.g., the average locking level in the low frequency band (0-25 Hz), over the specified region of interest of the signal, e.g., over four ripples (3708). Finally, the controller 602 can determine a noise compensated optical locking wavelength based on the determined average low frequency value (3710).

Figure 38:
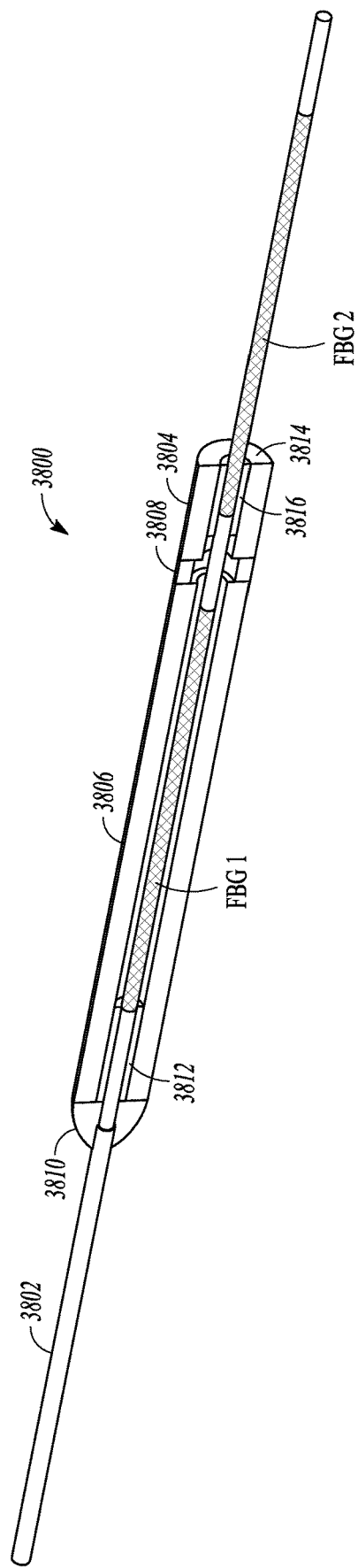
FIG. 38 depicts another example of a portion of a pressure sensor assembly.

FIG. 38 depicts another example of a portion of a pressure sensor assembly 3800. The pressure sensor assembly 3800 is similar in some respects to the concentric pressure sensor assembly 2400 depicted in FIG. 24. The pressure sensor assembly 3800 can include or be coupled to an optical fiber 3802, such as a reduced-diameter longitudinally extending central optical fiber 3802. The pressure sensor assembly 3800 can be located at or near a distal region of the optical fiber 3802.

The pressure sensor assembly 3800 can include a housing that includes a proximal housing portion 3806 and a distal housing portion 3804 separated by a window portion 3808. As described above with respect to FIG. 24, the proximal portion 3806 and the distal portion 3804 can be made from a hard, solid, or inelastic (e.g., fused silica) tubular or other housing. The window portion 3808 can be a soft, flexible, elastic, or compliant gasket located between the distal and proximal portions 3804, 3806.

The optical fiber 3802 enters a proximal end 3810 of the proximal housing portion 3806 and can be securely captured, anchored, or affixed to the proximal housing portion 3806 via a tubular or other attachment (e.g., hardened epoxy or other adhesive) region 3812. Similarly, the optical fiber exits a distal end 3814 of the distal housing portion 3804 and can be securely captured, anchored, or affixed to the distal housing portion 3804 via a tubular or other attachment (e.g., hardened epoxy or other adhesive) region 3816.

The pressure sensor assembly 3800 of FIG. 38 can further include a sensing region that can include two FBGs, namely FBG 1 and FBG 2. As seen in FIG. 38, and in contrast to the concentric pressure sensor assembly 2400 of FIG. 24, an FBG, namely FBG 2, can extend distally beyond the distal end of the pressure sensor assembly 3800. By extending beyond the distal end of the pressure sensor assembly, the FBG 2 can be in direct contact with a bodily fluid, for example. In such an example configuration, any effect that securing materials, e.g., epoxies, may have on the FBG 2 can be eliminated. In addition, by extending the FBG 2 beyond the distal end of the pressure sensor assembly 3800 instead of containing the FBG 2 within the housing, the length of the housing of the pressure sensor assembly 3800 can be reduced. In some example configurations, FBG 1 can be used to measure both pressure and temperature while FBG 2 can be configured to measure ambient temperature, e.g., of the bodily fluid, thereby providing an example of a temperature compensated pressure sensor. In one example configuration, it may be desirable to include a non-reflective termination as close to the distal end of the FBG 2 as possible. Without such a termination, a reflection can modulate the optical signal returning from the pressure sensor, which can affect the accuracy of the measurements.

Figure 39:
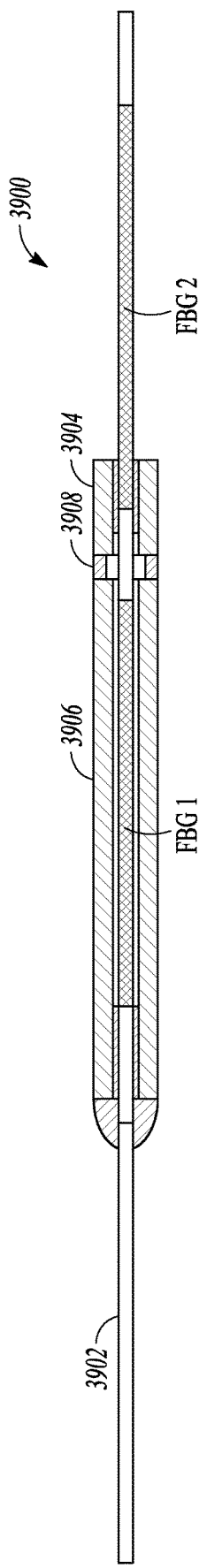
FIGS. 39-41 depict examples of portions of various pressure sensor assemblies.
Figure 40:
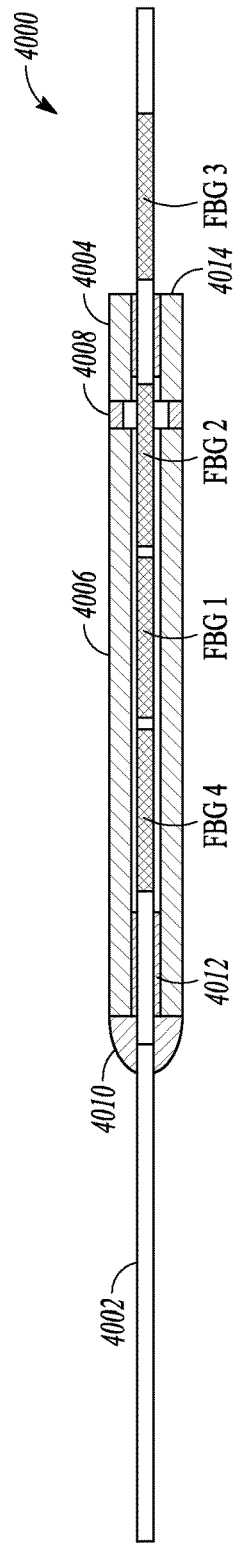
Figure 41:
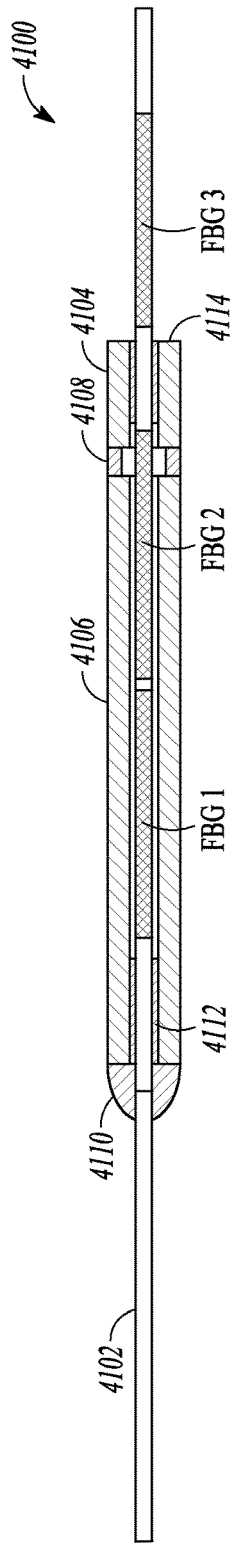

FIGS. 39-41 depict examples of portions of various pressure sensor assemblies. Each of the various pressure sensor assemblies depicted in FIGS. 39-41 include an FBG that extends distally beyond the distal end of each respective pressure sensor assemblies.

The example of a pressure sensor assembly depicted in FIG. 39 is similar to the pressure sensor assembly 3800 described above with respect to FIG. 38 and, as such, will not be described in detail again for purposes of conciseness. In some example configurations, each of FBG 1 and FBG 2 can include a phase shift, e.g., 180 degrees, in the center of the FBG. The phase shift can create a notch in the response, which can be tracked using a tracking circuit as described above.

FIG. 40 depicts an example of a pressure sensor assembly 4000 that can include four FBGs, namely FBGs 1-4. The pressure sensor assembly 4000 can include or be coupled to an optical fiber 4002, such as a reduced-diameter longitudinally extending central optical fiber 4002. The pressure sensor assembly 4000 can be located at or near a distal region of the optical fiber 4002.

The pressure sensor assembly 4000 can include a housing that includes a distal housing portion 4004 and a proximal housing portion 4006 separated by a window portion 4008. As described above with respect to FIG. 24, the distal portion 4004 and the proximal portion 4006 can be made from a hard, solid, or inelastic (e.g., fused silica) tubular or other housing. The window portion 4008 can be a soft, flexible, elastic, or compliant gasket located between the distal and proximal housing portions 4004, 4006.

The optical fiber 4002 enters a proximal end 4010 of the proximal housing portion 4006 and can be securely captured, anchored, or affixed to the proximal housing portion 4006 via a tubular or other attachment (e.g., hardened epoxy or other adhesive) region 4012. Similarly, the optical fiber 4002 exits a distal end 4014 of the distal housing portion 4004 and can be securely captured, anchored, or affixed to the distal housing portion 4004 via a tubular or other attachment (e.g., hardened epoxy or other adhesive) region 4016.

The pressure sensor assembly 4000 of FIG. 40 further includes a sensing region that can include four FBGs, namely FBGs 1-4. As seen in FIG. 40, an FBG, namely FBG 3, extends distally beyond the distal end of the pressure sensor assembly 4000. By extending beyond the distal end of the pressure sensor assembly, the FBG 3 can be in direct contact with a bodily fluid, for example. In such an example configuration, any effect that securing materials, e.g., epoxies, may have on the FBG 3 can be eliminated. In addition, by extending the FBG 3 beyond the distal end of the pressure sensor assembly 4000 instead of containing the FBG 3 within the housing, the length of the housing of the pressure sensor assembly 4000 can be reduced.

In some example configurations, from left to right, FBG 4 can be used to measure pressure, FBG 1 can be used to measure temperature, FBG 2 can be used to measure pressure, and FBG 3 can be configured to measure ambient temperature, e.g., of the bodily fluid, thereby providing an example of a temperature compensated FBG interferometer in optical communication with the optical fiber 4002. Increasing the distance between the two temperature gratings, namely FBG 1 and FBG 3, increases the finesse, which can increase the sensitivity of the sensor, e.g., a steeper slope in the reflection band, and improve the quality factor.

FIG. 41 depicts an example of a pressure sensor assembly 4100 that can include three FBGs, namely FBGs 1-3. The pressure sensor assembly 4100 can include or be coupled to an optical fiber 4102, such as a reduced-diameter longitudinally extending central optical fiber 4102. The pressure sensor assembly 4000 can be located at or near a distal region of the optical fiber 4102.

The pressure sensor assembly 4100 can include a housing that includes a distal housing portion 4104 and a proximal housing portion 4106 separated by a window portion 4108. As described above with respect to FIG. 24, the distal housing portion 4104 and the proximal housing portion 4106 can be made from a hard, solid, or inelastic (e.g., fused silica) tubular or other housing. The window portion 4108 can be a soft, flexible, elastic, or compliant gasket located between the distal and proximal housing portions 4104, 4106.

The optical fiber 4102 enters a proximal end 4110 of the second housing portion 4106 and can be securely captured, anchored, or affixed to the second housing portion 4106 via a tubular or other attachment (e.g., hardened epoxy or other adhesive) region 4112. Similarly, the optical fiber exits a distal end 4114 of the first housing portion 4104 and can be securely captured, anchored, or affixed to the first housing portion 4104 via a tubular or other attachment (e.g., hardened epoxy or other adhesive) region 4116.

The pressure sensor assembly 4100 of FIG. 41 further includes a sensing region that can include three FBGs, namely FBGs 1-3. As seen in FIG. 41, an FBG, namely FBG 3, extends distally beyond the distal end of the pressure sensor assembly 4100. By extending beyond the distal end of the pressure sensor assembly, the FBG 3 can be in direct contact with a bodily fluid, for example. In such an example configuration, any effect that materials, e.g., epoxies, may have on the FBG 3 can be eliminated. In addition, by extending the FBG 3 beyond the distal end of the pressure sensor assembly 4100 instead of containing the FBG 3 within the housing, the length of the housing of the pressure sensor assembly 4100 can be reduced.

In some example configurations, one of the three FBGs can have a response that is larger than the response of the other two FBGs. For example, one of the FBGs, e.g., FBG 2, can have a response with about twice the bandwidth as either FBG 1 or FBG 3. FBG 1 and FBG 3 can each have a narrowband response that resonates with a different portion of the grating of FBG 2.

In one example, FBG 1 can be used to measure pressure, e.g., narrowband response, FBG 3 can be used to measure temperature, e.g., narrowband response, and FBG 2 can be used to measure pressure, e.g., broadband response. As described above, in order to generate a pressure signal that is ambient temperature compensated, the signal generated by FBG 3 can be used as a reference to null a shift in temperature. A controller circuit can be configured to control subtraction of the temperature reference signal (from FBG 3) from the pressure signals (from FBGs 1 and 2), such as to generate a temperature compensated pressure signal. An example of a temperature compensation technique was described above with respect to FIG. 5.

Figure 42:
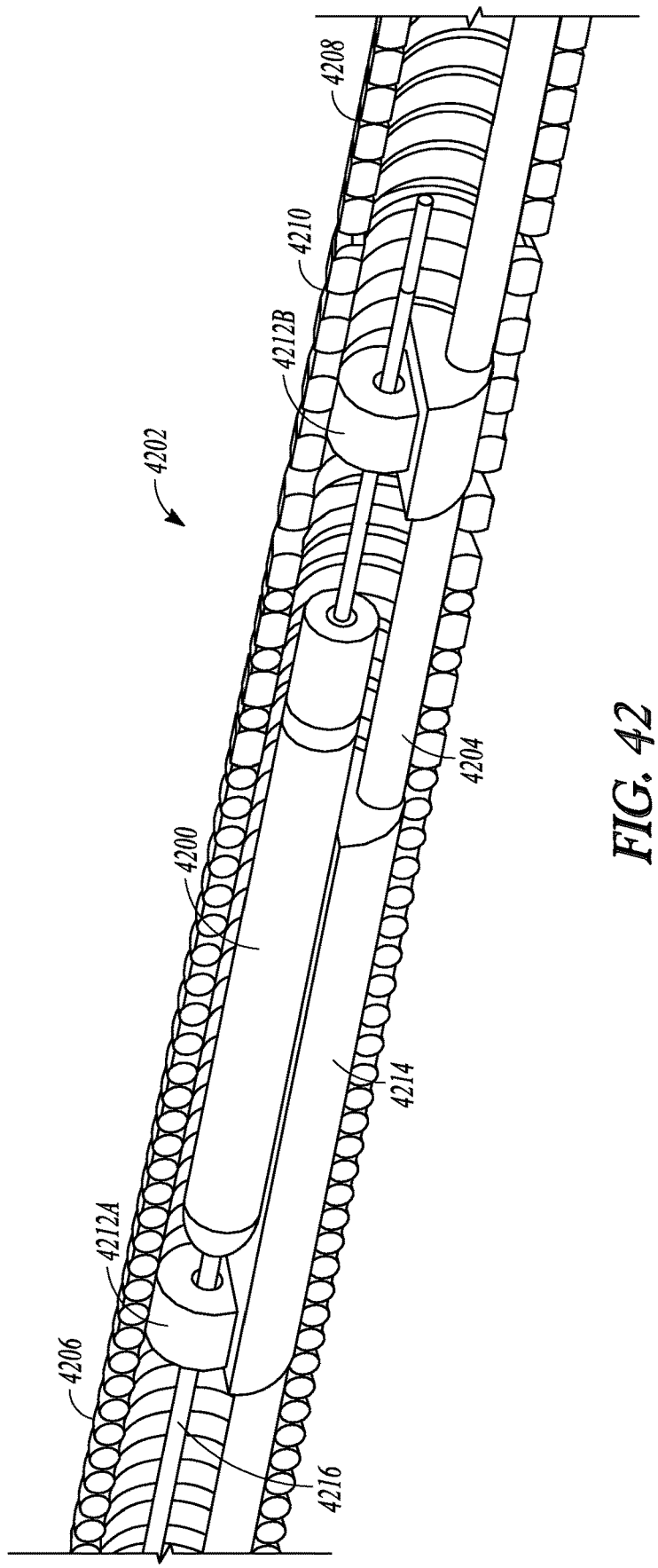
FIG. 42 depicts another example of a guidewire in combination with an optical fiber pressure sensor.

FIG. 42 depicts another example of a guidewire in combination with an optical fiber pressure sensor assembly. In FIG. 42, an optical pressure sensor assembly 4200, e.g., assemblies 3900, 4000, and 4100 of FIGS. 39-41, can be delivered to a desired site using a guidewire, shown generally at 4202. The guidewire 4202 can include a core wire 4204, a proximal coil 4206, and a distal coil 4208. The proximal coil 4206 and the distal coil 4208 can be joined together via a mechanical joint 4210, e.g., solder or adhesive.

The optical pressure sensor assembly 4200 can be mounted to the core wire 4204 via a mounting unit 4214. In turn, the mounting unit 4214 can then be attached to a coil, e.g., proximal coil 4206.

The guidewire 4202 can further include one or more disk spacers 4212A, 4212B (referred to collectively in this disclosure as disk spacers 4212). The disk spacers 4212 can define a hole through which the optical fiber 4216 can extend. The disk spacers 4212 can be included to prevent the optical fiber 4216 from contacting other components of the guidewire 4202, e.g., coils 4206, 4208.

Figure 43C:
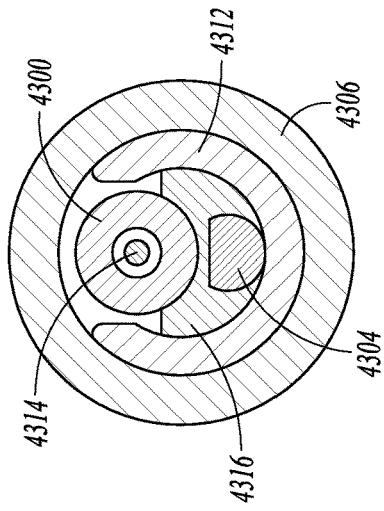
FIG. 43A-43C depict another example of a guidewire in combination with an optical fiber pressure sensor.
Figure 43A:
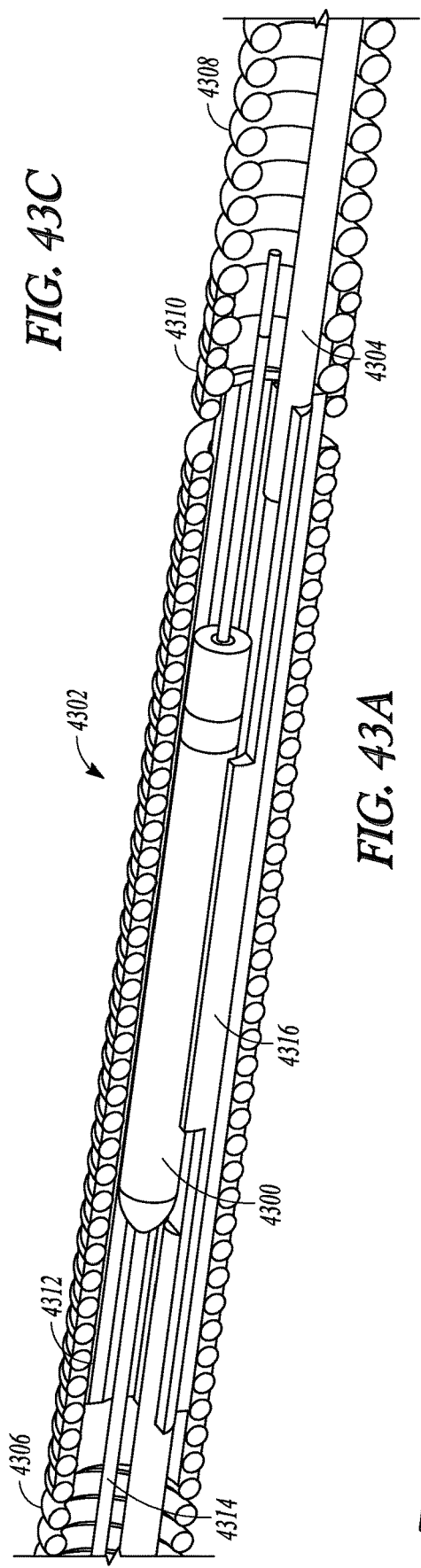
Figure 43B:

FIGS. 43A-43C depict another example of a guidewire in combination with an optical fiber pressure sensor. In FIG. 43A, an optical pressure sensor assembly 4300, e.g., assemblies 3900, 4000, and 4100 of FIGS. 39-41, can be delivered to a desired site using a guidewire, shown generally at 4302. The guidewire 4302 can include a core wire 4304, a proximal coil 4306, and a distal coil 4308. The proximal coil 4306 and the distal coil 4308 can be joined together via a mechanical joint 4310, e.g., solder or adhesive.

The guidewire 4302 can further include a cradle 4312 to provide stiffness around the sensor assembly 4300. The cradle 4312, e.g., U-shaped, is shown in more detail in FIG. 43B. As seen in FIG. 43A, the optical pressure sensor assembly 4300 can fit within the cradle 4312. The optical fiber 4314 can extend into and out of the cradle 4312, and the cradle 4312 can fit inside the coils 4306, 4308. The pressure sensor assembly 4300 can be mounted to the core wire 4304 via a mounting material 4316, e.g., an epoxy, which can extend through the cradle 4312.

FIG. 43C depicts a cross-sectional view of the guidewire assembly shown in FIG. 43A. As seen in FIG. 43C, a portion of the diameter of the core wire 4304 can be reduced over a length of the cradle 4312 to provide sufficient room for mounting the pressure sensor assembly 4300.

FIGS. 44A-44C depict another example of a guidewire in combination with an optical fiber pressure sensor. In FIG. 44A, an optical pressure sensor assembly 4400, e.g., assemblies 3900, 4000, and 4100 of FIGS. 39-41, can be delivered to a desired site using a guidewire, shown generally at 4402. The guidewire 4402 can include a core wire 4404, a proximal coil 4406, and a distal coil 4408.

The guidewire 4402 can further include a tube assembly 4412 to provide stiffness around the sensor assembly 4400. The tube assembly 4412 is shown in more detail in FIG. 44B. The tube assembly includes a proximal end portion 4414 and a distal end portion 4416 that extend from the proximal and distal ends 4418, 4420, respectively, of a main body 4422 of the tube assembly 4412. A portion of the circumference of the main body 4422 of the main body 4422 can be removed to allow pressure signals to reach the pressure sensor assembly 4400.

As seen in FIG. 44A, the optical pressure sensor assembly 4400 can fit within the tube assembly 4412. The optical fiber 4424 can extend into and out of the tube assembly 4412. In contrast to the guidewire design in FIGS. 43A-43C, the tube assembly 4412 does not fit within the coils 4406, 4408. Instead, the coils 4406, 4408 can be affixed, respectively, to the proximal end portion 4414 and the distal end portion 4416 that extend from the proximal and distal ends 4418, 4420 respectively, of the tube assembly 4412. The pressure sensor assembly 4400 can be mounted to the core wire 4404 via a mounting material 4426, e.g., an epoxy, which can extend through the tube assembly 4412.

FIG. 44C depicts a cross-sectional view of the guidewire assembly shown in FIG. 44A. As seen in FIG. 44C, a portion of the diameter of the core wire 4404 can be reduced over a length of the tube assembly 4412 to provide sufficient room for mounting the pressure sensor assembly 4400.

FIGS. 45A-45B depict an example of a core wire, shown generally at 4500, that can be used in combination with an optical fiber pressure sensor. During manufacture, the diameter of the core wire 4500 can be varied over specified lengths in order to form a desired shape. For example, as seen in FIG. 45A, the core wire 4500 can be manufactured to include a portion 4502 with a diameter that is larger than the remaining proximal or distal portions 4504, 4506, respectively, of the core wire 4500. The core wire 4500 can be manufactured to include one or more tapered portions 4508A-4508C that taper the portion 4502 from its larger diameter to the smaller diameter of the proximal and distal portions 4504, 4506.

Figure 46:
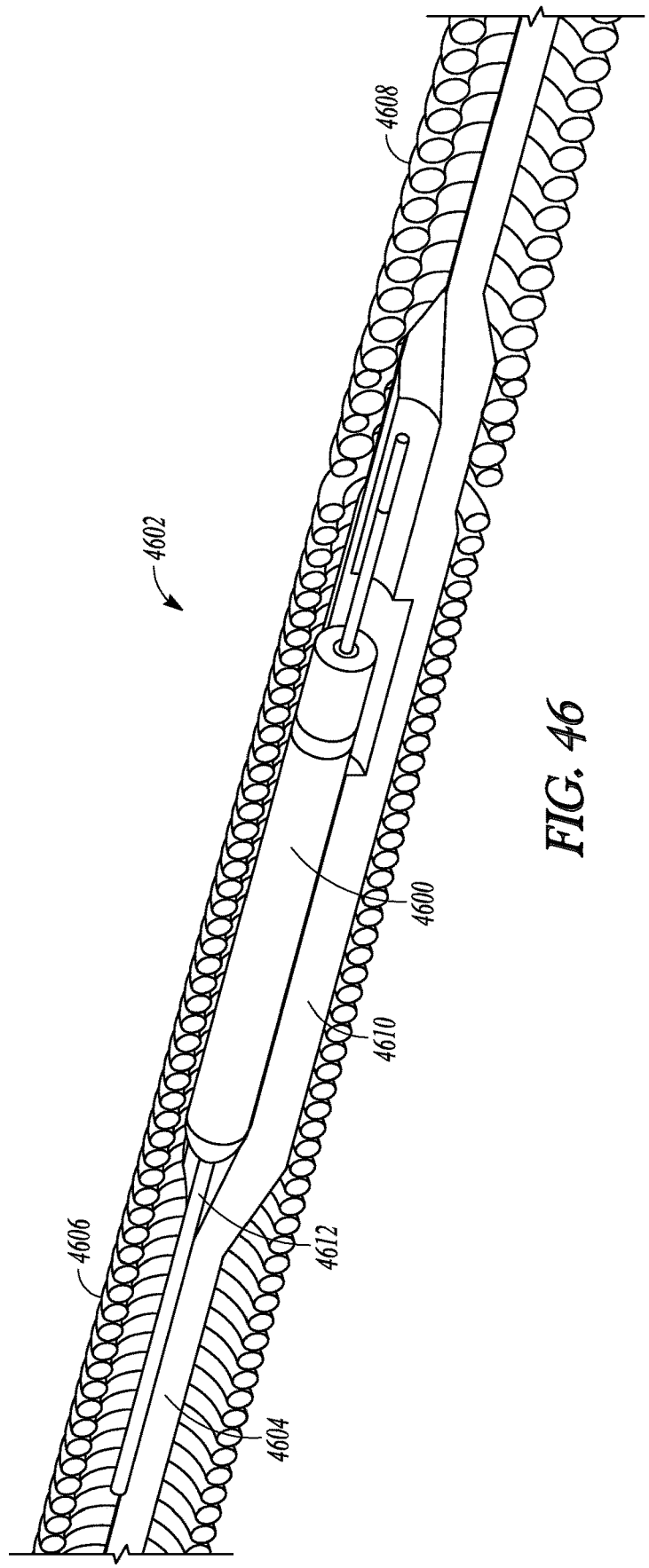
FIG. 46 depicts an example of a guidewire in combination with an optical fiber pressure sensor and the core wire of FIG. 45B.

After the core wire 4500 has been manufactured to the desired dimensions, a cradle can be formed, e.g., using a coining process, in the portion(s) with a larger diameter, as shown generally at 4510 in FIG. 45B. The cradle 4510 formed in the core wire 4500 can be used to provide a housing for a pressure sensor assembly, e.g., assemblies 3900, 4000, and 4100 of FIGS. 39-41, as shown in FIG. 46. Such a design can be advantageous because a single structure can function both as the core wire 4500 and as the housing of a pressure sensor assembly, which can improve its strength. In addition, the design of FIG. 45B can be advantageous because the core wire 4500 is coaxial with the guidewire, as shown in FIG. 46, which can enhance the performance of the guidewire. For example, the guidewire can improve the steering of the guidewire and allow the guidewire to perform more predictably, e.g., without whip or latency, which can be important while assessing a lesion.

FIG. 46 depicts an example of a guidewire in combination with an optical fiber pressure sensor and the core wire of FIG. 45B. In FIG. 46, an optical pressure sensor assembly 4600, e.g., assemblies 3900, 4000, and 4100 of FIGS. 39-41, can be delivered to a desired site using a guidewire, shown generally at 4602. The guidewire 4602 can include a core wire 4604, e.g., the core wire 4500 of FIG. 45B, a proximal coil 4606, and a distal coil 4608. As described above, the core wire 4604 can be formed to include a cradle 4610, e.g., the cradle 4510 of FIG. 45B, which can hold the pressure sensor assembly 4600. An optical fiber 4612 can extend along the core wire 4604 without contacting the core wire 4604. As seen in FIG. 46, the core wire 4604 is coaxial with the guidewire 4602, which can enhance the performance of the guidewire.

Using the one or more techniques such as disclosed herein, the present applicant has described an optical pressure sensing guidewire suitable for delivery within a body lumen of a patient, e.g., for diagnostic assessment of coronary obstructions. This can advantageously optionally provide temperature compensation for sensing pressure within a body lumen. In addition, the present subject matter can advantageously mechanically enhance the sensitivity of the fiber to pressure, such as with an extrinsic arrangement. Further, the present subject matter can utilize Fiber Bragg Gratings in the miniaturized optical fiber thereby resulting in a cost effective and manufacturable design.

Example 1 can include or use subject matter (e.g., a system, apparatus, method, article, machine readable medium, or the like) that can include or use an elongated assembly. At least a portion of the elongated assembly can be sized, shaped, or otherwise configured to be inserted into a human body (e.g., the vasculature), such as to measure a physiological parameter at an internal location within the body. The elongated assembly can include an elongated member having a length. At least a portion of the elongated member can define a longitudinal optical fiber carrier that can extend longitudinally along at least a portion of the length of the elongated member. The optical fiber carrier can include at least one of a groove or a flat. An optical fiber can extend longitudinally along the optical fiber carrier. The optical fiber can be configured to communicate light between a location outside of the body and a portion of the optical fiber that is to be located at or near the internal location within the body at which physiological parameter is to be measured.

Example 2 can include or use (or can optionally be combined with at least some features of Example 1) to include or use the optical fiber carrier being sized for and carrying only one optical fiber. The only one optical fiber can have a diameter of between 25 micrometers and 30 micrometers, inclusive.

Example 3 can include or use (or can optionally be combined with at least some features of any one or more of Example 1 or 2) to include or use the optical fiber carrier extending helically along at least a portion of the length of the elongated member.

Example 4 can include or use (or can optionally be combined with at least some features of any one or more of Examples 1 through 3) to include or use the optical fiber carrier including a groove in the elongated member.

Example 5 can include or use (or can optionally be combined with at least some features of any one or more of Examples 1 through 4) to include or use the optical fiber carrier includes a flat in an outer surface of the elongated member.

Example 6 can include or use (or can optionally be combined with at least some features of any one or more of Examples 1 through 5) to include or use the elongated member comprises multiple filaments. An interstice between adjacent filaments can define at least a portion of the optical fiber carrier.

Example 7 can include or use (or can optionally be combined with at least some features of any one or more of Examples 1 through 6) to include or use the apparatus wherein the physiological parameter is a pressure. The apparatus can include at least one optical fiber pressure sensor that can be configured to be located on the elongated assembly such as to allow positioning at or near the internal location within the body at which pressure is to be measured.

Example 8 can include or use (or can optionally be combined with at least some features of any one or more of Examples 1 through 6) to include or use at least one optical fiber pressure sensor comprising a Fiber Bragg Grating (FBG) interferometer.

Example 9 can include or use (or can optionally be combined with at least some features of any one or more of Examples 1 through 8) to include or use an FBG interferometer that can comprise at least two Fiber Bragg Gratings. The at least two Fiber Bragg Gratings can be arranged or otherwise configured to permit optically discriminating, at or near the internal location within the body at which pressure is to be measured, between a change in pressure and a change in temperature.

Example 10 can include or use (or can optionally be combined with at least some features of any one or more of Examples 1 through 9) to include or use at least one optical fiber pressure sensor that can comprise two or more optical fiber pressure sensors that can be configured to operate at different wavelengths.

Example 11 can include or use (or can optionally be combined with at least some features of any one or more of Examples 1 through 10) to include or use an optical fiber ribbon that can comprise a plurality of optical fibers. The optical fiber ribbon can be disposed about an outer surface of the elongated member.

Example 12 can include or use (or can optionally be combined with at least some features of any one or more of Examples 1 through 11) to include or use a plurality of imaging gratings that can be configured to couple light into or out of one or more respective optical fibers of the ribbon.

Example 13 can include or use (or can optionally be combined with at least some features of any one or more of Examples 1 through 12) to include or use an elongated member being or including a guidewire.

Example 14 can include or use (or can optionally be combined with at least some features of any one or more of Examples 1 through 13) to include or use the optical fiber pressure sensor comprising a compliant sensor membrane or member. The compliant membrane or member can be configured to mechanically couple received pressure toward an FBG interferometer.

Example 15 can include or use (or can optionally be combined with at least some features of any one or more of Examples 1 through 14) to include or use the optical fiber pressure sensor comprising a support member adjacent to the sensor membrane. The optical fiber can span and can be mechanically coupled to the support member and the sensor membrane. A first portion of the optical fiber can be mechanically coupled to the support member so as to be relatively less sensitive to a change in pressure than a second portion of the optical fiber that is mechanically coupled to the sensor membrane.

Example 16 can include or use (or can optionally be combined with at least some features of any one or more of Examples 1 through 15) to include or use a sheath disposed about the support member and at least a first portion of the sensor membrane. A portion of an outer diameter of the pressure sensor can be defined by the sheath and a second portion of the sensor membrane. A portion of the sheath and a portion of the support member can at least partially define a cavity.

Example 17 can include or use (or can optionally be combined with at least some features of any one or more of Examples 1 through 16) to include or use a mechanical coupling, such as between the sensor membrane and the FBG interferometer. The mechanical coupling can change from a relatively larger area at the sensor membrane to a relatively smaller area at the FBG interferometer, such as to concentrate a force at the FBG interferometer produced by a pressure or a stress at the sensor membrane.

Example 18 can include or use (or can optionally be combined with at least some features of any one or more of Examples 1 through 17) to include or use the mechanical coupling being configured to contact a surface between two Fiber Bragg Gratings positioned away from the support member.

Example 19 can include or use (or can optionally be combined with at least some features of any one or more of Examples 1 through 18) to include or use the support member comprising a first support member and a second support member distal to the first support member. The sensor membrane and the optical fiber can span the first and second support members.

Example 20 can include or use (or can optionally be combined with at least some features of any one or more of Examples 1 through 19) to include or use the optical fiber spanning the first and second support members between Fiber Bragg Gratings in the optical fiber that are located at and supported by the first and second support members.

Example 21 can include or use (or can optionally be combined with at least some features of any one or more of Examples 1 through 20) to include or use a first outer diameter and a second outer diameter that is less than the first outer diameter. The elongated member can include a first tube disposed about a portion of the optical fiber. A second tube can be disposed about the first tube. The second tube can be engaged to the elongated member at the second outer diameter.

Example 22 can include or use (or can optionally be combined with at least some features of any one or more of Examples 1 through 21) to include or use a first tube is disposed about a portion of the optical fiber that includes four Fiber Bragg Gratings.

Example 23 can include or use (or can optionally be combined with at least some features of any one or more of Examples 1 through 22) to include or use the first tube being disposed about a first and second of three Fiber Bragg Gratings. The second tube can be disposed about the first tube and a third of the three Fiber Bragg Gratings.

Example 24 can include or use (or can optionally be combined with at least some features of any one or more of Examples 1 through 23) to include or use the elongated member defining a cavity in which a microballoon can be positioned.

Example 25 can include or use (or can optionally be combined with at least some features of any one or more of Examples 1 through 24) to include or use the optical fiber pressure sensor comprising a first optical fiber anchor, to which a first portion of the optical fiber can be secured. A second optical fiber anchor can be included, to which a second portion of the optical fiber can be secured. A gasket can be longitudinally arranged between the first and second anchors. The gasket can include a passage through which a third portion of the optical fiber passes. The gasket can be more elastic or compliant than the first and second anchors. The first and second anchors and the gasket can be arranged to use the elastic or compliant nature of the gasket to allow at least one of longitudinal stretching or compression of the optical fiber between the first and second anchors to sense pressure at the internal location within the body.

Example 26 can include or use (or can optionally be combined with at least some features of any one or more of Examples 1 through 25) to include or use the optical fiber being arranged under longitudinal tension between the first and second anchors.

Example 27 can include or use (or can optionally be combined with at least some features of any one or more of Examples 1 through 26) to include or use the elongated assembly including a spring coil arranged coaxially to a longitudinal axis of the elongated assembly. A connector block can be coupled to the spring coil. The connector block can include the optical fiber pressure sensor being arranged with the compliant gasket exposed such as to receive an ambient pressure at the internal location within the body.

Example 28 can include or use (or can optionally be combined with at least some features of any one or more of Examples 1 through 27) to include or use the elongated member including a jog to accommodate the optical fiber pressure sensor.

Example 29 can include or use (or can optionally be combined with at least some features of any one or more of Examples 1 through 28) to include or use the optical fiber pressure sensor being located at a distal tip of the elongated assembly.

Example 30 can include or use (or can optionally be combined with at least some features of any one or more of Examples 1 through 24) to include or use the optical fiber being a first optical fiber, and comprising a proximal end connector, configured to be coupled to a proximal end of the elongated member. The proximal end connector can comprise a distal portion and a proximal portion. The distal portion can include a tube, which can define an interior first passage that can be sized and shaped to receive the proximal end of the elongated member. The distal portion can include a distal guide ferrule, at least a portion of which can define a transitional interior second passage that can be sized and shaped to allow the optical fiber to be transitionally routed from an outer circumferential periphery of the proximal end of the elongated member to a more longitudinally central location toward a proximal end of the distal guide ferrule. The proximal portion can include a proximal guide ferrule. The proximal guide ferrule can include a lumen sized and shaped for passing a second optical fiber having a larger diameter than the first optical fiber. The distal and proximal portions can be user-attachable, such as to bring the first and second optical fibers into concentric longitudinal alignment with each other.

Example 31 can include or use (or can optionally be combined with at least some features of any one or more of Examples 1 through 30) to include or use a split sleeve ferrule holding and concentrically aligning at least a portion of the distal guide ferrule against a portion of the proximal guide ferrule.

Example 32 can include or use (or can optionally be combined with at least some features of any one or more of Examples 1 through 32) to include or use a coil disposed about at least a portion of the elongated member.

Example 33 can include or use (or can optionally be combined with at least some features of any one or more of Examples 1 through 32) to include or use an apparatus for insertion into a body lumen. The apparatus can comprise an optical fiber pressure sensor. The optical fiber pressure sensor can comprise an optical fiber that can be configured to carry an optical sensing signal. A compliant sensor membrane can be in physical communication with a first portion of the optical fiber. The membrane can be configured to communicate a received pressure to the FBG interferometer. A support structure can be in physical communication with a second portion of the optical fiber. The second portion of the optical fiber can be configured with less sensitivity to a change in the received pressure than the first portion of the optical fiber.

Example 34 can include or use (or can optionally be combined with at least some features of any one or more of Examples 1 through 33) to include or use a guidewire including a distal portion carrying the optical fiber pressure sensor.

Example 35 can include or use (or can optionally be combined with at least some features of any one or more of Examples 1 through 34) to include or use the optical fiber being a single fiber having a diameter of between about 25 micrometers and about 30 micrometers, inclusive.

Example 36 can include or use (or can optionally be combined with at least some features of any one or more of Examples 1 through 35 to include or use a system that can comprise a controller circuit. The controller circuit can be configured to control light transmitted from a laser via an optical fiber toward an optical fiber pressure sensor. The transmitted light can have a first wavelength. The optical fiber pressure sensor can be configured to reflect a light signal having a reflection band including the first wavelength. The controller circuit can be configured to: set the first wavelength on a point on a slope of a notch of the reflection band; track a position of the point on the slope; determine a shift in the first wavelength using a change in the position of the point; and determine a pressure reading using the determined shift in the first wavelength.

Example 37 can include or use (or can optionally be combined with at least some features of any one or more of Examples 1 through 36) to include or use a system comprising an elongated assembly, at least a portion of which can be sized, shaped, or otherwise configured to be inserted into a body, such as to measure a pressure at an internal location within the body. The elongated assembly can include an elongated member having a length. At least a portion of the elongated member can define a longitudinal optical fiber carrier that can extend longitudinally along at least a portion of the length of the elongated member. An optical fiber can extend longitudinally along the optical fiber carrier. The optical fiber can be configured to communicate light between a location outside of the body and a portion of the optical fiber that is to be located at or near the internal location within the body at which pressure is to be measured. The elongated assembly can include the optical fiber pressure sensor.

Example 38 can include or use (or can optionally be combined with at least some features of any one or more of Examples 1 through 37) to include or use the controller circuit being configured to modulate a drive current of the laser providing the light.

Example 39 can include or use (or can optionally be combined with at least some features of any one or more of Examples 1 through 38) to include or use the controller circuit being configured to: receive information indicating an operating temperature of the laser; convert the information indicating the operating temperature of the laser to information indicating an unintended drift in the first wavelength; and adjust the pressure reading based on the information indicating the unintended drift in the first wavelength.

Example 40 can include or use (or can optionally be combined with at least some features of any one or more of Examples 1 through 39) to include or use the laser being a first laser, and wherein the notch is a first notch. The controller circuit can be configured to control light transmitted from a second laser via the optical fiber toward the optical fiber sensor. The transmitted light can have a second wavelength. The optical fiber pressure sensor can be configured to reflect a light signal having a reflection band including the second wavelength. The controller circuit can be configured to: set the second wavelength on a second point on a slope of a second notch of the reflection band; track a position of the second point on the slope of the second notch; determine a shift in the second wavelength using a change in the position of the second point; and determine an ambient temperature reading based on the determined shift in the second wavelength.

Example 41 can include or use (or can optionally be combined with at least some features of any one or more of Examples 1 through 40) to include or use the controller circuit being further configured to: receive information indicating an operating temperature of the second laser; convert the information indicating the operating temperature of the second laser to information indicating an unintended drift in the second wavelength; and adjust the pressure reading based on the information indicating the unintended drift in the second wavelength.

Example 42 can include or use (or can optionally be combined with at least some features of any one or more of Examples 1 through 41) to include or use at least one optical polarization state modifier; wherein the controller circuit can be configured to generate a plurality of optical polarization states during a pressure sampling interval using the at least one optical polarization state modifier to nullify substantially all birefringence effects of the optical fiber.

Example 43 can include or use (or can optionally be combined with at least some features of any one or more of Examples 1 through 42) to include or use the controller circuit being configured to compensate for a change in an optical insertion loss.

Example 44 can include or use (or can optionally be combined with at least some features of any one or more of Examples 1 through 43) to include or use the controller circuit being configured to compensate for the change in an optical insertion loss such as by calculating and adjusting an optical locking level such as by controlling application of a dither signal.

Example 45 can include or use (or can optionally be combined with at least some features of any one or more of Examples 1 through 44) to include or use the controller circuit being configured to: generate a dither signal at a frequency outside of a range associated with a pressure signal; receive a reflected optical signal from the optical fiber pressure sensor; remove or suppress an AC component at the dither signal frequency; determine a low frequency value over a specified region of interest of the signal; and determine a noise compensated optical locking wavelength based on the determined low frequency value.

Example 46 can include or use (or can optionally be combined with at least some features of any one or more of Examples 1 through 45) to include or use an elongated member, at least a portion of which can be sized, shaped, or otherwise configured to be inserted into a human body to measure pressure and perform imaging at an internal location within the body. The elongated member can include: an acoustic imaging transducer configured to image a region at or near the internal location within the body and to detect a responsive imaging signal for communication via the elongated member to a location outside of the body for processing into an image of the region; and a pressure transducer, configured to measure a pressure at or near the internal location and to communicate a responsive pressure signal via the elongated member to a location outside of the body.

Example 47 can include or use (or can optionally be combined with at least some features of any one or more of Examples 1 through 46) to include or use the elongated member comprising a guidewire that can be sized, shaped, or otherwise configured for intravascularly delivering a coronary stent to an intravascular location within a heart located in the body.

Example 48 can include or use (or can optionally be combined with at least some features of any one or more of Examples 1 through 47) to include or use an apparatus that can comprise a proximal end connector, which can be configured to be coupled to a proximal end of an elongated member. The proximal end connector can include a distal portion and a proximal portion. The distal portion can comprise a tube, which can define an interior first passage that can be sized and shaped to receive the proximal end of the elongated member. The distal portion can include a distal guide ferrule, at least a portion of which can define a transitional interior second passage that can be sized and shaped to allow a first optical fiber to be transitionally routed from an outer circumferential periphery of the proximal end of the elongated member to a more longitudinally central location toward a proximal end of the distal guide ferrule. The proximal portion can include a proximal guide ferrule. The proximal guide ferrule can include a lumen that can be sized and shaped for passing a second optical fiber having a larger diameter than the first optical fiber. The distal and proximal portions can be user-attachable to bring the first and second optical fibers into concentric longitudinal alignment with each other.

Example 49 can include or use (or can optionally be combined with at least some features of any one or more of Examples 1 through 48) to include or use a split sleeve ferrule that can hold and concentrically align at least a portion of the distal guide ferrule against a portion of the proximal guide ferrule.

Example 50 can include or use (or can optionally be combined with at least some features of any one or more of Examples 1 through 49) to include or use an optical fiber pressure sensor apparatus that can include a first optical fiber anchor, to which a first portion of the optical fiber is secured. A second optical fiber anchor can be included, to which a second portion of the optical fiber can be secured. A gasket can be longitudinally arranged between the first and second anchors and can include a passage through which a third portion of the optical fiber passes. The gasket can be more elastic or compliant than the first and second anchors. The first and second anchors and the gasket can be arranged to use the elastic or compliant nature of the gasket such as to allow at least one of longitudinal stretching or longitudinal compression of the optical fiber between the first and second anchors to sense pressure at an internal location within a human body. The optical fiber can be a single fiber having a diameter of between about 25 micrometers and about 30 micrometers, inclusive.

Example 51 can include or use (or can optionally be combined with at least some features of any one or more of Examples 1 through 50) to include or use the optical fiber being arranged under longitudinal tension between the first and second anchors.

Example 52 can include or use (or can optionally be combined with at least some features of any one or more of Examples 1 through 51) to include or use the optical fiber pressure sensor being carried on an elongated assembly that can include a spring coil that can be arranged coaxially to a longitudinal axis of the elongated assembly. The apparatus can comprise a connector block that can be coupled to the spring coil. The connector block can include the optical fiber pressure sensor being arranged with the compliant gasket exposed to receive an ambient pressure at the internal location within the body.

Example 53 can include or use (or can optionally be combined with at least some features of any one or more of Examples 1 through 52) to include or use the optical fiber pressure sensor being carried on an elongated assembly sized to intravascularly deliver a coronary stent to an intravascular location within a heart.

Example 54 can include or use (or can optionally be combined with at least some features of any one or more of Examples 1 through 53) to include or use the optical fiber including first and second Fiber Bragg Gratings (FBGs). The first FBG can be located at the first anchor and the second FBG can extends distally beyond the second anchor.

Example 55 can include or use (or can optionally be combined with at least some features of any one or more of Examples 1 through 54) to include or use the second FBG also being located at the second anchor.

Example 56 can include or use (or can optionally be combined with at least some features of any one or more of Examples 1 through 55) to include or use at least one of the first and second FBGs spans at least a portion of the gasket.

Example 57 can include or use (or can optionally be combined with at least some features of any one or more of Examples 1 through 56) to include or use the second FBG being located at a positive separation distance apart from the second anchor.

Example 58 can include or use (or can optionally be combined with at least some features of any one or more of Examples 1 through 57) to include or use the optical fiber including first and second Fiber Bragg Gratings (FBGs). The first FBG can be located at the first anchor and the second FBG can extend distally beyond the second anchor.

Example 59 can include or use (or can optionally be combined with at least some features of any one or more of Examples 1 through 58) to include or use the second FBG also being located at the second anchor.

Example 60 can include or use (or can optionally be combined with at least some features of any one or more of Examples 1 through 59) to include or use at least one of the first and second FBGs spanning at least a portion of the gasket.

Example 61 can include or use (or can optionally be combined with at least some features of any one or more of Examples 1 through 60) to include or use the second FBG being located at a positive separation distance apart from the second anchor.

Example 62 can include or use (or can optionally be combined with at least some features of any one or more of Examples 1 through 61) to include or use a system comprising a controller circuit, including an optical insertion loss compensation circuit that is configured to compensate for a change in an optical insertion loss, and an apparatus comprising an elongated assembly, at least a portion of which can be sized, shaped, or otherwise configured to be inserted into a human body to measure a physiological parameter at an internal location within the body. The elongated assembly can include an elongated member having a length, wherein at least a portion of the elongated member can define a longitudinal optical fiber carrier that can extend longitudinally along at least a portion of the length of the elongated member. The optical fiber carrier can include at least one of a groove or a flat. An optical fiber can extend longitudinally along the optical fiber carrier, the optical fiber can be configured to communicate light between a location outside of the body and a portion of the optical fiber that is to be located at or near the internal location within the body at which physiological parameter is to be measured.

Example 63 can include or use (or can optionally be combined with at least some features of any one or more of Examples 1 through 62) to include or use a system comprising a controller circuit configured to generate a plurality of optical polarization states during a pressure sampling interval using an optical polarization state modifier to nullify or negate birefringence of the optical fiber and further comprising an apparatus. The apparatus can comprise an elongated assembly, at least a portion of which can be sized, shaped, or otherwise configured to be inserted into a human body to measure a physiological parameter at an internal location within the body. The elongated assembly can includes an elongated member having a length, wherein at least a portion of the elongated member can define a longitudinal optical fiber carrier that can extend longitudinally along at least a portion of the length of the elongated member. The optical fiber carrier can include at least one of a groove or a flat. An optical fiber can extend longitudinally along the optical fiber carrier. The optical fiber can be configured to communicate light between a location outside of the body and a portion of the optical fiber that is to be located at or near the internal location within the body at which physiological parameter is to be measured.

Example 64 can include or use (or can optionally be combined with at least some features of any one or more of Examples 1 through 63) to include or use an apparatus comprising a proximal end connector, configured to be coupled to a proximal end of an elongated intravascular guidewire. The proximal end connector can comprise a distal portion and a proximal portion. The distal portion can comprise a tube, defining an interior first passage that is sized and shaped to receive the proximal end of the elongated intravascular guidewire. A distal guide ferrule can be included, at least a portion of which defines an interior second passage that is sized and shaped to pass a first optical fiber toward a proximal end of the distal guide ferrule. The proximal portion can comprise a proximal guide ferrule, including a lumen sized and shaped for passing a second optical fiber having a larger diameter than the first optical fiber. The distal and proximal portions can be user-attachable such as to bring the first and second optical fibers into concentric longitudinal alignment with each other.

Example 65 can include or use (or can optionally be combined with at least some features of any one or more of Examples 1 through 64) to include or use a split sleeve ferrule holding and concentrically aligning at least a portion of the distal guide ferrule against a portion of the proximal guide ferrule.

Example 66 can include or use (or can optionally be combined with at least some features of any one or more of Examples 1 through 65) to include or use an apparatus for insertion into a body lumen. The apparatus can comprise an optical fiber pressure sensor comprising: an optical fiber configured to transmit an optical sensing signal; an ambient temperature compensated Fiber Bragg Grating (FBG) interferometer in optical communication with the optical fiber, the FBG interferometer configured to receive a pressure and modulate, in response to the received pressure, the optical sensing signal; and a sensor membrane in physical communication with the FBG interferometer, the membrane configured to transmit the received pressure to the FBG interferometer.

Example 67 can include or use (or can optionally be combined with at least some features of any one or more of Examples 1 through 66) to include or use a guidewire.

Example 68 can include or use (or can optionally be combined with at least some features of any one or more of Examples 1 through 67) to include or use the optical fiber being a single fiber having a diameter of between about 25 micrometers and about 30 micrometers.

Example 69 can include or use (or can optionally be combined with at least some features of any one or more of Examples 1 through 68) to include or use an intravascular guidewire having proximal and distal ends. The guidewire can comprise: an elongated high strength proximal portion having proximal and distal ends; a distal portion having proximal and distal ends formed of a superelastic alloy in an austenite phase at body temperature, which transforms to a martensite phase when subjected to stress; and means for connecting the distal end of the proximal portion and the proximal end of the distal portion, which is formed at least in part of a superelastic alloy in an austenite phase which transforms to a martensite phase when subjected to stress.

Example 70 can include or use (or can optionally be combined with at least some features of any one or more of Examples 1 through 69) to include or use an apparatus comprising an elongated assembly, at least a portion of which can be sized, shaped, or otherwise configured to be inserted into a human or animal body to measure a pressure at an internal location within the body. The elongated assembly can include: an optical fiber, configured to communicate light between a location outside the body and a portion of the optical fiber that is located at or near the internal location; and a pressure sensor assembly including a compliant element that is arranged to permit longitudinal spatial variation in at least a portion of the optical fiber in response to a pressure variation at the internal location within the body.

Example 71 can include or use (or can optionally be combined with at least some features of any one or more of Examples 1 through 70) to include or use an optical fiber that includes a first sensing region, affixed to the pressure sensor assembly so as to inhibit or prevent longitudinal spatial variation of the optical fiber in the first sensing region in response to the pressure variation at the internal location within the body. A second sensing region can be suspended with respect to at least a portion of the pressure sensor assembly so as to permit longitudinal spatial variation of the optical fiber in the second sensing region in response to the pressure variation at the internal location within the body.

Example 72 can include or use (or can optionally be combined with at least some features of any one or more of Examples 1 through 70) to include or use the first and second sensing regions being configured to have similar temperature sensitivities and dissimilar pressure sensitivities.

Example 73 can include or use (or can optionally be combined with at least some features of any one or more of Examples 1 through 72) to include or use the second sensing region including at least a portion that is suspended within a housing of the pressure sensor assembly.

Example 74 can include or use (or can optionally be combined with at least some features of any one or more of Examples 1 through 73) to include or use the elongated assembly including first and second guidewire spring coil regions. At least a portion of the pressure sensor assembly can be located between the first and second guidewire spring coil regions.

Example 75 can include or use (or can optionally be combined with at least some features of any one or more of Examples 1 through 74) to include or use the elongated assembly includes a guidewire core.

Example 76 can include or use (or can optionally be combined with at least some features of any one or more of Examples 1 through 75) to include or use the compliant element being configured to be exposed or accessible to pressure variation lateral to at least a portion of the elongated assembly.

Example 77 can include or use (or can optionally be combined with at least some features of any one or more of Examples 1 through 76) to include or use the compliant element being configured to be exposed or accessible to pressure variation longitudinally distal to a distal end of the elongated assembly.

Example 78 can include or use (or can optionally be combined with at least some features of any one or more of Examples 1 through 77) to include or use the optical fiber being helically wound about at least a portion of the elongated assembly.

Example 79 can include or use (or can optionally be combined with at least some features of any one or more of Examples 1 through 78) to include or use the optical fiber being located at an atraumatic distal tip region of the elongated assembly.

Example 80 can include or use (or can optionally be combined with at least some features of any one or more of Examples 1 through 79) to include or use a proximal connector assembly being located at a proximal end of the elongated assembly. The proximal connector can comprise a first module. The first module can comprise a first ferrule, including a first through lumen sized and shaped to securely carry a proximal portion of the optical fiber through the first ferrule. The first module can also comprise a tubular coupler, connecting a guidewire body and the first ferrule with the optical fiber extending therebetween.

Example 81 can include or use (or can optionally be combined with at least some features of any one or more of Examples 1 through 80) to include or use the proximal connector comprising a second module, which can be user-attachable and user-detachable from the first module. The second module can comprise a second ferrule, which can include a second through lumen that can be sized and shaped to securely carry a distal portion of an external instrumentation lead optical fiber through the second ferrule. The second module can include an alignment feature that can permit alignment of the optical fiber in the first ferrule with the external instrumentation lead optical fiber in the second ferrule when the first and second modules are connected.

Example 82 can include or use (or can optionally be combined with at least some features of any one or more of Examples 1 through 81) to include or use a system comprising a controller and an apparatus for insertion into a body lumen, the apparatus comprising: an optical fiber device comprising an optical fiber configured to transmit an optical signal. The controller can be configured to compensate for changes in an optical insertion loss of the apparatus.

Example 83 can include or use (or can optionally be combined with at least some features of any one or more of Examples 1 through 82) to include or use the controller being configured to calculate and adjust an optical locking level by controlling the application of a dither signal to a tracking laser.

Example 84 can include or use (or can optionally be combined with at least some features of any one or more of Examples 1 through 83) to include or use applying the dither signal generates a signal having an amplitude that is proportional to the optical insertion loss. The controller can be configured to determine a change in a laser current based on the amplitude of the generated signal to compensate for the insertion loss.

Example 85 can include or use (or can optionally be combined with at least some features of any one or more of Examples 1 through 84) to include or use the optical fiber device including an optical pressure sensing device.

Example 86 can include or use (or can optionally be combined with at least some features of any one or more of Examples 1 through 85) to include or use the optical fiber device including an optical imaging device.

Example 87 can include or use (or can optionally be combined with at least some features of any one or more of Examples 1 through 86) to include or use a method for compensating for insertion loss in an optical fiber apparatus for insertion into a body lumen. The method can comprise: determining an optical locking level with no excess insertion loss; determining a first amplitude of a dither signal; determining a second amplitude of the dither signal; comparing the first and second amplitudes; determining whether the insertion loss has changed based on the comparison; and adjusting the optical locking level in response to determining that the insertion loss has changed.

Example 88 can include or use (or can optionally be combined with at least some features of any one or more of Examples 1 through 87) to include or use a system comprising an apparatus for insertion into a body lumen. The apparatus can comprise: an optical fiber device comprising an optical fiber configured to transmit an optical signal; and a controller that can be configured to compensate for optical cavity noise of the apparatus.

Example 89 can include or use (or can optionally be combined with at least some features of any one or more of Examples 1 through 88) to include or use the controller configured to compensate for optical cavity noise of the apparatus being configured to determine an optical locking wavelength by controlling the application of a dither signal to a tracking laser.

Example 90 can include or use (or can optionally be combined with at least some features of any one or more of Examples 1 through 89) to include or use the controller being further configured to: determine an average signal value of a component extracted at a frequency of the dither signal from an optical signal; and determine the optical locking wavelength based on the determined average signal value.

Example 91 can include or use (or can optionally be combined with at least some features of any one or more of Examples 1 through 90) to include or use a method for compensating for optical cavity noise in an optical fiber apparatus for insertion into a body lumen. The method can comprise: generating a dither signal at a frequency outside range associated with a pressure signal; receiving a reflected optical signal from a pressure sensor of the apparatus; removing a component of the optical signal at the dither signal frequency; determining an average value over a specified region of interest of the signal; and determining an optical locking wavelength based on the determined average value.

Example 92 can include or use (or can optionally be combined with at least some features of any one or more of Examples 1 through 91) to include or use an apparatus for insertion into a body lumen. The apparatus can comprise an elongated assembly, at least a portion of which can be sized, shaped, or otherwise configured to be inserted into a human body to measure a physiological parameter at an internal location within the body. The elongated assembly can include: an elongated member having a length, wherein at least a portion of the elongated member defines a longitudinal optical fiber carrier that extends longitudinally along at least a portion of the length of the elongated member, wherein the optical fiber carrier includes at least one of a groove or a flat; an optical fiber, extending longitudinally along the optical fiber carrier, the optical fiber configured to communicate light between a location outside of the body and a portion of the optical fiber that is to be located at or near the internal location within the body at which physiological parameter is to be measured, wherein the optical fiber comprises first and second Fiber Bragg Gratings (FBGs). The apparatus can include an optical fiber pressure sensor apparatus comprising: a first optical fiber anchor, to which a first portion of the optical fiber is secured; a second optical fiber anchor, to which a second portion of the optical fiber is secured; and a gasket longitudinally arranged between the first and second anchors and including a passage through which a third portion of the optical fiber passes, the gasket being more elastic or compliant than the first and second anchors; and wherein the first and second anchors and the gasket are arranged to use the elastic or compliant nature of the gasket to allow at least one of longitudinal stretching or longitudinal compression of the optical fiber between the first and second anchors to sense pressure at an internal location within a human body; wherein the first FBG is located at the first anchor and the second FBG extends distally beyond the second anchor; first and second spacers, wherein a proximal portion of the optical fiber extends through a hole defined by the first spacer, and wherein a distal portion of the optical fiber extends through a hole defined by the second spacer; and a mounting unit configured to affix the optical fiber pressure sensor apparatus to the elongated member.

Example 93 can include or use (or can optionally be combined with at least some features of any one or more of Examples 1 through 92) to include or use an apparatus for insertion into a body lumen. The apparatus can include an elongated assembly, at least a portion of which can be sized, shaped, or otherwise configured to be inserted into a human body to measure a physiological parameter at an internal location within the body. The elongated assembly can include an elongated member having a length. At least a portion of the elongated member can define a longitudinal optical fiber carrier that can extend longitudinally along at least a portion of the length of the elongated member. The optical fiber carrier can include at least one of a groove or a flat. An optical fiber can extend longitudinally along the optical fiber carrier. The optical fiber can be configured to communicate light between a location outside of the body and a portion of the optical fiber that is to be located at or near the internal location within the body at which physiological parameter is to be measured. The optical fiber can comprise first and second Fiber Bragg Gratings (FBGs). An optical fiber pressure sensor apparatus can be included, comprising: a first optical fiber anchor, to which a first portion of the optical fiber is secured; a second optical fiber anchor, to which a second portion of the optical fiber is secured; and a gasket longitudinally arranged between the first and second anchors and including a passage through which a third portion of the optical fiber passes, the gasket being more elastic or compliant than the first and second anchors. The first and second anchors and the gasket can be arranged to use the elastic or compliant nature of the gasket to allow at least one of longitudinal stretching or longitudinal compression of the optical fiber between the first and second anchors to sense pressure at an internal location within a human body. The first FBG can be located at the first anchor and the second FBG can extend distally beyond the second anchor. An elongated support can be disposed about a portion of the elongated member and at least a portion of the optical fiber pressure sensor apparatus. A mounting material can be configured to affix the optical fiber pressure sensor apparatus to the elongated member within the elongated support.

Example 94 can include or use (or can optionally be combined with at least some features of any one or more of Examples 1 through 93) to include or use an apparatus for insertion into a body lumen. The apparatus can comprise an elongated assembly, at least a portion of which can be sized, shaped, or otherwise configured to be inserted into a human body to measure a physiological parameter at an internal location within the body. The elongated assembly can include an elongated member having a length. At least a portion of the elongated member can define a longitudinal optical fiber carrier that can extends longitudinally along at least a portion of the length of the elongated member. The optical fiber carrier can include at least one of a groove or a flat. An optical fiber can extending longitudinally along the optical fiber carrier. The optical fiber can be configured to communicate light between a location outside of the body and a portion of the optical fiber that is to be located at or near the internal location within the body at which physiological parameter is to be measured. The optical fiber can comprise first and second Fiber Bragg Gratings (FBGs). An optical fiber pressure sensor apparatus can be included, comprising: a first optical fiber anchor, to which a first portion of the optical fiber is secured; a second optical fiber anchor, to which a second portion of the optical fiber is secured; and a gasket longitudinally arranged between the first and second anchors and including a passage through which a third portion of the optical fiber passes, the gasket being more elastic or compliant than the first and second anchors. The first and second anchors and the gasket can be arranged to use the elastic or compliant nature of the gasket to allow at least one of longitudinal stretching or longitudinal compression of the optical fiber between the first and second anchors to sense pressure at an internal location within a human body. The first FBG can be located at the first anchor and the second FBG can extend distally beyond the second anchor. A tubular assembly can be disposed about a portion of the elongated member. The tubular assembly can be configured to receive the optical fiber pressure sensor apparatus. The tubular assembly can define a circumference having an opening along a length of the tubular assembly. A mounting material can be configured to affix the optical fiber pressure sensor apparatus to the elongated member within the tubular assembly.

Example 95 can include or use (or can optionally be combined with at least some features of any one or more of Examples 1 through 94) to include or use an apparatus for insertion into a body lumen. The apparatus can comprise an elongated assembly, at least a portion of which can be sized, shaped, or otherwise configured to be inserted into a human body such as to measure a physiological parameter at an internal location within the body. The elongated assembly can include an elongated member having a length. At least a portion of the elongated member can define a longitudinal optical fiber carrier that can extend longitudinally along at least a portion of the length of the elongated member. The optical fiber carrier can include at least one of a groove or a flat. An optical fiber can extend longitudinally along the optical fiber carrier. The optical fiber can be configured to communicate light between a location outside of the body and a portion of the optical fiber that is to be located at or near the internal location within the body at which physiological parameter is to be measured. The optical fiber can comprise first and second Fiber Bragg Gratings (FBGs). An optical fiber pressure sensor apparatus can comprise a first optical fiber anchor, to which a first portion of the optical fiber is secured, and a second optical fiber anchor, to which a second portion of the optical fiber is secured. A gasket can be longitudinally arranged between the first and second anchors and can include a passage through which a third portion of the optical fiber can pass. The gasket can be more elastic or compliant than the first and second anchors. The first and second anchors and the gasket can be arranged to use the elastic or compliant nature of the gasket such as to allow at least one of longitudinal stretching or longitudinal compression of the optical fiber between the first and second anchors to sense pressure at an internal location within a human body. The first FBG can be located at the first anchor and the second FBG can extend distally beyond the second anchor. The elongated member can define an opening configured to receive the optical fiber pressure sensor apparatus.

Each of these non-limiting examples described above can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

In an example, the circuits described herein, including its various elements discussed in this document, can include a combination of hardware and software. For example, one or more portions, elements, or circuits included can be implemented, such as using an application-specific circuit constructed to perform one or more particular functions or a general-purpose circuit programmed to perform such function(s). Such a general-purpose circuit (e.g., a processor circuit) can include, but is not limited to, a microprocessor or a portion thereof, a microcontroller or portions thereof, and a programmable logic circuit or a portion thereof, such as configured to execute or otherwise perform instructions stored within or on a medium readable by a machine or device, such as a memory circuit.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus comprising:
an elongated assembly, at least a portion of which is sized, shaped, or otherwise configured to be inserted into a human body to measure a pressure at an internal location within the human body, wherein the elongated assembly includes:
a guidewire including a solid core wire having an outer surface and a length, a portion of the outer surface defining a groove extending along a portion of the length of the core wire, the core wire including:
a first portion having a first diameter and a second portion having a second diameter, wherein the second diameter is greater than the first diameter, and wherein the second portion defines a cradle sized and arranged to receive an optical fiber pressure sensor;
an optical fiber positioned within the groove and extending longitudinally along the guidewire, the optical fiber configured to communicate light between a location outside of the human body and a portion of the optical fiber that is to be located at or near the internal location within the human body at which the pressure is to be measured; and
the optical fiber pressure sensor coupled to the optical fiber and configured to be located on the elongated assembly to allow positioning at or near the internal location within the human body at which pressure is to be measured.

2. The apparatus of claim 1, wherein the groove is sized for and carries only one optical fiber, and wherein the only one optical fiber has a diameter of between 25 micrometers and 30 micrometers, inclusive.

3. The apparatus of claim 1, wherein the optical fiber extends within the groove helically along at least a portion of the length of the core wire.

4. The apparatus of claim 1, wherein at least a portion of the guidewire defines a longitudinal optical fiber carrier that extends longitudinally along at least a portion of the length of the guidewire, wherein the optical fiber carrier includes the groove in the guidewire.

5. The apparatus of claim 1, wherein the guidewire comprises multiple filaments, and wherein an interstice between adjacent filaments defines at least a portion of the optical fiber carrier.

6. The apparatus of claim 1, wherein the at least one optical fiber pressure sensor comprises a Fiber Bragg Grating (FBG) interferometer.

7. The apparatus of claim 6, wherein the FBG interferometer comprises at least two Fiber Bragg Gratings, wherein the at least two Fiber Bragg Gratings are arranged or otherwise configured to permit optically discriminating, at or near the internal location within the body at which pressure is to be measured, between a change in pressure and a change in temperature.

8. The apparatus of claim 1, wherein the at least one optical fiber pressure sensor comprises two or more optical fiber pressure sensors that are configured to operate at different wavelengths.

9. The apparatus of claim 1, further comprising an optical fiber ribbon comprising a plurality of optical fibers, the optical fiber ribbon disposed about an outer surface of the elongated member.

10. The apparatus of claim 9, comprising a plurality of imaging gratings configured to couple light into or out of one or more respective optical fibers of the ribbon.

11. The apparatus of claim 1, comprising:
at least one coil disposed about at least a portion of the elongated member.

12. The apparatus of claim 1, wherein the core wire includes a distal core wire portion and a proximal core wire portion, wherein the distal core wire portion includes a first material and the proximal core wire portion includes a second material different from the first material, and wherein the distal core wire portion includes the second portion that defines the cradle.

13. The apparatus of claim 12, wherein the distal core wire portion does not define the groove.

14. The apparatus of claim 1, wherein the second portion includes a first section having the second diameter and a second section having a third diameter different from the second diameter, and wherein both the second diameter and the third diameter are greater than the first diameter.

15. The apparatus of claim 1, wherein the first portion is coaxial with the second portion.

16. The apparatus of claim 1, further comprising:
at least one coil disposed about the second portion.

17. The apparatus of claim 16, wherein the at least one coil includes a first coil having a first diameter and a second coil having a second diameter, wherein the second diameter is different from the first diameter.

18. The apparatus of claim 1, wherein the cradle is sized and arranged to receive a cylindrically shaped optical fiber pressure sensor.

19. The apparatus of claim 1, wherein the cradle defines at least two inner surfaces to accommodate features of the optical fiber pressure sensor.

20. The apparatus of claim 19, wherein a proximal portion of the optical fiber pressure sensor rests on a first one of the inner surfaces of the cradle and a distal portion of the optical fiber pressure sensor is suspended above a second one of the inner surfaces of the cradle.

21. The apparatus of claim 12, further comprising:
   a tubular connector to couple the distal core wire portion to the proximal core wire portion.

22. The apparatus of claim 12, wherein the distal core wire portion is coupled to the proximal core wire portion at a joint.

* * * * *

UNITED STATES PATENT AND TRADEMARK OFFICE
CERTIFICATE OF CORRECTION

PATENT NO. : 10,506,934 B2  
APPLICATION NO. : 14/403935  
DATED : December 17, 2019  
INVENTOR(S) : Eberle et al.

Page 1 of 2

It is certified that error appears in the above-identified patent and that said Letters Patent is hereby corrected as shown below:

On the Title Page

In Column 2, item (56), under "Other Publications", Line 2, delete "Jul. 12, 2016"," and insert --Jan. 18, 2016",-- therefor On page 4, in Column 1, item (56), under "Other Publications", Line 2, delete "Applcation" and insert --Application-- therefor On page 4, in Column 1, item (56), under "Other Publications", Line 8, delete "Hernodynamics" and insert --Hemodynamics-- therefor In the Drawings Sheet 22 of 40, Fig. 25, reference numeral 2416, delete "2416" and insert --2516-- therefor In the Specification In Column 10, Line 31, delete "300" and insert --100-- therefor In Column 11, Line 4, delete "300" and insert --100-- therefor In Column 19, Line 55, delete "804." and insert --800.-- therefor In Column 21, Line 10, delete "904." and insert --900.-- therefor In Column 21, Line 19, delete "904." and insert --900.-- therefor In Column 22, Line 35, delete "1004." and insert --1000.-- therefor Signed and Sealed this  
Sixth Day of October, 2020

Andrei Iancu  
*Director of the United States Patent and Trademark Office*

CERTIFICATE OF CORRECTION (continued)
U.S. Pat. No. 10,506,934 B2

In Column 23, Line 36, delete "1106" and insert --1102-- therefor

In Column 24, Line 9, delete "1204" and insert --1200-- therefor

In Column 25, Line 23, delete "1402" and insert --1404-- therefor

In Column 30, Line 5, delete "1912" and insert --1910-- therefor

In Column 36, Line 15, delete "202" and insert --2302-- therefor

In Column 50, Line 56, delete "4016." and insert --4012.-- therefor

In Column 51, Line 39, delete "4116." and insert --4112.-- therefor